(12) United States Patent
Nikolovska-Coleska et al.

(10) Patent No.: US 9,862,746 B2
(45) Date of Patent: Jan. 9, 2018

(54) COMPOSITIONS AND METHODS RELATING TO HINDERING DOT1L RECRUITMENT BY MLL-FUSION PROTEINS

(71) Applicant: The Regents of the University of Michigan, Ann Arbor, MI (US)

(72) Inventors: Zaneta Nikolovska-Coleska, Ann Arbor, MI (US); Chenxi Shen, Beijing (CN); Jay Hess, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 44 days.

(21) Appl. No.: 14/763,596

(22) PCT Filed: Feb. 14, 2014

(86) PCT No.: PCT/US2014/016377
§ 371 (c)(1),
(2) Date: Jul. 27, 2015

(87) PCT Pub. No.: WO2014/127191
PCT Pub. Date: Aug. 21, 2014

(65) Prior Publication Data
US 2015/0368300 A1 Dec. 24, 2015

Related U.S. Application Data

(60) Provisional application No. 61/765,403, filed on Feb. 15, 2013.

(51) Int. Cl.
| | |
|---|---|
| *A61K 31/551* | (2006.01) |
| *C07D 243/10* | (2006.01) |
| *A61K 45/06* | (2006.01) |
| *C07K 7/06* | (2006.01) |
| *G01N 33/574* | (2006.01) |
| *C07K 14/82* | (2006.01) |
| *A61K 31/352* | (2006.01) |
| *A61K 31/437* | (2006.01) |
| *A61K 31/4402* | (2006.01) |
| *A61K 31/454* | (2006.01) |
| *A61K 31/496* | (2006.01) |
| *A61K 31/5377* | (2006.01) |
| *A61K 31/5513* | (2006.01) |
| *A61K 38/08* | (2006.01) |
| *C07D 213/74* | (2006.01) |
| *C07D 261/20* | (2006.01) |
| *C07D 311/76* | (2006.01) |
| *C07D 405/04* | (2006.01) |
| *C07D 409/04* | (2006.01) |
| *C07D 519/00* | (2006.01) |

(52) U.S. Cl.
CPC ............ *C07K 7/06* (2013.01); *A61K 31/352* (2013.01); *A61K 31/437* (2013.01); *A61K 31/4402* (2013.01); *A61K 31/454* (2013.01); *A61K 31/496* (2013.01); *A61K 31/5377* (2013.01); *A61K 31/5513* (2013.01); *A61K 38/08* (2013.01); *A61K 45/06* (2013.01); *C07D 213/74* (2013.01); *C07D 261/20* (2013.01); *C07D 311/76* (2013.01); *C07D 405/04* (2013.01); *C07D 409/04* (2013.01); *C07D 519/00* (2013.01); *C07K 14/82* (2013.01); *G01N 33/57426* (2013.01); *C07K 2319/00* (2013.01); *G01N 2500/02* (2013.01)

(58) Field of Classification Search
CPC ...... C07K 7/06; C07K 14/82; C07K 2319/00; G01N 33/57426; G01N 2500/02; A61K 45/06; A61K 31/352; A61K 31/437; A61K 31/4402; A61K 31/454; A61K 31/496; A61K 31/5377; A61K 38/08; A61K 31/5513; C07D 213/74; C07D 261/20; C07D 311/76; C07D 405/04; C07D 409/04; C07D 519/00
See application file for complete search history.

(56) References Cited

U.S. PATENT DOCUMENTS

| | | |
|---|---|---|
| 2005/0027000 A1 | 2/2005 | Reed et al. |
| 2005/0048634 A1 | 3/2005 | Zhang et al. |

FOREIGN PATENT DOCUMENTS

| | | |
|---|---|---|
| WO | 01/04928 | 7/2001 |
| WO | 03/073999 | 9/2003 |
| WO | 2009/086303 | 7/2009 |
| WO | 2010/151799 | 12/2010 |
| WO | 2011/029054 | 3/2011 |
| WO | 2012/119079 | 9/2012 |
| WO | 2012/159085 | 11/2012 |

OTHER PUBLICATIONS

Daigle et al, Potent inhibition of DOT1 L as treatment of MLL-fusion leukemia, Blood, 2013, 122, pp. 1017-1025.*
Rubnitz et al, Acute mixed lineage leukemia in children: the experience of St Jude Children's Research Hospital, Blood, 2009, 113, pp. 5083-5089.*
Mertens-Talcott et al, Ellagic acid and quercetin interact synergistically with resveratrol in the induction of apoptosis and cause transient cell cycle arrest in human leukemia cells, Cancer Letters, 2005, 218, pp. 141-151.*

(Continued)

*Primary Examiner* — Julie Ha
*Assistant Examiner* — Li Ni Komatsu
(74) *Attorney, Agent, or Firm* — Casimir Jones, SC

(57) ABSTRACT

The present invention relates to MLL fusion proteins (e.g., AF9 and ENL), which activate target genes in part via recruitment of histone methyltransferase DOT1L. In particular, the present invention provides the AF9/ENL binding site in DOT1L and agents that block the protein-protein interactions between AF9/ENL and DOT1L, therefore inhibiting the activity of DOT1L, and inhibiting MLL-fusion protein associated leukemia.

3 Claims, 23 Drawing Sheets

(56) References Cited

OTHER PUBLICATIONS

Prasad et al, Purpurogallin, a scavenger of polymorphonuclear leukocyte-derived oxyradicals, Molecular and Cellular Biochemistry, 1994, 139, pp. 27-32.*

Purpurogallin, from http://www.sigmaaldrich.com/catalog/product/sigma/p7380?lang=en&region=US, pp. 1-3, accessed Apr. 19, 2017.*

Kasimsetty et al, Colon Cancer Chemopreventive Activities of Pomegranate Ellagitannins and Urolithins, J. Agric. Food Chem., 2010, 58, pp. 2180-2187.*

Zulkipli et al, Medicinal Plants: A Potential Source of Compounds for Targeting Cell Division, Drug Target Insights, 2015, 9, pp. 9-19.*

Zhang, W. et al. "An Af9 cis-element directly targets Dot1 a to mediate transcriptional repression of the [alpha]ENaC gene." American Journal of Physiology, 2013, vol. 304, No. 4, pp. F367-F375.

Bonacorso et al. "The first sysnthesis of dihydro-3H-pyrido [2,3-b] [1,4] diazepinolas and a new alternative approach for diazepinone analogues" Tetrahedron Letters, vol. 48, No. 28, 2007, pp. 4835-4838.

"DOT1L Human" UNIPROT, Dec. 4, 2007.

European Search Report, EP patent application No. 14751922.7, dated Nov. 25, 2016.

Database Registry, Chemical Abstracts Service, Columbus, Ohio, US; 2008, "1H-Dibenzo[b,e][1,4] diazepin-1-one, 10-[(4-ethylphenyl)sulfonyl]-11-(2-furanyl)-2,3,4,5,10,11-hexahydro-", Database accession No. 1029737-65-2.

Database Registry, Chemical Abstracts Service, Columbus, Ohio, US; 2001, "Cyclohexanecarboxylic acid, 6-oxo-6H-dibenzo[b,d]pyran-3-yl ester", Database accession No. 315712-66-4.

Database Registry, Chemical Abstracts Service, Columbus, Ohio, US; 2001, "2,4,6-Cycloheptatrien-1-one, 5-nitro-2-(2-pyridinylamino)-", Database accession No. 314040-29-4.

Database Registry, Chemical Abstracts Service, Columbus, Ohio, US; 2006, "2H-Benzimidazol-2-one, 1,3-dihydro-5-[(2-pyridinylmethyl)amino]-", Database accession No. 876898-01-0.

Porsolt R. D. et al. "The effects of exifone, a new agent for senile memory disorder, on two models of memory in the mouse" Pharmacology Biochemistry and Behavior, vol. 27, No. 2, 1987, pp. 253-256.

Database Chemical Abstracts Service, Columbus, Ohio, US; Bonacorso, Helio G. et al: "Regiospecific synthesis of 3H-pyrido[2,3-b][1,4]diazepin-4(5H)-ones via haloform reaction with the isolation of N3-[3-oxo-4,4,4-trichloroalk-1-en-1-al]-2,3-diaminopyridine intermediates" retrieved from STN Database accession No. 2009:934145; 7 Bonacorso, Helio G. et al: "Regiospecific synthesis of 3H-pyrido[2,3-b][1,4]diazepin-4(5H)-ones via haloform reaction with the isolation of N3-[3-oxo-4,4,4-trichloroalk-1-en-1-yl]-2,3-diaminopyridine intermediates", 2009, pp. 1-2.

Database Registry [Online] Chemical Abstracts Service, Columbus, Ohio, US; 2003, Anonymous, Database accession No. 515124-14-8.

Database Registry [Online] Chemical Abstracts Service, Columbus, Ohio, US; 2003, Database accession No. 544691-67-0.

Database Registry [Online] Chemical Abstracts Service, Columbus, Ohio, US; 2006, Database accession No. 902885-27-2.

Database Registry [Online] Chemical Abstracts Service, Columbus, Ohio, US; 2007, Database accession No. 931365-82-1.

Database Embase [Online] Elsevier Science Publishers, Amsterdam, NL; 1973, Lenfeld J. et al. "On pharmacology of isothebaine", Database accession No. EMB-1974176453 & Lenfeld J. et al. "On pharmacolgy of isothebaine" Acta Universitatis Palackianae Olomucensis Facultatis Medicae 1973, vol. No. 66, 1973, pp. 169-184.

Database Registry [Online] Chemical Abstracts Service, Columbus, Ohio, US; 2004, Database accession No. 670259-06-0.

Database Registry [Online] Chemical Abstracts Service, Columbus, Ohio, US; 2001, Database accession No. 362001-43-2.

Database Registry [Online] Chemical Abstracts Service, Columbus, Ohio, US; 2001, Database accession No. 330958-01-5.

Database Registry [Online] Chemical Abstracts Service, Columbus, Ohio, US; 2006, Database accession No. 904458-77-1.

Database Registry [Online] Chemical Abstracts Service, Columbus, Ohio, US; 2006, Database accession No. 904441-02-7.

DeGuest G. et al. "One-pot synthesis og 2,3-dihydropyrolopyridinones using in situr generated formimines" Organic Letters, 14(23), 6012-6015, vol. 8, No. 25, 2006, pp. 5889-5892.

Database Registry [Online] Chemical Abstracts Service, Columbus, Ohio, US; 2006, Database accession No. 902568-17-6.

Database Registry [Online] Chemical Abstracts Service, Columbus, Ohio, US; 2006, Database accession No. 902501-42-2.

Ayton, P.M et al., "Molecular mechanisms of leukemogenesis mediated by MLL fusion proteins" (2001) Oncogene 20: 5695-5707.

Daser, A., et al., "Extending the repertoire of the mixed-lineage leukemis gene MLL in leukemogenesis" (2004) Genes & development 18: 965-974.

Eguchi, M. et al., "The Role of the MLL Gene in Infant Leukemia" (2003) International journal of hematology 78: 390-401.

Krivtsov, A.V. et al., "MLL translocations, histone modifications and leukemia stem-cell development" (2007) Nature reviews Cancer 7: 823-833.

Bitoun, E. et al., "The mixed-lineage leukemia fusion partner AF4 stimulates RNA polymerase II transcriptional elongation and mediates corrodinated chromatin remodeling" (2007) Human molecular genetics 16: 92-106.

Mueller, D. et al., "A role for the MLL fusion partner ENL in transcriptional elongation and chromatin modification" (2007) Blood 110: 4445-4454.

Okada. Y. et al., "hDOT1L Links Histone Methylation to Leukemogenesis" (2005) Cell 121: 167-178.

Zeisig, D.T. et al., "The eleven-nineteen-leukemia protein ENL connects nuclear MLL fusion partners with chormatin" (2005) Oncogene 24: 5525-5532.

Biswas, D. et al., "Function of leukemogenic mixed lineage leukemia 1 (MLL) fusion proteins through distinct parter protein complexes" (2011) PNAS 108: 15751-15756.

Lin, C. et al., "AFF4, a component of the ELL/p-TEFb elongation complex and a shared subunit of MLL chimeras can link transcription elongation to leukemia" (2010) Mol Cell 37: 429-437.

Yokoyama, A. et al., A higher-order complex containing AF4- and ENL- family proteins with P-TEFb facilitates oncogenic and physiologic MLL-dependent transcription (2010) Cancer cell 17: 198-212.

Miline, T.A. et al., "Leukemogenic MLL Fusion Proteins Bind across a Broad Region of the Hox a9 Locus, Promoting Transcription and Multiple Histone Modifications" (2005) Cancer Res 65: 11367-11374.

Krivtsov, A.V. et al., "H3K79 methylation profiles define murine and human MLL-AF4 leukemias" (2008) Cancer cell 14: 355-368.

Bernt, K.M. et al., "MLL-rearranged Leukemia is Dependent on Aberrant H3K79 Methylation by DOT1L" (2011) Cancer cell 20: 66-78.

Chang, MJ, et al., "Histone H3 Lysine 79 Methyltransferase Dot1 is Required for Immortalization by MLL Oncogenes" (2010) Cancer Res 70: 10234-10242.

Jo, S.Y., et al.,"Requirement for DOT11 in murine postnatal hematopoiesis and leukemogenesis by MLL translocation" (2011) Blood 117: 4759-4768.

Nguyen, A.T. et al., "DOT1L, the H3K79 methyltransferase, is required for MLL-AF9-mediated leukeomgenesis?" (2011) Blood 117: 6912-6922.

Nguyen, A.T. et al., "The diverse functions of Dot1 and H3K79 methylation" (2011) Genes Dev 25: 1345-1358.

Feng, Y. et al., "Early mammalian erythropoiesis requires the Dot1L methyltransferase" (2010) Blood 116, 4483-4491.

Jones, B. et al., "The Histone H3K79 Methyltransferase Dot1L Is Essential for Mammalian Development and Heterochromatin Structure" (2008) PLoS Genet 4, e1000190.

(56) References Cited

OTHER PUBLICATIONS

Zhang, W. et al., "Aldosterone-induced Sgk1 relieves Dot1a-Af9-mediated transcriptional repression of epithelial Na+ channel alpha" (2007) J Clin Invest 117: 773-783.

Dobson, C.L. et al., "The Mll—AF9 gene fusion in mice controls myeloproliferation and specifies acute myeloid leukaemogenesis" (1999) Embo J 18: 3564-3574.

Zhang, W. et al., "Dot1a-AF9 Complex Mediates Histone H3 Lys-79 Hypermethylation and Repression of ENaCa in and Aldosterone-sensitive Manner" (2006) J Biol Chem 281: 18059-18068.

Srinivasan, R. S., et al., "The synthetic peptide PFWT disrupts AF4-AF9 protein complexes and induces apoptosis in t(4;11) leukemia cells" (2004) Leukemia 18, 1364-1372.

Slany, R.K. et al., "The Oncogenic Capacity of HRX-ENL Requires the Transcriptional Transactivation Activity of ENL and the DNA Binding Motifs of HRX" (1998) Mol Cell Biol 18: 122-129.

Shen, C. et al., "Targeting Recruitment of Disruptor of Telomeric Silencing 1-like (DOT1L)" (2013) J Biol Chem. 288 (42): 30585-30596.

International Search Report and Written Opinion dated May 1, 2014, PCT/US2014/016377 (14 pages).

Basavapathruni, A. et al., "Conformational adaptation drives potent, selective and durable inhibition of the human protein methyltransferase DOT1L" (2012) Chemical and Biology & Drug Design, 80(6)pp. 971-980.

Daigle, S.R. et al., "Selective Killing of Mixed Lineage Leukemia Cells by a Potent Small-Molecule DOT1L Inhibitor" (2011) Cancer Cell, vol. 20, :35-65.

Schulze, J.M. et al., "YEATS domain proteins: a diverse family with many links to chromatin modification and transcription" (2009) Biochem Cell Biol 87: 65-754.

* cited by examiner

A

B

A

```
                    Helix 1           Helix 2
AF9 497 GECDKAYLDELVELHRRLMTLRERHILQQIVNLIEE  (SEQ ID NO: 21)
ENL 489 GTYDKAYTDELVELHRRLMALRERNVLQQIVNLIEE  (SEQ ID NO: 22)
          *  ****  ***********:****::**********
                            Helix 3
AF9 533 TGHFHITNTTFDFDLCSLDKTTVRKLQSYLETSGTS 568 (SEQ ID NO: 21)
ENL 525 TGHFNVTNTTFDFDLFSLDETTVRKLQSCLEAVAT  559 (SEQ ID NO: 22)
          ****::********* *** ******** **:    *
```

B

ENL (489-544)

$K_D$ (nM) = 2,820 ± 1,687
$k_{on}$ (M⁻¹ s⁻¹) = 1,340 ± 245
$k_{off}$ (s⁻¹) = 0.0038 ± 0.002

ENL (523-559)

$K_D$ (nM) = 14,567 ± 2,098
$k_{on}$ (M⁻¹ s⁻¹) = 188 ± 30
$k_{off}$ (s⁻¹) = 0.0027 ± 0.0001

A

B

A

865 LPISIPLSTVQPNKLP 880 (SEQ ID NO: 13)

761 LMVKITLDLLSRIP 774 (SEQ ID NO: 14)

B

COMPOSITIONS AND METHODS RELATING TO HINDERING DOT1L RECRUITMENT BY MLL-FUSION PROTEINS

CROSS-REFERENCE TO RELATED APPLICATIONS

The present application is a 371 U.S. National Phase Entry of pending International Application No. PCT/US2014/016377, filed Feb. 14, 2014, which claims priority to U.S. Provisional Patent Application No. 61/765,403, filed Feb. 15, 2013, the contents of which are incorporated by reference in their entireties.

FIELD OF THE INVENTION

The present invention relates to MLL fusion proteins (e.g., AF9 and ENL), which activate target genes in part via recruitment of histone methyltransferase DOT1L. In particular, the present invention provides the AF9/ENL binding site in DOT1L and agents that block the protein-protein interactions between AF9/ENL and DOT1L, therefore inhibiting the activity of DOT1L, and inhibiting MLL-fusion protein associated leukemia. The agents and related compositions additionally find use in diagnostic and research settings.

BACKGROUND OF THE INVENTION

Epigenetic regulation of transcription through covalent modifications of histones is a fundamental mechanism of transcriptional regulation that is important for stem cell self-renewal as well as lineage commitment during development. Two broad groups of transcriptional regulators, the Trithorax (Trx) and Polycomb group Pc(G) proteins are the pivotal positive and negative regulators in this mechanism. Deregulation of transcription by disruption of both of these families of epigenetic regulators is emerging as a common cause of human malignancies.

Mixed lineage leukemia protein, MLL, is a Trx group protein that can be disrupted by fusion to a variety of translocation partners in human lymphoid and myeloid acute leukemia. As a result of chromosome translocation, the MLL N-terminus becomes fused to one of more than 60 partner proteins forming chimeric oncogenes which up-regulate the expression of HOX genes, blocking the hematopoietic differentiation and ultimately lead to acute leukemia (see, e.g., Ayton P M, Cleary M L (2001) Oncogene 20: 5695-5707; Daser A, Rabbitts T H (2004) Genes & development 18: 965-974; Eguchi M, Eguchi-Ishimae M, Greaves M (2003) International journal of hematology 78: 390-401; Krivtsov A V, Armstrong S A (2007) Nature reviews Cancer 7: 823-833). Leukemia mediated by MLL rearrangements possess unique clinical and biological features, and they are present in over 70% cases of infant leukemia (see, e.g., Biondi A, Cimino G, Pieters R, Pui C H (2000) Blood 96: 24-33) and in general account for approximately 5% of ALLs, 5%-10% of AMILs, and almost all cases of mixed-lineage leukemia (see, e.g., Huret J L, Dessen P, Bernheim A (2001) Leukemia 15: 987-989). Patients with leukemia harboring MLL translocations have a highly unfavorable prognosis with current treatments (see, e.g., Slany R K (2005) Hematol Oncol 23: 1-9). Thus novel therapeutic strategies are needed.

SUMMARY

The MLL fusion proteins, AF9 and ENL, activate target genes in part via recruitment of the histone methyltransferase DOT1L (Disruptor Of Telomeric silencing 1-Like) a non-SET domain enzyme catalyzing the methylation of histone 3 at lysine 79 (H3K79). Biochemical, biophysical and functional characterization of the interaction between DOT1L and MLL-fusion proteins, AF9/ENL was investigated during experiments conducted during the course of developing embodiments for the present invention. The AF9/ENL binding site in human DOT1L was mapped and the interaction site was identified to a 10 amino-acid region (DOT1L865-874) (DOT1L 865LPISIPLSTV874(SEQ ID NO:1)). This region is highly conserved in DOT1L from a variety of species. Alanine scanning mutagenesis analysis showed that four conserved hydrophobic residues from the identified binding motif are essential for the interactions with ENL/AF9. Binding studies demonstrated that the entire intact C-terminal domain of AF9/ENL is required for optimal interaction with DOT1L. Functional studies showed that the mapped AF9/ENL interacting site is essential for immortalization by MLL-AF9, indicating that DOT1L interaction with MLL-AF9 and its recruitment are required for transformation by MLL-AF9. Importantly, the global level of H3K79 methylation level was not affected. Thus, these results indicate that disruption of interaction between DOT1L and AF9/ENL is a therapeutic strategy with potentially fewer adverse effects than enzymatic inhibition of DOT1L for MLL-fusion protein-associated leukemia.

Accordingly, the present invention relates to MLL fusion proteins (e.g., AF9 and ENL) which activate target genes in part via recruitment of histone methyltransferase DOT1L. In particular, the present invention provides the AF9/ENL binding site in DOT1L and agents that block the protein-protein interactions between AF9/ENL and DOT1L, therefore inhibiting the activity of DOT1L, and inhibiting MLL-fusion protein associated leukemia. These agents are suitable for treating patients or hosts infected with MLL-fusion protein associated leukemia. The agents and related compositions additionally find use in diagnostic and research settings.

In certain embodiments, the present invention provides compositions comprising one or more agents capable of binding a region of an MLL-fusion protein known to interact with DOT1L.

The present invention is not limited to a particular type of MLL-fusion protein. In some embodiments, the MLL-fusion protein is AF9. In some embodiments, the MLL-fusion protein is ENL.

The present invention is not limited to a particular type of agent capable of binding a region of AF9 or ENL known to interact with DOT1L.

In some embodiments, the agent is a peptide. In some embodiments, the peptide is 865LPISIPLSTV874(SEQ ID NO:1) of DOT1L.

In some embodiments, the agent is a small molecule capable of binding a region of AF9 or ENL known to interact with DOT1L. In some embodiments, the small molecule has structural properties similar to 865LPISIPLSTV874(SEQ ID NO:1) of DOT1L.

In some embodiments, the small molecule is selected from the group consisting of

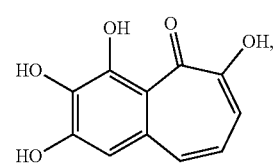

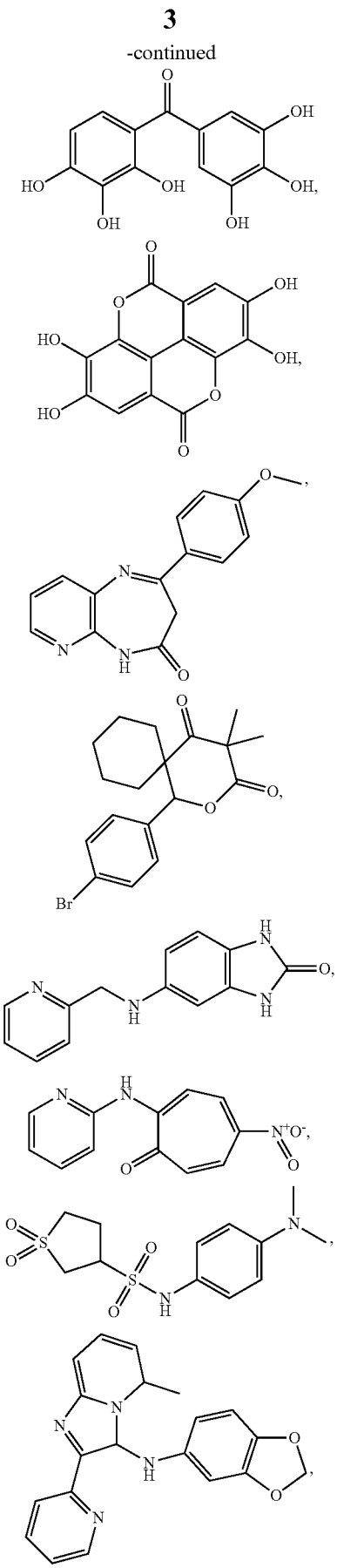
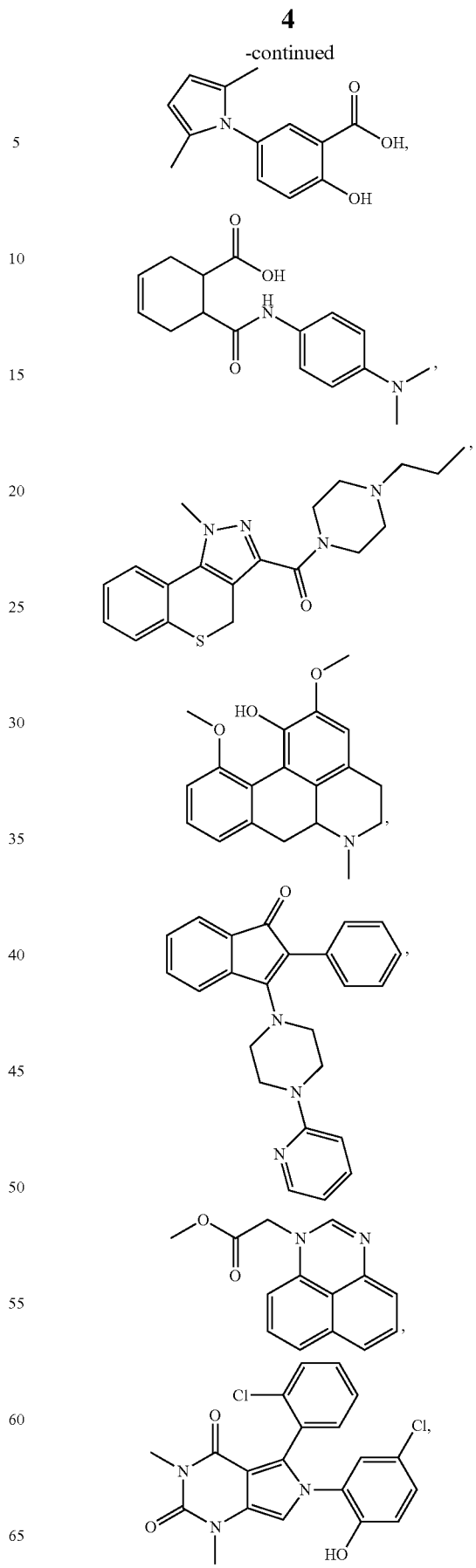

-continued

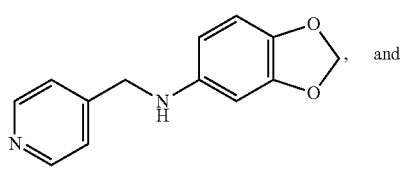, and

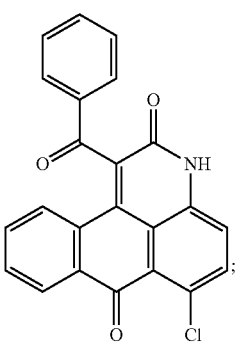;

including salts, esters, and prodrugs thereof, and including both R and S enantiomeric forms and racemic mixtures thereof.

In some embodiments, the small molecule is encompassed within Formula I:

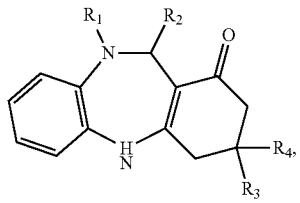
(Formula I)

including salts, esters, and prodrugs thereof, and including both R and S enantiomeric forms and racemic mixtures thereof. In some embodiments, R1 is selected from Hydrogen and

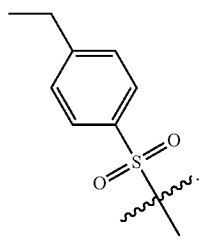 [SMILES: *S(=O)(=O)c1ccc(CC)cc1]

In some embodiments, R2 is selected from Hydrogen,

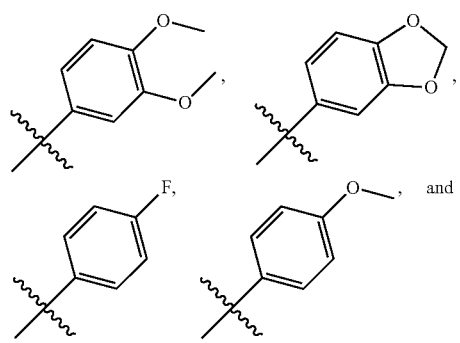

-continued

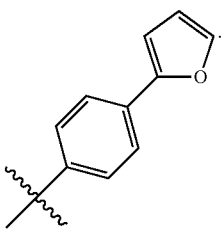

In some embodiments, R3 is Hydrogen or CH3. In some embodiments, R4 is Hydrogen or CH3. In some embodiments, the small molecule encompassed within Formula I is selected from

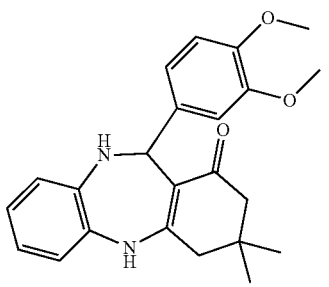,

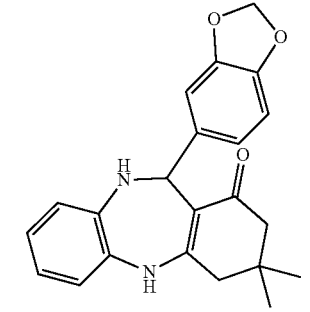,

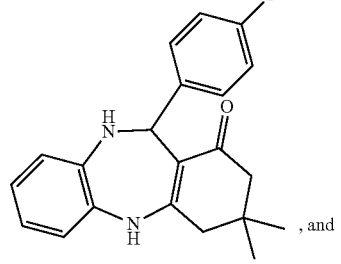, and

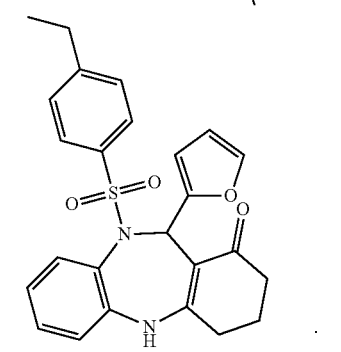

In some embodiments, the small molecule is encompassed within Formula II:

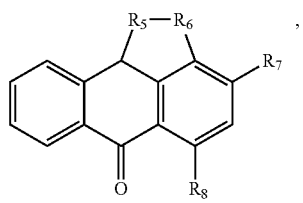
(Formula II)

including salts, esters, and prodrugs thereof, and including both R and S enantiomeric forms and racemic mixtures thereof. In some embodiments, R5 is selected from Hydrogen, O or NH. In some embodiments, R6 is selected from Hydrogen, O or NH. In some embodiments, R7 is selected from Hydrogen,

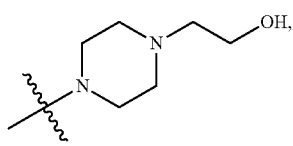 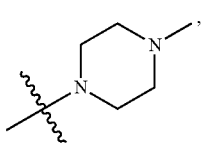

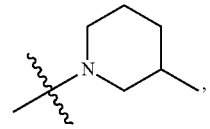 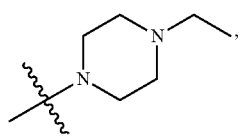

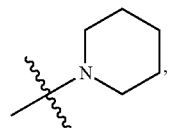 and 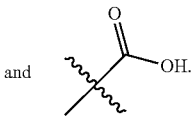

In some embodiments, R8 is selected from

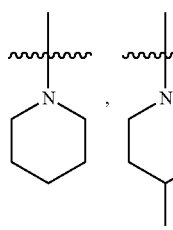 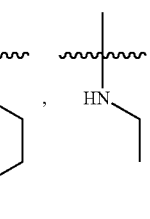 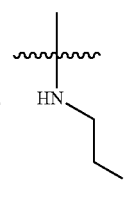

and Hydrogen. In some embodiments, the small molecule encompassed within Formula II is selected from

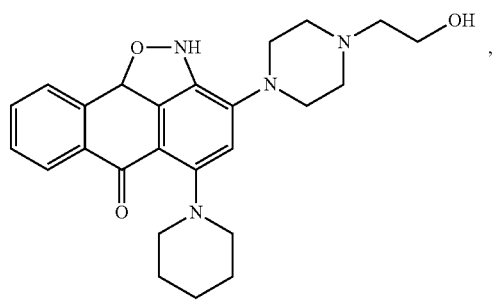

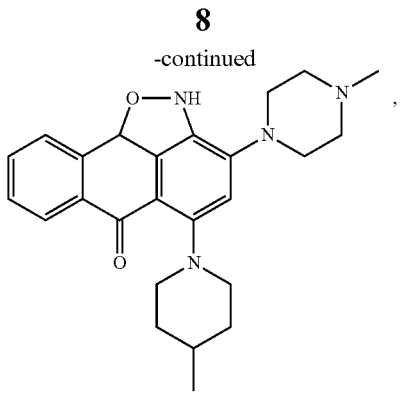

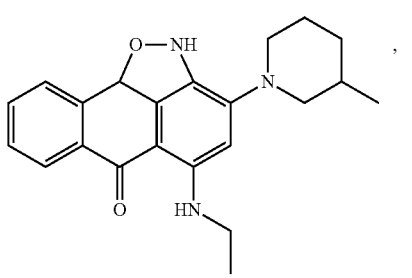

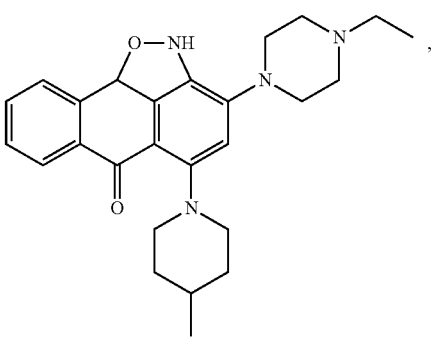

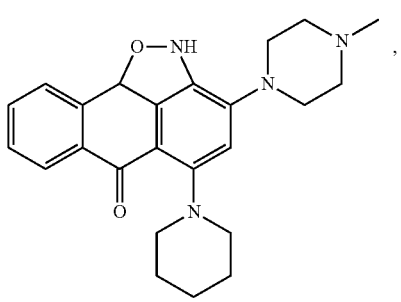

, and

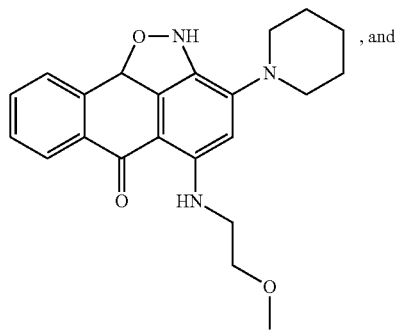

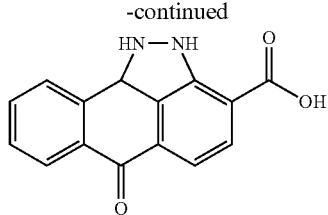

In some embodiments, the small molecule is encompassed within Formula III:

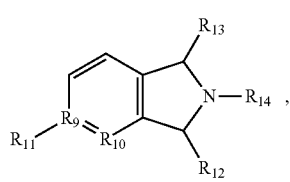 (Formula III)

including salts, esters, and prodrugs thereof, and including both R and S enantiomeric forms and racemic mixtures thereof. In some embodiments, R9 is selected from Hydrogen, N or C. In some embodiments, R10 is selected from Hydrogen, N or C. In some embodiments, R11 is selected from Hydrogen and

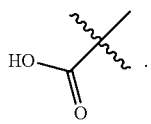

In some embodiments, R12 is selected from OH, Hydrogen,

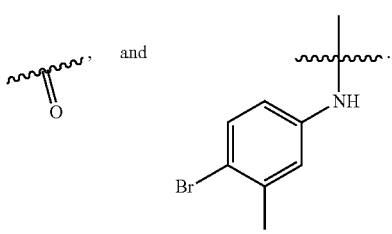

In some embodiments, R13 is selected from Hydrogen, OH and

In some embodiments, R14 is selected from Hydrogen,

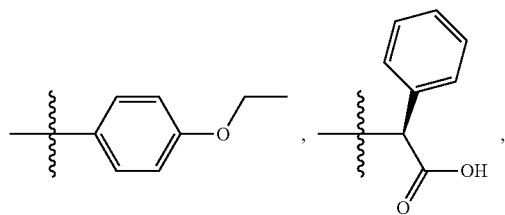

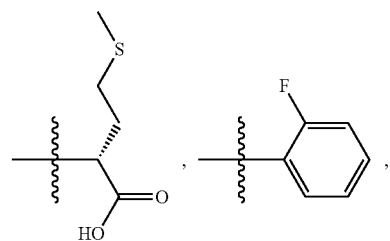

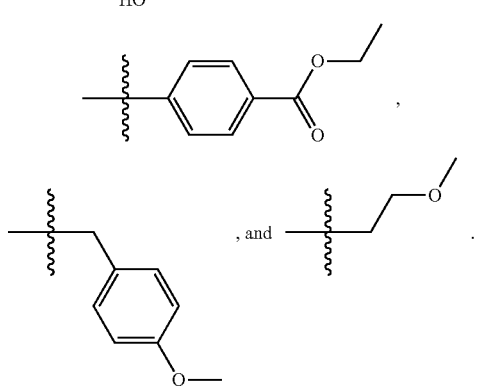

In some embodiments, the small molecule encompassed within Formula III is selected from

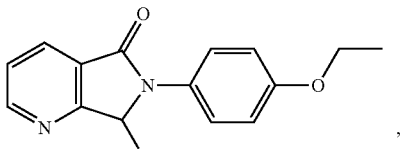

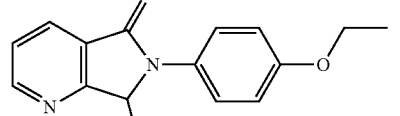

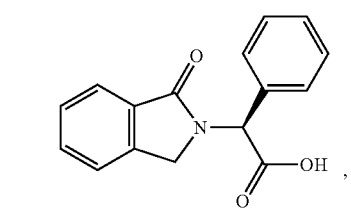

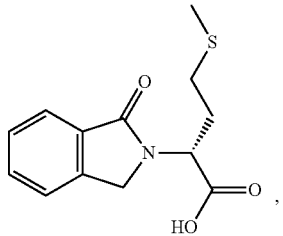

-continued

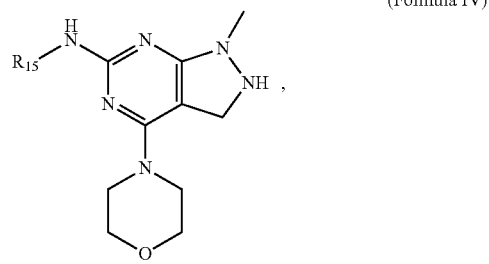

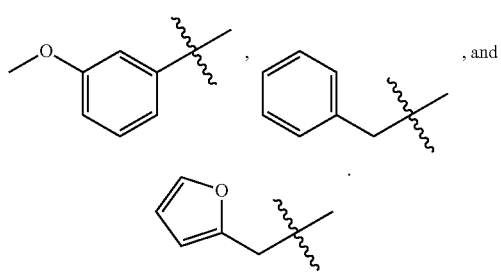

In some embodiments, the small molecule is encompassed within Formula IV:

(Formula IV)

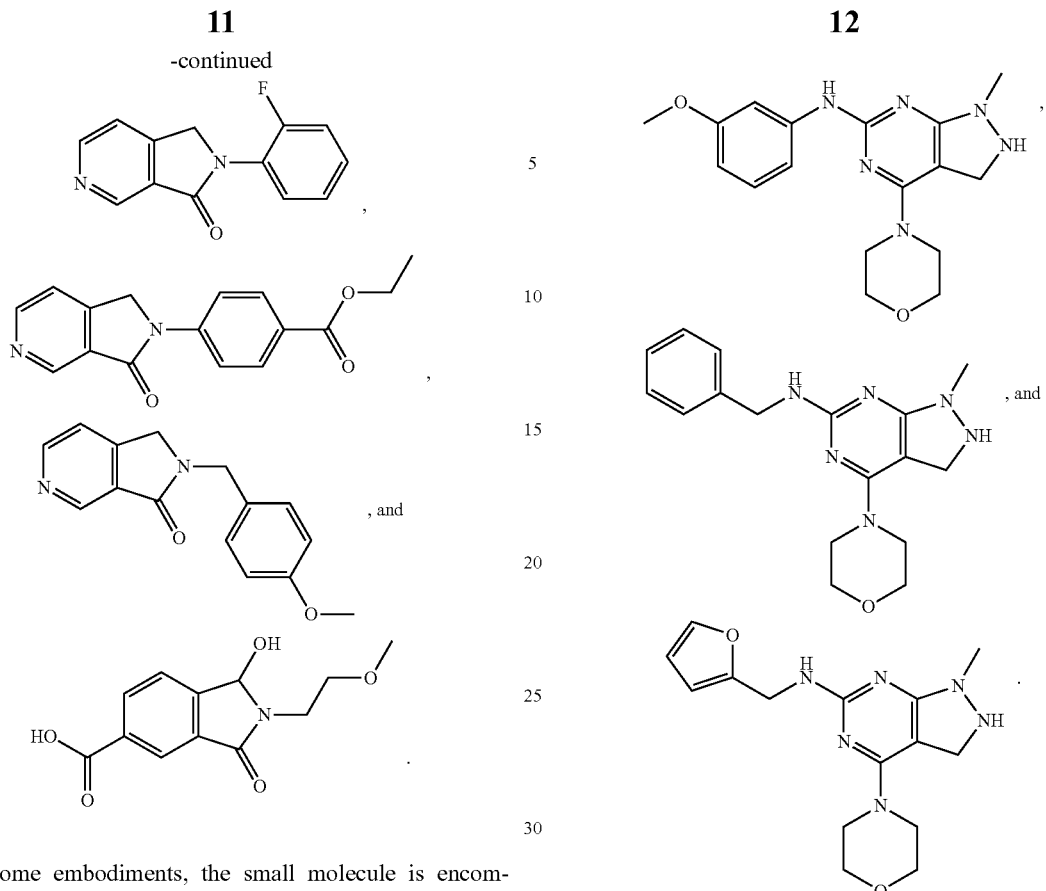

including salts, esters, and prodrugs thereof, and including both R and S enantiomeric forms and racemic mixtures thereof. In some embodiments, R15 is selected from Hydrogen,

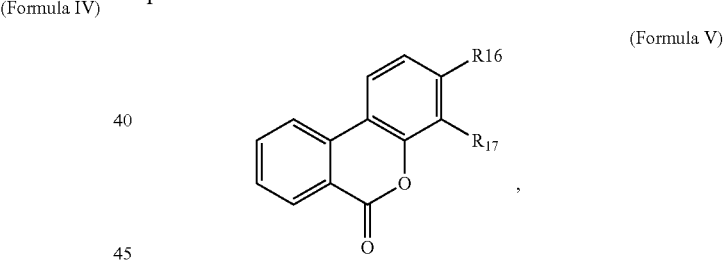

In some embodiments, the small molecule encompassed within Formula IV is selected from In some embodiments, the small molecule is encompassed within Formula V:

(Formula V)

including salts, esters, and prodrugs thereof, and including both R and S enantiomeric forms and racemic mixtures thereof. In some embodiments, R16 is selected from Hydrogen, OH and

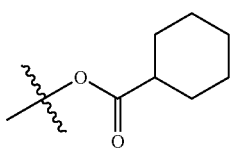

In some embodiments, R17 is selected from Hyrdogen and

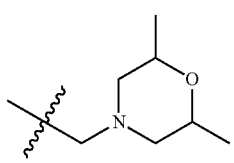

In some embodiments, the small molecule encompassed within Formula IV is selected from

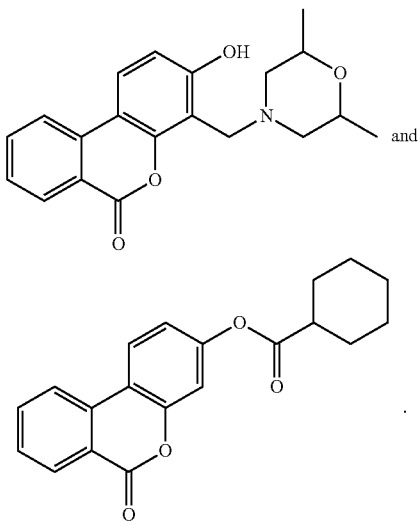

In some embodiments, the agent is a peptidomimetic designed and synthesized to mimic a peptide capable of binding a region of AF9 or ENL known to interact with DOT1L (e.g., 865LPISIPLSTV874(SEQ ID NO:1) of DOT1L).

In some embodiments, the agent is a cyclic peptide designed and synthesized to mimic a peptide capable of binding a region of AF9 or ENL known to interact with DOT1L (e.g., 865LPISIPLSTV874(SEQ ID NO:1) of DOT1L).

In some embodiments, the compositions further comprise one or more therapeutic agents known to treat cancer. The present invention is not limited to a particular type of cancer. In some embodiments the cancer is leukemia. In some embodiments, the leukemia is MLL-fusion protein associated leukemia.

For example, in some embodiments, such binding of the region of the AF9/ENL interaction site for DOT1L furthermore results in prevention of an AEP complex (e.g., wherein ENL associates with AF4, AF5q31, P-TEFb, and DOT1L). In some embodiments, such binding of the AF9/ENL interaction site for DOT1L furthermore results in prevention aberrant H3K79 methylation. In some embodiments, such binding of the region of AF9/ENL interaction site for DOT1L furthermore results in prevention of MLL-fusion associated leukemogenesis.

In certain embodiments, the present invention provides methods for inhibiting the binding of DOT1L to an MLL-fusion protein with an agent capable of binding a region of an MLL-fusion protein known to interact with DOT1L (e.g., a peptide capable of binding a region of an MLL-fusion protein known to interact with DOT1L) (e.g., a small molecule capable of binding an MLL-fusion protein known to interact with DOT1L). In some embodiments, the MLL-fusion protein is AF9. In some embodiments, the MLL-fusion protein is ENL.

In certain embodiments, the present invention provides methods for preventing MLL-fusion protein associated recruitment of DOT1L comprising administering to a subject experiencing or at risk for developing MLL-fusion protein associated recruitment of DOT1L an agent capable of binding a region of an MLL-fusion protein known to interact with DOT1L (e.g., a peptide capable of binding a region of an MLL-fusion protein known to interact with DOT1L) (e.g., a small molecule capable of binding a region of an MLL-fusion protein known to interact with DOT1L). In some embodiments, the MLL-fusion protein is AF9. In some embodiments, the MLL-fusion protein is ENL.

In certain embodiments, the present invention provides methods for treating MLL-fusion protein associated leukemia comprising administering to a subject suffering from MLL-fusion protein associated leukemia an agent capable of binding a region of an MLL-fusion protein known to interact with DOT1L (e.g., a peptide capable of binding a region of an MLL-fusion protein known to interact with DOT1L) (e.g., a small molecule capable of binding a region of an MLL-fusion protein known to interact with DOT1L). In some embodiments, the MLL-fusion protein is AF9. In some embodiments, the MLL-fusion protein is ENL.

In some embodiments, the methods further comprise administering to the subject therapeutic amounts of one or more therapeutic agents known to treat cancer. The present invention is not limited to a particular type of cancer. In some embodiments the cancer is leukemia. In some embodiments, the leukemia is MLL-fusion protein associated leukemia.

In certain embodiments, the present invention provides methods of screening for agents able to bind an MLL-fusion protein interaction site for DOT1L, comprising administering a candidate agent to a sample expressing an MLL-fusion protein, and detecting binding of the agent within the MLL-fusion protein interaction site for DOT1L. In some embodiments, the agent is a peptide. In some embodiments, the agent is a small molecule. In some embodiments, the MLL-fusion protein is AF9. In some embodiments, the MLL-fusion protein is ENL.

Additional embodiments will be apparent to persons skilled in the relevant art based on the teachings contained herein.

DEFINITIONS

Figure 1:
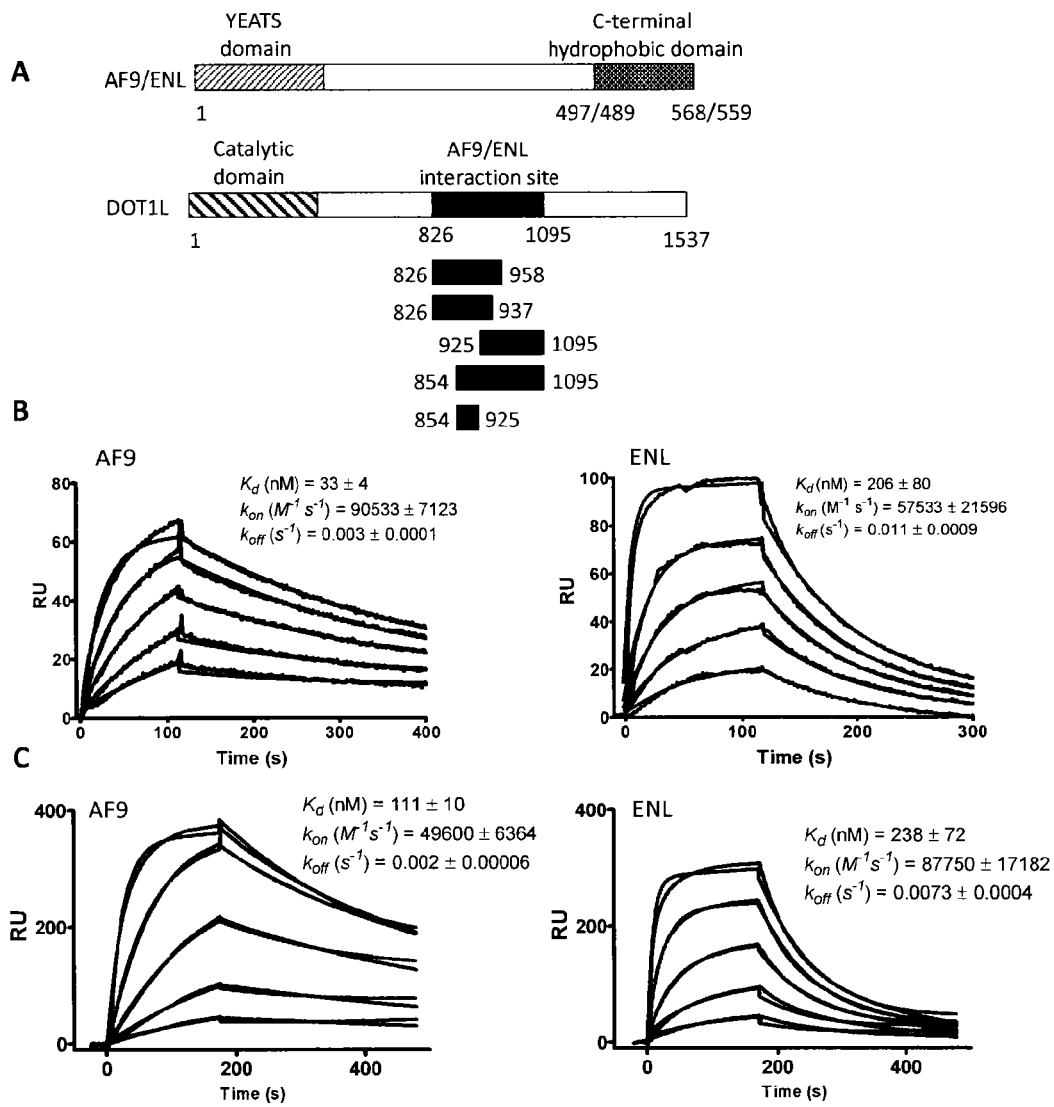
FIG. 1 shows interaction between DOT1 L and MLL-fusion proteins, AF9 and ENL, measured by surface plasmon resonance. A. Schematic presentation of AF9/ENL and DOT1 L proteins used for the binding studies. B. and C. Sensorgrams representing the concentration-dependent binding of the C-terminal domain of AF9 and ENL tested in concentration range from 0.01 to 3 μM, with (B) full length Flag-DOT1L and (C) Mocr-DOT1L (826-1095), both immobilized on a CM5 sensor chip. The $k_{on}$, $k_{off}$ and $K_D$ were calculated by simultaneous non-linear regression using 1:1 binding model and BIAevaluation 3.1 software. The experimental data are shown in black while the global fit analyses are shown in grey.

To facilitate an understanding of the present invention, a number of terms and phrases are defined below.

As used herein, the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

The term "derivative" of a small molecule, as used herein, refers to a chemically modified small molecule wherein the chemical modification takes place either at a functional group of the small molecule (e.g., compound) or on the aromatic ring.

As used herein, the term "subject" refers to organisms to be treated by the methods and agents of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of an agent of the present invention and optionally one or more other agents) for a condition characterized by MLL-fusion protein associated recruitment of DOT1L, and/or MLL-fusion protein associated leukemia.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In some embodiments, the "target cells" of the compositions and methods of the present invention include, refer to, but are not limited to, lymphoid cells or cancer cells. Lymphoid cells include B cells, T cells, and granulocytes. Granulocyctes include eosinophils and macrophages. In some embodiments, target cells are continuously cultured cells or uncultered cells obtained from patient biopsies.

As used herein, the term "co-administration" refers to the administration of at least two agent(s) (e.g., an agent of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the terms "non-specific binding" and "background binding" when used in reference to the interaction of a molecule with a protein or enzyme refers to an interaction that is not dependent on the presence of a particular structure.

As used herein, the term "modulate" refers to the activity of an agent (e.g., a peptide or small molecule of the present invention) to affect (e.g., to promote or retard) an aspect of cellular function, including, but not limited to, enzymatic activity, maturation, cell growth, replication, proliferation, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention relates to MLL fusion proteins (e.g., AF9 and ENL), which activate target genes in part via recruitment of histone methyltransferase DOT1L. In particular, the present invention provides the AF9/ENL binding site in DOT1L and agents that block the protein-protein interactions between AF9/ENL and DOT1L, therefore inhibiting the activity of DOT1L, and inhibiting MLL-fusion protein associated leukemia. These agents are suitable for treating patients or hosts infected with MLL-fusion protein associated leukemia. The agents and related compositions additionally find use in diagnostic and research settings.

Exemplary compositions and methods of the present invention are described in more detail in the following sections: I. Targeting DOT1L Recruitment; II. Exemplary Agents; III. Pharmaceutical Compositions, Formulations, and Exemplary Administration Routes and Dosing Considerations; IV. Drug Screens; and V. Therapeutic Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Targeting DOT1L Recruitment

Emerging findings from a number of groups suggest that the common MLL fusions, including MLL-AF4, MLL-AF9 and MLL-ENL, use a similar strategy for leukemic transformation. This involves recruitment of the histone methyltransferase (HMT), DOT1L (Disruptor Of Telomeric silencing 1-Like), a non-SET domain containing HMT solely responsible for catalyzing the methylation of histone 3 at lysine 79 (H3K79) (see, e.g., Bitoun E, Oliver P L, Davies K E (2007) Human molecular genetics 16: 92-106; Mueller D, et al., (2007) Blood 110: 4445-4454; Okada Y, et al., (2005) Cell 121: 167-178; Zeisig D T, et al., (2005) Oncogene 24: 5525-5532). Several multi-protein complexes involved in transcriptional activation/elongation were independently identified and studied, showing that all of them contain MLL fusion proteins together with DOT1L and/or p-TEFb (a complex of cyclinT and CDK9, which phosphorylates stalled RNA polymerase II) (see, e.g., Biswas D, et al., (2011) PNAS 108: 15751-15756; Bitoun E, Oliver P L, Davies K E (2007) Human molecular genetics 16: 92-106; Lin C, et al., (2010) Mol Cell 37: 429-437; Mueller D, et al., (2007) Blood 110: 4445-4454; Okada Y, et al., (2005) Cell 121: 167-178; Yokoyama A, et al., (2010) Cancer cell 17: 198-212; Zeisig D T, et al., (2005) Oncogene 24: 5525-5532). It has been reported that the MLL translocation partners, AF4, AF9, AF5q31 and ENL interact in a complex named ENL associated protein complex (EAP), which in addition to the core translocation partners, contains the p-TEFb together with the DOT1L (see, e.g., Mueller D, et al., (2007) Blood 110: 4445-4454). These findings were modified by several following reported studies describing similar complexes associated with DOT1L and p-TEFb as "effector units" but importantly not both at the same time. For example, it was demonstrated that ENL exists in two distinct complexes, one with DOT1L and one within an endogenous higher ordered complex (designated AEP) in which ENL associates with AF4, AF5q31, and P-TEFb (see, e.g., Yokoyama A, et al., (2010) Cancer cell 17: 198-212). In this model, ENL has dual roles and interacts with AEP and DOT1L recruiting them sequentially to the same target chromatin. This study showed that the AEP complex is required for sustained transcription of target genes and transformation of hematopoietic progenitors, while the recruitment of DOT1L by ENL tethered to the MLL fusion protein plays a role in the maintenance of transcriptional memory. The C-terminal AF9 domain in MLL-AF9 was also shown to form distinct higher order complexes through direct associations with AF4/P-TEFb and with DOT1L (see, e.g., Biswas D, et al., (2011) PNAS 108: 15751-15756). Notably, MLL-AF9-mediated target gene (HOXA9) expression and cell transformation depend on these protein-protein interactions and formation of the higher order complexes. These findings that DOT1L associates with MLL fusion proteins in several reported complexes, suggested that aberrant H3K79 methylation might be a shared mechanism of oncogenic transcriptional activation in MLL rearrangement leukemia. It is known that the recruitment of DOT1L results in hypermethylation of H3K79 on the prominent MLL-fusion downstream target loci Hoxa9 and Meis1 (see, e.g., Milne T A, et al., (2005) Cancer Res 65: 11367-11374). Genome-wide analysis revealed a distinct pattern of H3K79 methylation in human MLL-rearranged primary leukemia samples compared with normal proB cells and leukemia with other abnormalities (see, e.g., Krivtsov A V, et al., (2008) Cancer cell 14: 355-368). Transient knockdown or conditional knockout mice models have demonstrated that DOT1L is required for MLL-fusion mediated leukemic transformation and in vivo leukemia development and maintenance, indicating that there is a strong functional interconnection between complexes formed by MLL fusion proteins and DOT1L (see, e.g., Bernt K M, et al., (2011) Cancer cell 20: 66-78; Chang M J, et al., (2010) Cancer Res 70: 10234-10242; Jo S Y, et al., (2011) Blood 117: 4759-4768; Nguyen A T, et al., (2011) Blood 117: 6912-6922; Nguyen A T, Zhang Y (2011) Genes Dev 25: 1345-1358;

Zeisig D T, et al., (2005) Oncogene 24: 5525-5532). These findings illustrate the central role of the DOT1L recruitment and H3K79 methylation in leukemogenesis by controlling transcription of hematopoietic genes and implicate protein-protein interactions (PPI) between DOT1L and MLL oncogenic fusion proteins as a potential therapeutic target.

In experiments conducted during the course of developing embodiments for the present invention, the AF9/ENL-DOT1L interaction on biochemical, biophysical and functional level was characterized. It was demonstrated that only 10 amino acids in DOT1L are essential for the recruitment of DOT1L by MLL-AF9 and this interaction is required for transformation of MLL-AF9. Indeed, using SPR and FP based binding assays, ITC, HSQC NMR, immunoprecipitation and pull-down experiments, the binding affinity of these PPI were determined and the AF9/ENL interaction site defined to the region corresponding to DOT1L 865LPISIPLSTV874(SEQ ID NO:1). Importantly, the functional studies show that this interaction is required for transformation by MLL-AF9. These results indicate that disruption of this PPI represents a therapeutic strategy for MLL-fusion protein associated leukemia.

Accordingly, in certain embodiments, the present invention provides methods for treating and/or preventing MLL-fusion protein associated leukemia through, for example, inhibiting MLL-fusion protein associated recruitment of DOT1L. The present invention is not limited to a particular manner of inhibiting MLL-fusion protein associated recruitment of DOT1L. In some embodiments, inhibiting MLL-fusion protein associated recruitment of DOT1L is accomplished through preventing binding of DOT1L with AF9, ENL, and/or AF9/ENL. In some embodiments, preventing binding of DOT1L with AF9, ENL, and/or AF9/ENL is accomplished through blocking the region of AF9, ENL, and/or AF9/ENL that binds DOT1L with, for example, an agent (e.g., a peptide, a small molecule, peptidomimetic, a cyclic peptide) that binds the AF9/ENL interaction site thereby preventing DOT1L binding. In some embodiments, such an agent has binding properties similar to the region of DOT1L corresponding to DOT1L 865LPISIPLSTV874 (SEQ ID NO:1). In some embodiments, such binding of the region of AF9, ENL, and/or AF9/ENL that binds with DOT1L furthermore results in prevention of an AEP complex (e.g., wherein ENL associates with AF4, AF5q31, P-TEFb, and DOT1L). In some embodiments, such binding of the region of AF9, ENL, and/or AF9/ENL that binds with DOT1L furthermore results in prevention aberrant H3K79 methylation. In some embodiments, such binding of the region of AF9, ENL, and/or AF9/ENL that binds with DOT1L furthermore results in prevention of MLL-fusion associated leukemogenesis.

II. Exemplary Agents

The recent development of a specific small molecule inhibitor of DOT1L, EPZ004777, which is a competitive inhibitor of the methyl donor Sadenosyl-methionine provide proof of principle for the development of DOT1L inhibitors as targeted therapeutics for MLL-rearranged leukemia (see, e.g., Daigle S R, et al., (2011) Cancer cell 20: 53-65). However, constitutive and conditional knockout studies of DOT1L, which is the only known H3K79 methyltransferase, have shown it is essential for embryonic development, prenatal and postnatal hematopoiesis and cardiac function (see, e.g., Bernt, et al., (2011) Cancer Cell 20, 66-78; Jo, S. Y., et al., (2011) Blood 117, 4759-4768; Nguyen, A. T., et al., (2011) Blood 117, 6912-6922; Feng, Y., et al., (2010) Blood 116, 4483-4491; Jones, B., et al., (2008) PLoS Genet 4, e1000190). This universal and essential function of DOT1L in multiple cell types (see, e.g., Nguyen, A. T., and Zhang, Y. (2011) Genes Dev 25, 1345-1358) suggests that directly inhibiting DOT1L histone methyltransferase activity might be toxic. Consequently, development of therapeutic strategies allowing selective inhibition of DOT1L function is important and necessary.

In experiments conducted during the course of developing embodiments for the present invention, the PPI between DOT1L and AF9 or ENL, respectively, was validated as a promising therapeutic target and potential strategy for pharmacological targeting of DOT1L. The results indicate that disruption of AF9-DOT1L interaction abolishes MLL-AF9 leukemia transformation, without affecting the global level of H3K79 methylation level. More importantly, the results also suggest that selective disruption of this PPI is a promising therapeutic strategy with potentially fewer adverse effects than enzymatic inhibition of DOT1L for MLL-fusion protein associated leukemia.

As such, in certain embodiments, the present invention provides agents capable of targeting the MLL-fusion protein interaction site for DOT1L (e.g., an agent having binding properties similar to the region of DOT1L corresponding to DOT1L 865LPISIPLSTV874(SEQ ID NO:1)). In some embodiments, the MLL-fusion protein is AF9. In some embodiments, the MLL-fusion protein is ENL. In some embodiments, the present invention provides methods for treating MLL-fusion protein associated leukemia through inhibiting or blocking the biological activity of DOT1L, thereby inhibiting MLL-fusion protein associated leukemia. In certain embodiments, the present invention provides methods for screening drugs through identifying agents capable of, for example, binding with the MLL-fusion protein interaction site for DOT1L (e.g., the AF9/ENL interaction site for DOT1L) (e.g., an agent having binding properties similar to the region of DOT1L corresponding to DOT1L 865LPISIPLSTV874(SEQ ID NO:1)).

The present invention is not limited to certain types or kinds of agents capable of binding the MLL-fusion protein interaction site for DOT1L (e.g., the AF9/ENL interaction site for DOT1L).

In some embodiments, the agent is a peptide capable of binding the MLL-fusion protein interaction site for DOT1L (e.g., the AF9/ENL interaction site for DOT1L). In some embodiments, the peptide comprises 865LPISIPLSTV874 (SEQ ID NO:1) of DOT1L.

In some embodiments, the agent is a peptidomimetic designed and synthesized to mimic a peptide capable of binding a region of AF9 or ENL known to interact with DOT1L (e.g., 865LPISIPLSTV874(SEQ ID NO:1) of DOT1L).

In some embodiments, the agent is a cyclic peptide designed and synthesized to mimic a peptide capable of binding a region of AF9 or ENL known to interact with DOT1L (e.g., 865LPISIPLSTV874(SEQ ID NO:1) of DOT1L).

In some embodiments, the agent is a small molecule capable of binding the MLL-fusion protein interaction site for DOT1L (e.g., the AF9/ENL interaction site for DOT1L). Indeed, experiments conducted during the course of developing embodiments for the present invention identified and validated lead small molecules (e.g., compounds) targeting PPI between DOT1L and MLL-AF9 by employing the optimized FP-based assay (see, Examples 12, 13, 14 and 15). Such experiments identified the following small molecules (e.g., compounds) capable of targeting a MLL-fusion protein interaction site for DOT1L (e.g., the AF9/ENL interaction site for DOT1L) (e.g., a small molecule having binding properties similar to the region of DOT1L corresponding to DOT1L 865LPISIPLSTV874(SEQ ID NO:1)):
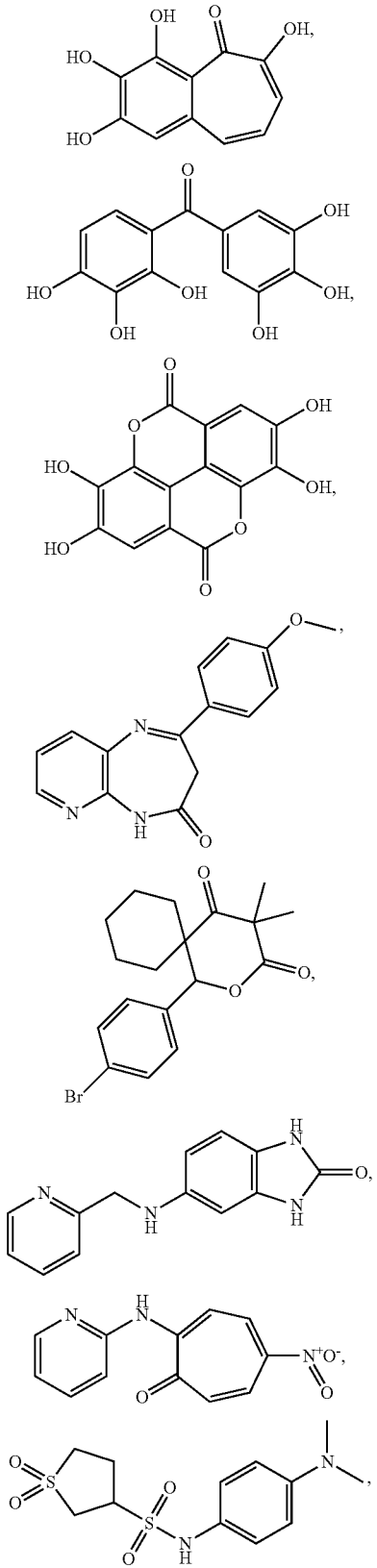
-continued
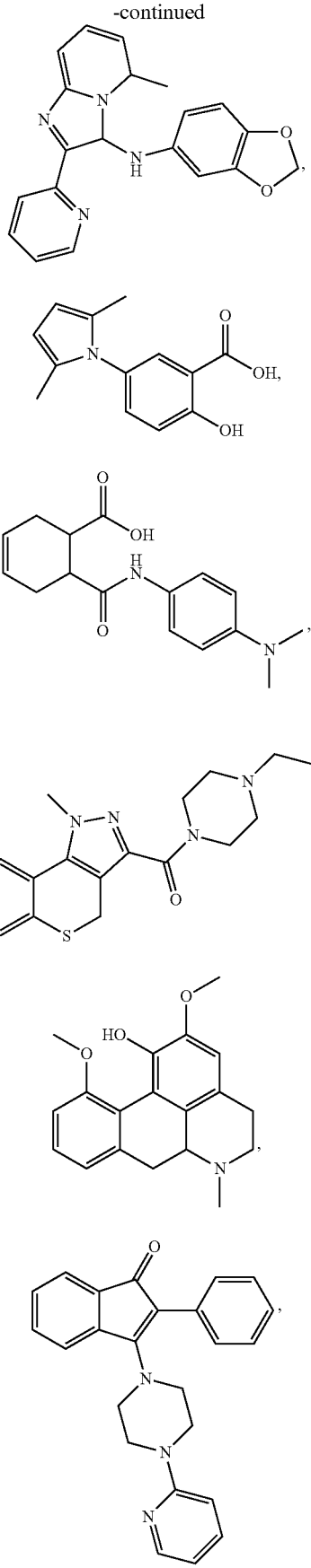

25
-continued
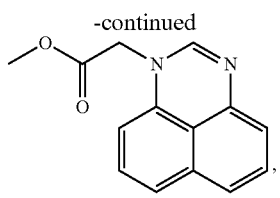
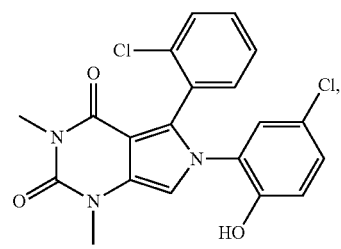
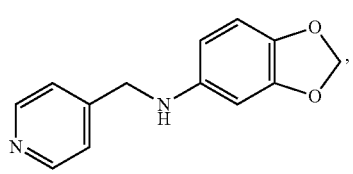
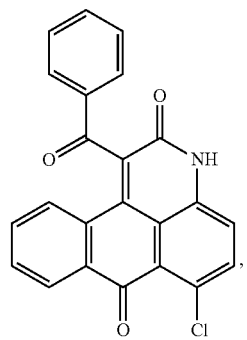
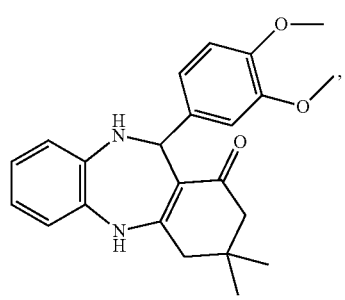
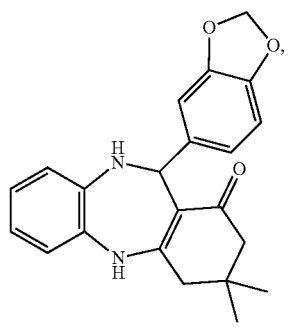
26
-continued
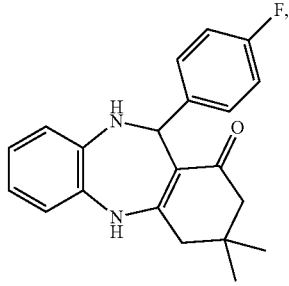
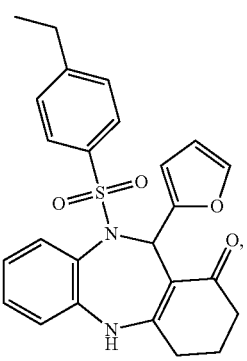
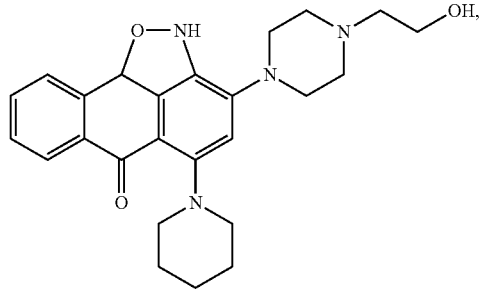
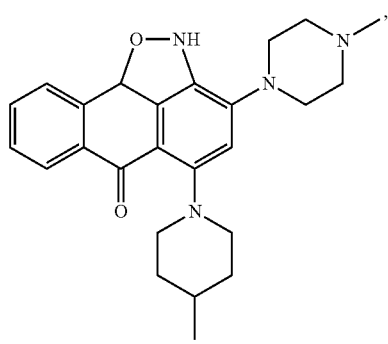
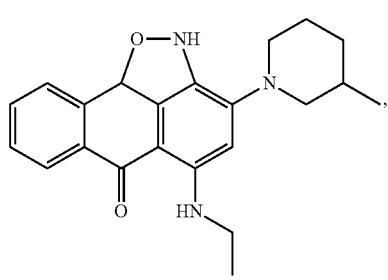

27
-continued
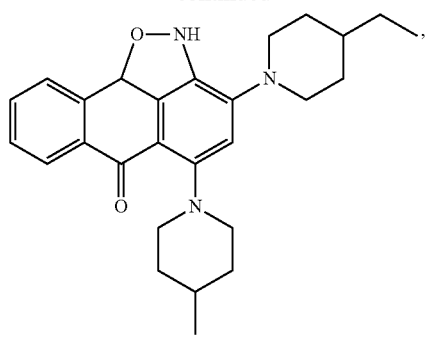
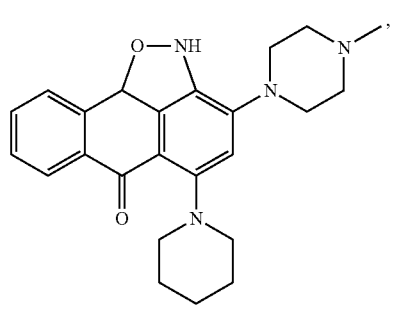
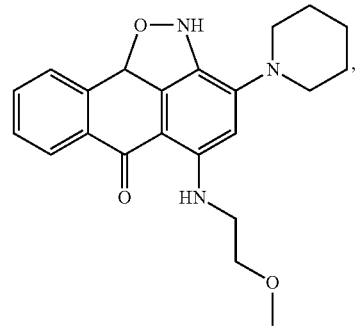
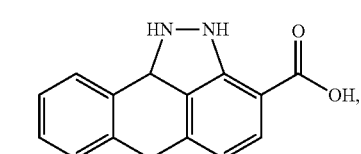
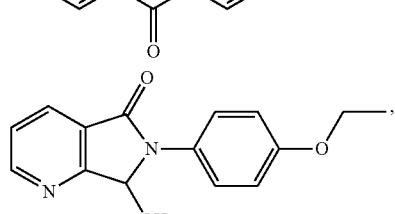
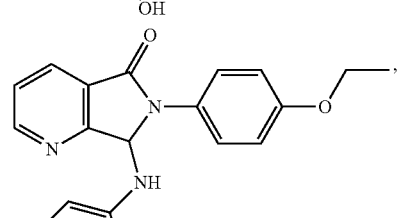
28
-continued
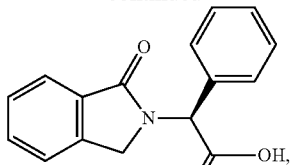
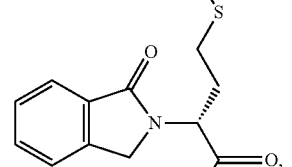
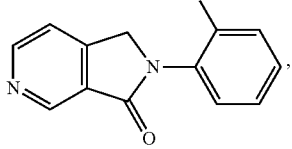
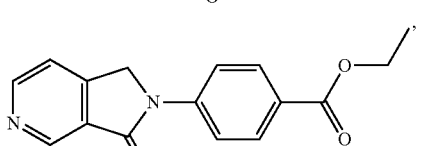
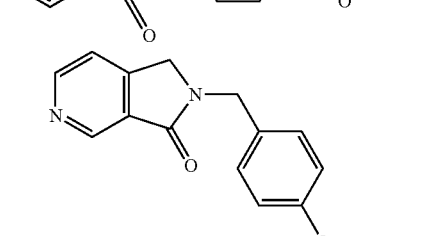
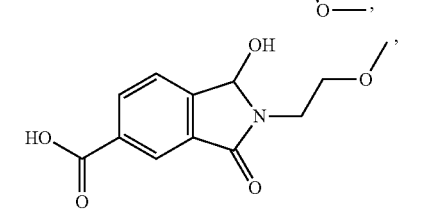
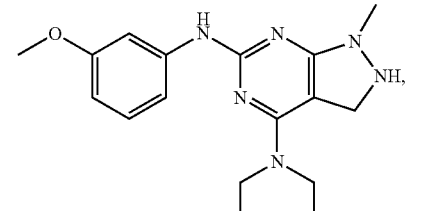
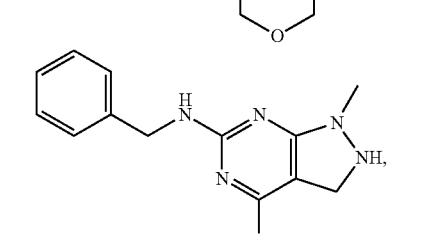

29

-continued

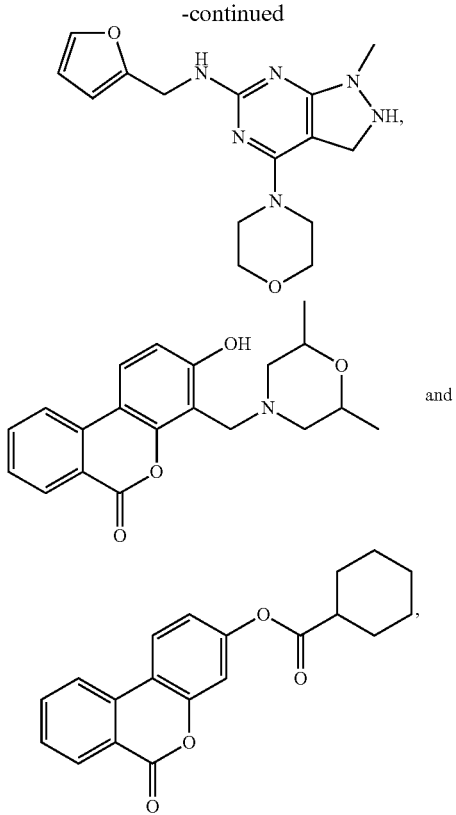

and including salts, esters, and prodrugs thereof, and including both R and S enantiomeric forms and racemic mixtures thereof.

III. Pharmaceutical Compositions, Formulations, and Exemplary Administration Routes and Dosing Considerations Exemplary embodiments of various contemplated medicaments and pharmaceutical compositions are provided below.

A. Preparing Medicaments

It is contemplated that the agents of the present invention are useful in the preparation of medicaments to treat a variety of conditions associated with MLL-fusion protein associated recruitment of DOT1L, and/or MLL-fusion protein associated leukemia.

In addition, it is contemplated that the agents are also useful for preparing medicaments for treating other disorders wherein the effectiveness of the compounds are known or predicted. The methods and techniques for preparing medicaments of an agent of the present invention are well-known in the art. Exemplary pharmaceutical formulations and routes of delivery are described below.

One of skill in the art will appreciate that any one or more of the agents described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the agents of the present invention are provided in unsolvated form or are in non-aqueous solutions (e.g., ethanol). The agents may be generated to allow such formulations through the production of specific crystalline polymorphs compatible with the formulations.

In certain embodiments, the present invention provides instructions for administering an agent to a subject. In certain embodiments, the present invention provides instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat a variety of disorders associated with MLL-fusion protein associated recruitment of DOT1L, and/or MLL-fusion protein associated leukemia.

C. Exemplary Administration Routes and Dosing Considerations

Various delivery systems are known and can be used to administer therapeutic agents (e.g., exemplary agents as described in Section II above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing a variety of conditions associated with MLL-fusion protein associated recruitment of DOT1L, and/or MLL-fusion protein associated leukemia. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent, the effective amount may be more or less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the agents described herein with one or more additional active agents. Indeed, it is a further aspect of this invention to provide methods for enhancing prior art therapies and/or pharmaceutical compositions by co-administering an agent of this invention. In co-administration procedures, the agents may be administered concurrently or sequentially. In one embodiment, the agents described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is associated with MLL-fusion protein associated recruitment of DOT1L, and/or MLL-fusion protein associated leukemia, the agent is known to treat cancer (e.g., leukemia) (e.g., MLL-fusion protein associated leukemia). A number of suitable therapeutic or anticancer agents are contemplated for use in the methods provided herein. Indeed, the methods provided herein can include but are not limited to, administration of numerous therapeutic agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods provided herein include one or more agents provided herein and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | |
|---|---|
| Aldesleukin (des-alanyl-1, serine-125 human interleukin-2) | Proleukin |
| Alemtuzumab (IgG1κ anti CD52 antibody) | Campath |
| Alitretinoin (9-cis-retinoic acid) | Panretin |
| Allopurinol (1,5-dihydro-4H-pyrazolo[3,4-d]pyrimidin-4-one monosodium salt) | Zyloprim |
| Altretamine (N,N,N',N',N",N",-hexamethyl-1,3,5-triazine-2,4,6-triamine) | Hexalen |
| Amifostine (ethanethiol, 2-[(3-aminopropyl)amino]-, dihydrogen phosphate (ester)) | Ethyol |
| Anastrozole (1,3-Benzenediacetonitrile,a,a,a',a'-tetramethyl-5-(1H-1,2,4-triazol-1-ylmethyl)) | Arimidex |
| Arsenic trioxide | Trisenox |
| Asparaginase (L-asparagine amidohydrolase, type EC-2) | Elspar |
| BCG Live (lyophilized preparation of an attenuated strain of *Mycobacterium bovis* (Bacillus Calmette-Gukin [BCG], substrain Montreal) | TICE BCG |
| bexarotene capsules (4-[1-(5,6,7,8-tetrahydro-3,5,5,8,8-pentamethyl-2-napthalenyl) ethenyl] benzoic acid) | Targretin |
| bexarotene gel | Targretin |
| Bleomycin (cytotoxic glycopeptide antibiotics produced by *Streptomyces verticillus*; bleomycin A$_2$ and bleomycin B$_2$) | Blenoxane |
| Capecitabine (5'-deoxy-5-fluoro-N-[(pentyloxy)carbonyl]-cytidine) | Xeloda |
| Carboplatin (platinum, diammine [1,1-cyclobutanedicarboxylato(2-)-0,0']-,(SP-4-2)) | Paraplatin |
| Carmustine (1,3-bis(2-chloroethyl)-1-nitrosourea) | BCNU, BiCNU |
| Carmustine with Polifeprosan 20 Implant | Gliadel Wafer |
| Celecoxib (as 4-[5-(4-methylphenyl)-3-(trifluoromethyl)-1H-pyrazol-1-yl] benzenesulfonamide) | Celebrex |
| Chlorambucil (4-[bis(2chlorethyl)amino]benzenebutanoic acid) | Leukeran |
| Cisplatin (PtCl$_2$H$_6$N$_2$) | Platinol |
| Cladribine (2-chloro-2'-deoxy-b-D-adenosine) | Leustatin, 2-CdA |
| Cyclophosphamide (2-[bis(2-chloroethyl)amino] tetrahydro-2H-13,2-oxazaphosphorine 2-oxide monohydrate) | Cytoxan, Neosar |
| Cytarabine (1-b-D-Arabinofuranosylcytosine, C$_9$H$_{13}$N$_3$O$_5$) | Cytosar-U |
| cytarabine liposomal | DepoCyt |
| Dacarbazine (5-(3,3-dimethyl-1-triazeno)-imidazole-4-carboxamide (DTIC)) | DTIC-Dome |
| Dactinomycin, actinomycin D (actinomycin produced by *Streptomyces parvullus*, C$_{62}$H$_{86}$N$_{12}$O$_{16}$) | Cosmegen |
| Darbepoetin alfa (recombinant peptide) | Aranesp |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome |

TABLE 1-continued

| | |
|---|---|
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine |
| Denileukin diftitox (recombinant peptide) | Ontak |
| Dexrazoxane ((S)-4,4'-(1-methyl-1,2-ethanediyl)bis-2,6-piperazinedione) | Zinecard |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex |
| doxorubicin | Adriamycin PFS Intravenous injection |
| doxorubicin liposomal | Doxil |
| dromostanolone propionate (17b-Hydroxy-2a-methyl-5a-androstan-3-one propionate) dromostanolone propionate | Dromostanolone Masterone injection |
| Elliott's B Solution | Elliott's B Solution |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence |
| Epoetin alfa (recombinant peptide) | Epogen |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt |
| Etoposide phosphate (4'-Demethylepipodophyllotoxin 9-[4,6-O-(R)-ethylidene-(beta)-D-glucopyranoside), 4'-(dihydrogen phosphate)) | Etopophos |
| etoposide, VP-16 (4'-demethylepipodophyllotoxin 9-[4,6-0-(R)-ethylidene-(beta)-D-glucopyranoside]) | Vepesid |
| Exemestane (6-methylenandrosta-1,4-diene-3,17-dione) | Aromasin |
| Filgrastim (r-metHuG-CSF) | Neupogen |
| floxuridine (intraarterial) (2'-deoxy-5-fluorouridine) | FUDR |
| Fludarabine (fluorinated nucleotide analog of the antiviral agent vidarabine, 9-b-D-arabinofuranosyladenine (ara-A)) | Fludara |
| Fluorouracil, 5-FU (5-fluoro-2,4(1H,3H)-pyrimidinedione) | Adrucil |
| Fulvestrant (7-alpha-[9-(4,4,5,5,5-penta fluoropentylsulphinyl) nonyl]estra-1,3,5-(10)-triene-3,17-beta-diol) | Faslodex |
| Gemcitabine (2'-deoxy-2',2'-difluorocytidine monohydrochloride (b-isomer)) | Gemzar |
| Gemtuzumab Ozogamicin (anti-CD33 hP67.6) | Mylotarg |
| Goserelin acetate | Zoladex Implant |
| Hydroxyurea | Hydrea |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-N-[2-bis(carboxymethyl)amino]-2-(methyl)-ethyl]glycine) | Zevalin |
| Idarubicin (5,12-Naphthacenedione,9-acetyl-7-[(3-amino-2.3,6-trideoxy-(alpha)-L-lyxo-hexopyranosyl)oxy]-7,8,9,10-tetrahydro-6,9,11-trihydroxyhydrochloride,(7S-cis)) | Idamycin |
| Ifosfamide (3-(2-chloroethyl)-2-[(2-chloroethyl)amino]tetrahydro-2H-1,3,2-oxazaphosphorine 2-oxide) | IFEX |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a (recombinant peptide) | Roferon-A |
| Interferon alfa-2b (recombinant peptide) | Intron A (Lyophilized Betaseron) |
| Irinotecan HCl ((4S)-4,11-diethyl-4-hydroxy-9-[(4-piperi-dinopiperidino)carbonyloxy]-1H-pyrano[3',4': 6,7] indolizino[1.2-b] quinoline-3,14(4H, 12H) dione hydrochloride trihydrate) | Camptosar |
| Letrozole (4,4'-(1H-1,2,4-Triazol-1-ylmethylene) dibenzonitrile) | Femara |
| Leucovorin (L-Glutamic acid, N[4[[(2amino-5-formyl],4,5,6,7,8-hexahydro4oxo6-pteridinyl)methyl]amino]benzoyl], calcium salt (1:1)) | Wellcovorin, Leucovorin |
| Levamisole HCl ((−)-(S)-2,3,5,6-tetrahydro-6-phenylimidazo [2,1-b] thiazole monohydrochloride $C_{11}H_{12}N_2S\cdot HCl$) | Ergamisol |
| Lomustine (1-(2-chloro-ethyl)-3-cyclohexyl-1-nitrosourea) | CeeNU |
| Mechlorethamine, nitrogen mustard (2-chloro-N-(2-chloroethyl)-N-methylethanamine hydrochloride) | Mustargen |
| Megestrol acetate 17α(acetyloxy)-6-methylpregna-4,6-diene-3,20-dione | Megace |
| Melphalan, L-PAM (4-[bis(2-chloroethyl) amino]-L-phenylalanine) | Alkeran |
| Mercaptopurine, 6-MP (1,7-dihydro-6H-purine-6-thione monohydrate) | Purinethol |
| Mesna (sodium 2-mercaptoethane sulfonate) | Mesnex |
| Methotrexate (N-[4-[[(2,4-diamino-6-pteridinyl)methyl]methylamino] benzoyl-L-glutamic acid) | Methotrexate |
| Methoxsalen (9-methoxy-7H-furo[3,2-g][1]-benzopyran-7-one) | Uvadex |
| Mitomycin C | Mutamycin |
| mitomycin C | Mitozytrex |
| Mitotane (1,1-dichloro-2-(o-chlorophenyl)-2-(p-chlorophenyl) ethane) | Lysodren |
| Mitoxantrone (1,4-dihydroxy-5,8-bis[[2-[(2-hydroxyethyl)amino] ethyl]amino]-9,10-anthracenedione dihydrochloride) | Novantrone |
| Nandrolone phenpropionate | Durabolin-50 |
| Nofetumomab | Verluma |
| Oprelvekin (IL-11) | Neumega |
| Oxaliplatin (cis-[(1R,2R)-1,2-cyclohexanediamine-N,N'] [oxalato(2-)-O,O'] platinum) | Eloxatin |
| Paclitaxel (5β,20-Epoxy-1,2a,4,7β,10β,13a-hexahydroxytax-11-en-9-one 4,10-diacetate 2-benzoate 13-ester with (2R, 3 S)-N-benzoyl-3-phenylisoserine) | TAXOL |
| Pamidronate (phosphonic acid (3-amino-1-hydroxypropylidene) bis-, disodium salt, pentahydrate, (APD)) | Aredia |
| Pegademase ((monomethoxypolyethylene glycol succinimidyl) 11-17-adenosine deaminase) | Adagen (Pegademase Bovine) |
| Pegaspargase (monomethoxypolyethylene glycol succinimidyl L-asparaginase) | Oncaspar |
| Pegfilgrastim (covalent conjugate of recombinant methionyl human G-CSF (Filgrastim) and monomethoxypolyethylene glycol) | Neulasta |
| Pentostatin | Nipent |
| Pipobroman | Vercyte |
| Plicamycin, Mithramycin (antibiotic produced by *Streptomyces plicatus*) | Mithracin |

TABLE 1-continued

| | |
|---|---|
| Porfimer sodium | Photofrin |
| Procarbazine<br>(N-isopropyl-μ-(2-methylhydrazino)-p-toluamide<br>monohydrochloride) | Matulane |
| Quinacrine<br>(6-chloro-9-(1-methyl-4-diethyl-amine) butylamino-2-<br>methoxyacridine) | Atabrine |
| Rasburicase<br>(recombinant peptide) | Elitek |
| Rituximab<br>(recombinant anti-CD20 antibody) | Rituxan |
| Sargramostim<br>(recombinant peptide) | Prokine |
| Streptozocin<br>(streptozocin 2-deoxy-2-[[(methylnitrosoamino)carbonyl]<br>amino]-a(and b)-D-glucopyranose and 220 mg citric acid<br>anhydrous) | Zanosar |
| Talc<br>($Mg_3Si_4O_{10}$ $(OH)_2$) | Sclerosol |
| Tamoxifen<br>((Z)2-[4-(1,2-diphenyl-1-butenyl) phenoxyl-N,N-<br>dimethylethanamine 2-hydroxy-1,2,3-<br>propanetricarboxylate (1:1)) | Nolvadex |
| Temozolomide<br>(3,4-dihydro-3-methyl-4-oxoimidazo[5,1-d]-as-tetrazine-<br>8-carboxamide) | Temodar |
| teniposide, VM-26<br>(4'-demethylepipodophyllotoxin 9-[4,6-0-(R)-2-<br>thenylidene-(beta)-D-glucopyranoside]) | Vumon |
| Testolactone<br>(13-hydroxy-3-oxo-13,17-secoandrosta-1,4-dien-17-oic<br>acid [dgr]-lactone) | Teslac |
| Thioguanine, 6-TG<br>(2-amino-1,7-dihydro-6H-purine-6-thione) | Thioguanine |
| Thiotepa<br>(Aziridine, 1,1',1''-phosphinothioylidynetris-, or Tris<br>(1-aziridinyl) phosphine sulfide) | Thioplex |
| Topotecan HCl<br>((S)-10-[(dimethylamino)methyl]-4-ethyl-4,9-dihydroxy-<br>1H-pyrano[3',4': 6,7] indolizino [1,2-b] quinoline-3,14-<br>(4H,12H)-dione monohydrochloride) | Hycamtin |
| Toremifene<br>(2-(p-[(Z)-4-chloro-1,2-diphenyl-1-butenyl]-phenoxy)-<br>N,N-dimethylethylamine citrate (1:1)) | Fareston |
| Tositumomab, I 131 Tositumomab<br>(recombinant murine immunotherapeutic monoclonal<br>$IgG_{2a}$ lambda anti-CD20 antibody (I 131 is a<br>radioimmunotherapeutic antibody)) | Bexxar |
| Trastuzumab<br>(recombinant monoclonal $IgG_1$ kappa anti-HER2 anti-<br>body) | Herceptin |
| Tretinoin, ATRA<br>(all-trans retinoic acid) | Vesanoid |
| Uracil Mustard | Uracil<br>Mustard<br>Capsules |
| Valrubicin, N-trifluoroacetyladriamycin-14-valerate<br>((2S-cis)-2-[1,2,3,4,6,11-hexahydro-2,5,12-trihydroxy-7<br>methoxy-6,11-dioxo-[[4 2,3,6-trideoxy-3-[(trifluoroacetyl)-<br>amino-α-L-lyxo-hexopyranosyl]oxyl]-2-naphthacenyl]-2-<br>oxoethyl pentanoate) | Valstar |
| Vinblastine, Leurocristine<br>($C_{46}H_{56}N_4O_{10}$•$H_2SO_4$) | Velban |
| Vincristine<br>($C_{46}H_{56}N_4O_{10}$•$H_2SO_4$) | Oncovin |
| Vinorelbine<br>(3',4'-didehydro-4'-deoxy-C'-norvincaleukoblastine [R-<br>(R*,R*)-2,3-dihydroxybutanedioate (1:2)(salt)]) | Navelbine |
| Zoledronate, Zoledronic acid<br>((1-Hydroxy-2-imidazol-1-yl-phosphonoethyl) phosphonic<br>acid monohydrate) | Zometa |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atra-senten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hul4.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC 1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments, methods provided herein comprise administering one or more agents provided herein with radiation therapy. The methods provided herein are not limited by the types, amounts, or delivery and administration systems used to deliver therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in therapeutic period. In one embodiment, radiation is initiated in week 1 or week 2, and is administered for the remaining duration of therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

In some embodiments of the methods provided herein, one or more agents provided herein and one or more therapeutic agents or anticancer agents are administered to an animal under one or more of the following conditions: at different periodicities, at different durations, at different concentrations, by different administration routes, etc. In some embodiments, the agent is administered prior to therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of therapeutic or anticancer agent. In some embodiments, the agent is administered after therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the agent and therapeutic or anticancer agent are administered concurrently but on different schedules, e.g., the agent is administered daily while therapeutic or anticancer agent is administered once a week, once every two weeks, once every three weeks, or once every four weeks. In other embodiments, the agent is administered once a week while therapeutic or anticancer agent is administered daily, once a week, once every two weeks, once every three weeks, or once every four weeks.

IV. Drug Screens

In some embodiments of the present invention, potential agents (e.g., peptides, small molecules, peptidomimetics, and/or cyclic peptides) are screened for their binding affinity to the MLL-fusion protein interaction site for DOT1L (e.g., the AF9/ENL interaction site for DOT1L). In particularly preferred embodiments, agents are selected for use in the methods of the present invention by measuring their biding affinity to the MLL-fusion protein interaction site for DOT1L (e.g., the AF9/ENL interaction site for DOT1L). In some embodiments, binding affinity screens are conducted in in vitro systems. In other embodiments, these screens are conducted in in vivo or ex vivo systems. In some embodiments, an optimized FP-based assay is used to screen agents that target the C-terminal domains of AF9 and ENL and block the DOT1L recruitment (see, e.g., Examples 12, 13, 14 and 15).

In some embodiments, agents of the present invention, and other potentially useful agents, are screened for an ability to displace agents bound to the C terminal domains of AF9/ENL. In some embodiments, agents of the present invention, and other potentially useful agents, are screened for an ability to displace fluorescent labeled DOT1L peptide (e.g., DOT1L 865LPISIPLSTV874(SEQ ID NO:1)) bound to the C terminal domains of AF9/ENL.

In some embodiments, potential agents (e.g., peptides, small molecules, peptidomimetics, and/or cyclic peptides) are screened for an ability to treat disorders associated with DOT1L binding with AF9/ENL (e.g., MLL-fusion protein associated leukemia) through binding the MLL-fusion protein interaction site for DOT1L (e.g., the AF9/ENL interaction site for DOT1L).

In some embodiments, structure-based virtual screening methodologies are contemplated for predicting the binding affinity of potential agents (e.g., peptides, small molecules, peptidomimetics, and/or cyclic peptides) with the MLL-fusion protein interaction site for DOT1L (e.g., the AF9/ENL interaction site for DOT1L). In some embodiments, small molecule structures are predicted from a molecular modeling software (e.g., MacroModel, MOE, Glide, Gold, Autodock, DOCK, Unity, Cerius2, Daylight, PipelinePilot, ChemAxon, Sprout, Hook, MCSS, AMBER, BOSS).

The present invention also provides methods of modifying and derivatizing the agents of the present invention to increase desirable properties (e.g., ability to bind the MLL-fusion protein interaction site for DOT1L (e.g., the AF9/ENL interaction site for DOT1L) or to minimize undesirable properties. The principles of chemical derivatization are well understood. In some embodiments, iterative design and chemical synthesis approaches are used to produce a library of derivatized child compounds from a parent compound.

V. Therapeutic Application

In certain embodiments, the present invention provides methods (e.g., therapeutic applications) for treating and/or preventing disorders related to MLL-fusion protein associated recruitment of DOT1L, and/or MLL-fusion protein associated leukemia. In some embodiments, the methods involve administering one or more agents (see, e.g., Section II- Exemplary Agents) of the present invention to a subject having a disorder related to MLL-fusion protein associated recruitment of DOT1L and/or MLL-fusion protein associated leukemia. In such embodiments, binding of the MLL-fusion protein interaction site for DOT1L (e.g., the AF9/ENL interaction site for DOT1L) (e.g., with an agent having binding properties similar to the region of DOT1L corresponding to DOT1L 865LPISIPLSTV874(SEQ ID NO:1)) modulates (e.g., inhibits) the binding of DOT1L with AF9/ENL, thereby inhibiting, for example, development of an AEP complex (e.g., wherein ENL associates with AF4, AF5q31, P-TEFb, and DOT1L), aberrant H3K79 methylation, and/or MLL-fusion protein associated leukemia. In some embodiments, modulation (e.g., inhibition) of the MLL-fusion protein interaction site for DOT1L (e.g., the AF9/ENL interaction site for DOT1L) is associated with a general reduction of symptoms associated with MLL-fusion protein associated leukemia.

The present invention also includes methods involving co-administration of the agents described herein with one or more additional active agents. Indeed, it is a further aspect of this invention to provide methods for enhancing prior art therapies and/or pharmaceutical compositions by co-administering a agent of this invention. In co-administration procedures, the agents may be administered concurrently or sequentially. In one embodiment, the agents described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is associated with MLL-fusion protein associated recruitment of DOT1L, and/or MLL-fusion protein associated leukemia, the agent is known to treat cancer (e.g., leukemia) (e.g., MLL-fusion protein associated leukemia) (e.g., any type of disorder related to MLL-fusion protein associated recruitment of DOT1L) (e.g., any type of cancer related to MLL-fusion protein associated recruitment of DOT1L).

EXPERIMENTAL

Example 1

Figure 14:
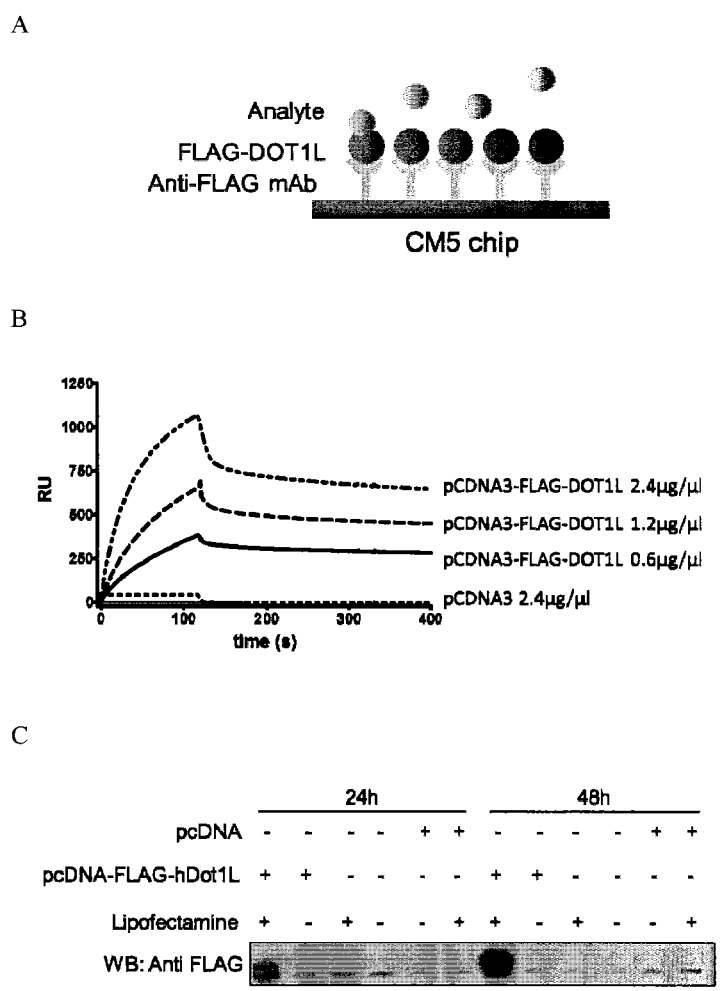
FIG. 14 shows immobilization of Flag-DOT1L protein on CM5 chip. (A) Schematic of capturing FLAG-DOT1L protein on anti-Flag antibody immobilized CM5 sensor chip. (B) Different concentrations of FLAG-DOT1L protein overexpressed 293 cell lystate injected over anti-FLAG antibody immobilized surface together with empty vector control to demonstrate the specificity of FLAG-DOT1L protein binding on the surface (C) Confirmation of the expression of FLAG-DOT1L protein in 293 cells by anti-FLAG immuno blotting.

This example shows that DOT1L binds MLL-fusion proteins, AF9 and ENL, through 10 residues in the C-terminal unstructured region. AF9 and ENL are two of the most common MLL fusion proteins (see, e.g., Daser A, Rabbitts T H (2004) Genes & development 18: 965-974) and belong to the YEATS protein family (see, e.g., Schulze J M, et al., (2009) Biochem Cell Biol 87: 65-75). Both of these two proteins consist of N-terminal YEATS domain and a C-terminal hydrophobic domain (see, e.g., Zhang W, et al., (2007) J Clin Invest 117: 773-783). AF9 and ENL shared high homology in the C-terminal domain and it had been shown that through this domain AF9/ENL are involved in the PPI which is crucial for MLL leukemia transformation (see, e.g., Dobson C L, et al., (1999) Embo J 18: 3564-3574; Mueller D, et al., (2007) Blood 110: 4445-4454; Yokoyama A, et al., (2010) Cancer cell 17: 198-212). The interaction of AF9 or ENL with DOT1L has been reported previously by co-immunoprecipitation and yeast 2-hybrid studies (see, e.g., Biswas D, et al., (2011) PNAS 108: 15751-15756; Yokoyama A, et al., (2010) Cancer cell 17: 198-212; Zhang W, et al., (2006) J Biol Chem 281: 18059-18068; Zhang W, et al., (2007) J Clin Invest 117: 773-783; Mueller D, et al., (2007) Blood 110: 4445-4454). However, there is a lack of detailed biochemical and biophysical characterization of this interaction. To understand the molecular basis of DOT1L interaction with MLL-fusion proteins, these PPIs were analyzed using surface plasma resonance (SPR). An SPR assay was developed to quantify the binding affinity between full length DOT1L protein and MLL-fusion proteins. For that purpose, the flag-tagged full length DOT1L protein was transiently transfected in HEK 293 cells and after 48 hours transfection the flag-tagged DOT1L protein was captured from the HEK 293 whole cell lysate on an anti-flag antibody-coated biosensor chip (FIG. 1B and FIG. 14). The recombinant C-terminal domain from human AF9 (residues 497-568) and the corresponding segment from ENL protein (residues 489-559) were cloned, expressed and purified for the biochemical binding studies (FIG. 1A). Using this system, it was determined that AF9 and ENL bind to the immobilized full length DOT1L with a dissociation constant ($K_d$) of 33±4 nM and 206±80 nM respectively, agreeing well with a 1:1 interaction model (FIG. 1B). For the first time these studies quantitatively determined the binding affinity of DOT1L to AF9 and ENL and confirmed that DOT1L directly interacts with AF9 and ENL and has about six folds higher affinity against AF9 in comparison with ENL.

The C-terminal unstructured region of DOT1L has been reported to be involved in the interaction with AF9 and ENL (see, e.g., Mueller D, et al., (2007) Blood 110: 4445-4454; Yokoyama A, et al., (2010) Cancer cell 17: 198-212). Therefore the DOT1L 826-1095 fragment was cloned and expressed, and the interaction of this recombinant protein with AF9/ENL studied. SPR analysis showed that this segment of the DOT1L protein has $K_d$ values of 111 nM and 238 nM to AF9 and ENL protein respectively, which are similar to that of the full length DOT1L (FIG. 1C), confirming that this region in DOT1L protein is essential for interactions with AF9/ENL proteins.

Figure 2:
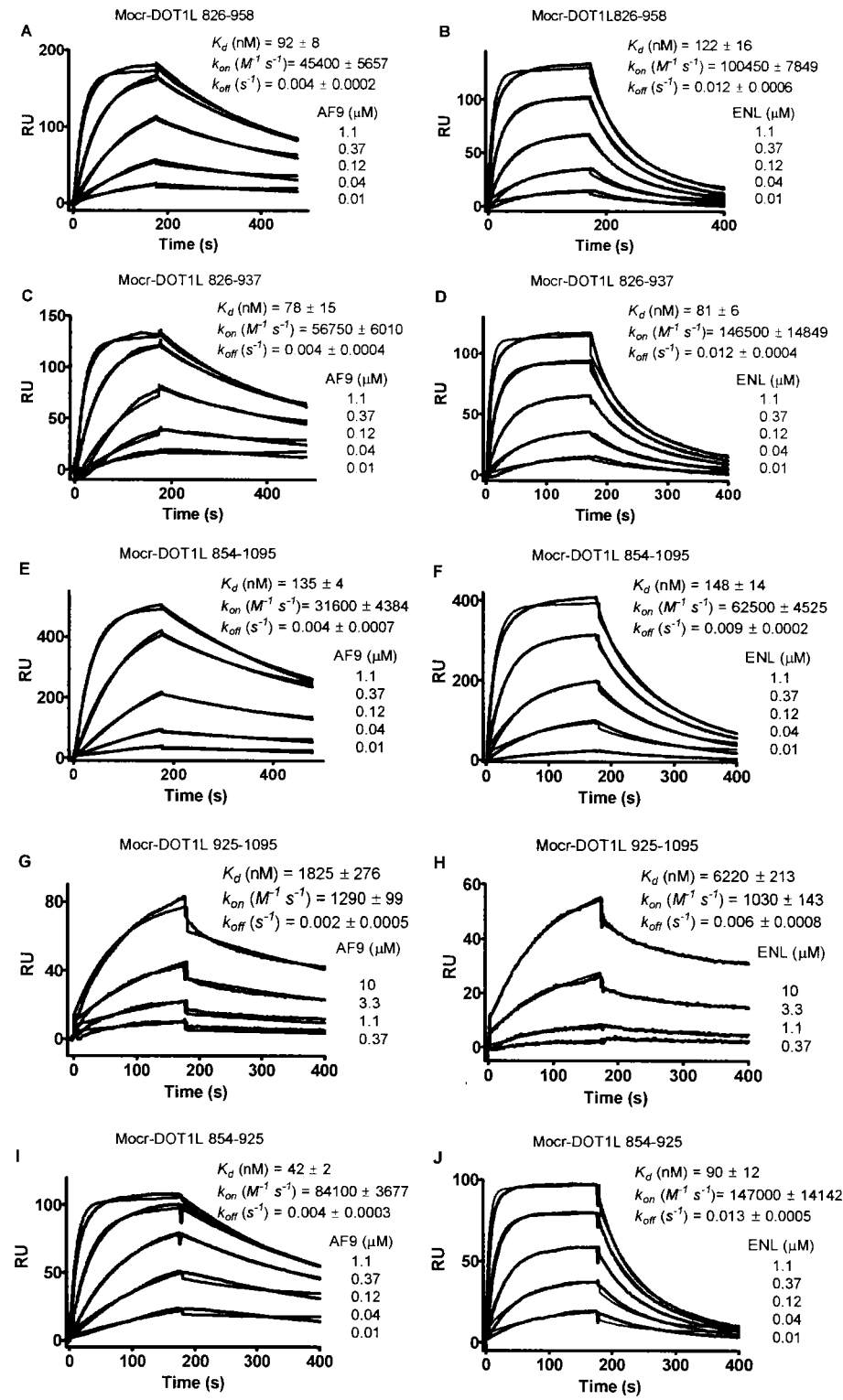
FIG. 2 shows sensorgrams representing the concentration-dependent binding of AF9(497-568) (FIG. 2A, 2C, 2E, 2G, and 2I) and ENL (489-559) (FIG. 2B, 2D, 2F, 2H, and 2J) proteins tested with a series of truncated constructs of DOT1 L immobilized on a CM5 sensor chip.

To further map the minimum region of DOT1L that is involved in the AF9/ENL interaction, a series of truncated constructs of DOT1L (826-1095), devised according to predicted stability, were designed, cloned, expressed and tested for their binding to AF9 and ENL (see, Table 2, FIG. 1A, FIG. 2). The SPR studies show that truncations of the DOT1L protein on the N-terminal site up to 854 residue and C-terminal deletions up to 937 residues didn't affected the interactions with AF9 and ENL and the obtained binding affinities were in a similar range. However, further deletion of the N-terminus and testing the N-terminus truncated DOT1L construct, starting from 925 to 1095 residue, showed significantly, thirty to fifty folds, decreased binding affinity to ENL and AF9 respectively clearly demonstrating the importance of the sequence 854 to 925 for the binding to MLL fusion proteins. Based on this result and the fact that the DOT1L (854-1095) binds with similar binding affinity as the full length DOT1L protein, the DOT1L construct (854-925) was cloned, expressed, purified, and tested. Consistent with the prediction, the interaction between this shortest fragment from DOT1L (854-925), having 72 amino acids, showed similar binding affinity to AF9 and ENL as the full length DOT1L with $K_d$ values of 42 nM and 90 nM, respectively (Table 2). These results confirm that, for example, DOT1L (854-925) contains a domain that interacts specifically with MLL-fusion proteins, AF9 and ENL.

TABLE 2

Binding affinities of AF9 and ENL proteins to full length DOT1L and different constructs of DOT1L immobilized on a CM5 sensor chip and determined by SPR

| Recombinant Immobilized Proteins (residues) | AF9 (497-568) $K_d \pm SD$ [nM] | ENL (489-559) $K_d \pm SD$ [nM] |
| --- | --- | --- |
| DOT1L (1-1537)* | 33 ± 4 | 206 ± 80 |
| DOT1L (826-1095) | 111 ± 10 | 238 ± 72 |
| DOT1L (826-958) | 92 ± 8 | 122 ± 16 |
| DOT1L (826-937) | 78 ± 15 | 81 ± 6 |
| DOT1L (854-1095) | 135 ± 4 | 148 ± 14 |
| DOT1L (925-1095) | 1,825 ± 276 | 6,220 ± 113 |
| DOT1L (854-925) | 42 ± 2 | 90 ± 12 |

*This is Flag-tagged full length human DOT1L protein.

Example 2

Figure 3:
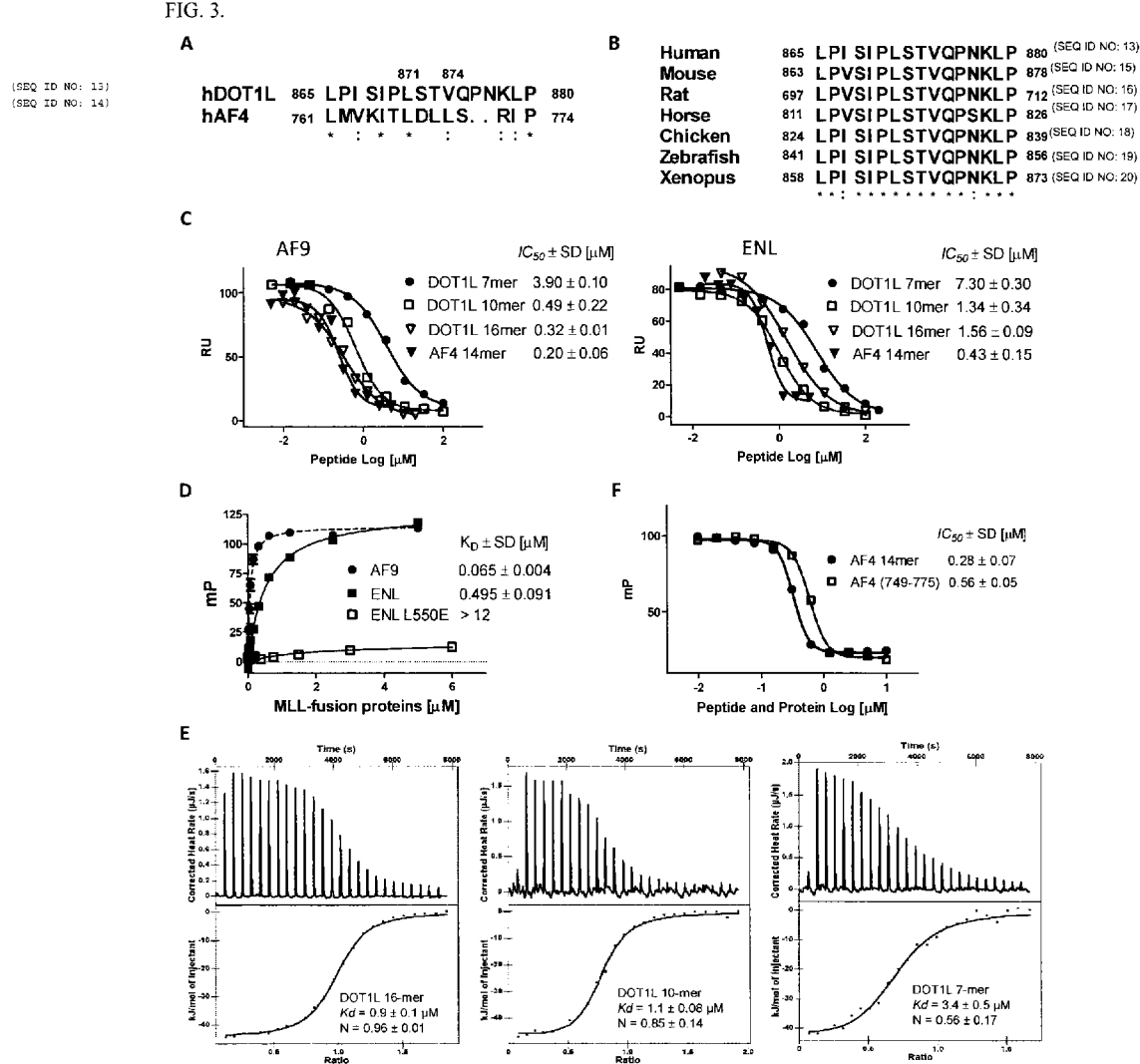
FIG. 3 describes mapping of the AF9/ENL binding site in DOT1L protein. A. Alignment of human DOT1L (865-880) with human AF4 (761-774). The conserved residues are marked with asterisk, and the similar amino acids with dots. B. Alignment of the identified AF9/ENL binding site in DOT1L protein from different species. C. SPR competitive binding curves of DOT1L 16 mer, 10 mer, 7 mer and AF4 14 mer peptides against AF9(497-568) and ENL (489-559) proteins running different tested concentrations over CM5 chip with immobilized DOT1L (826-1095). D. Binding affinity of fluorescent-labeled DOT1L 10-mer peptide against AF9, ENL and mutated ENL L550E. E. Isothermal titration calorimetry (ITC) of MBP-ENL (489-559) (80 µM) with a solution of DOT1L 16-mer (400 µM) and 10-mer (400 µM), and for DOT1L 7-mer peptide (500 µM) it was used 110 ipM MBP-ENL. For all titrations, the raw data are shown in the upper panel, and the integrated heat data, are shown in the lower panel. F. Fluorescence polarization (FP) competitive binding curves of AF4(749-775) recombinant protein and AF4 14 mer peptide using fluorescein-labeled DOT1L 10 mer peptide.
Figure 4:
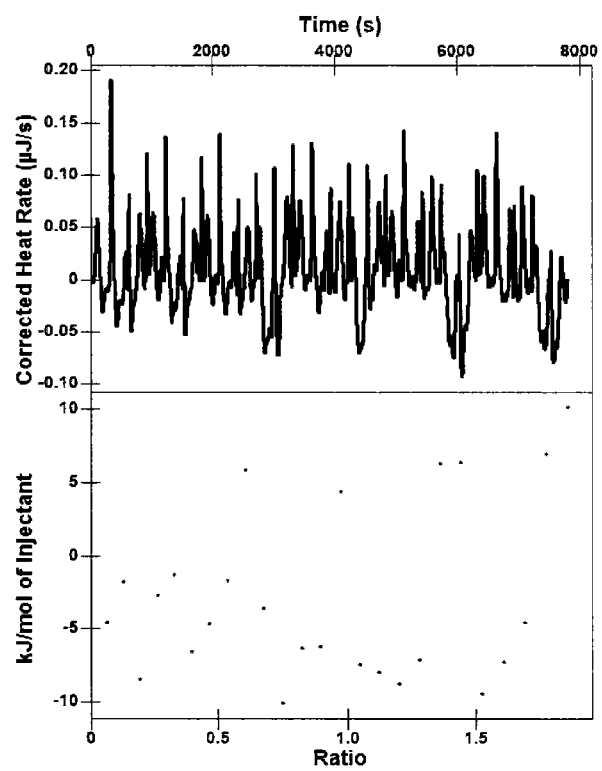
FIG. 4 describes isothermal titration calorimetry (ITC) of MBP tag only (80 µM) with a solution of DOT1L 16-mer (400 µM). The raw data are shown in the upper panel, and the integrated heat data are shown in the lower panel.

This example describes identification of a conserved peptide motif in DOT1L essential for binding AF9/ENL. It is known that the C-terminal hydrophobic AF9/ENL domains in MLL-fusions retain the ability to form independently higher order complexes with AF4/p-TEFb and with DOT1L, demonstrating that the associations of AF9/ENL with AF4 and DOT1L are mutually exclusive (see, e.g., Biswas D, et al., (2011) PNAS 108: 15751-15756; Yokoyama A, et al., (2010) Cancer cell 17: 198-212). The AF9-binding domain of AF4 is already mapped and identified interaction domain is conserved among the AF4 homologs (see, e.g., Srinivasan R S, et al., (2004) Leukemia: official journal of the Leukemia Society of America, Leukemia Research Fund, UK 18: 1364-1372). Based on these findings it was predicted that the AF9/ENL interacting site in DOT1L might share certain similarity to AF4 protein. By aligning the minimum amino acid sequence of DOT1L (854-925) involved in AF9/ENL interactions, with the AF9-binding domain of AF4 (761-774), a small 16-residue region in DOT1L (865-880) was identified to share high homology with AF4, consisting of four conserved and four similar residues (FIG. 3A). Importantly, alignment of DOT1L from different species demonstrate that this fragment is highly conserved (FIG. 3B). Based on this result two peptides, DOT1L-10 mer (865-874) and DOT1L-16 mer (865-880), were synthesized and whether the conserved peptide motif is sufficient for interaction with AF9 and ENL examined, using several binding assays, SPR, fluorescence polarization (FP), and isothermal titration calorimetry (ITC). Applying a competitive SPR assay, the ability of 16-mer and 10-mer synthetic peptides to inhibit the PPI between DOT1L and AF9 or ENL was tested. The obtained results demonstrate that both peptides can block the PPI between DOT1L/AF9 and DOT1L/ENL with similar IC$_{50}$ values of 0.49 μM and 0.32 μM respectively, against AF9, and 1.34 μM and 1.56 μM respectively, against ENL (FIG. 3C). Next the fluorescent labeled DOT1L 10-mer peptide was tested and notably, the peptide binds to MLL fusion proteins, AF9 and ENL, with $K_D$ values of 0.065 μM and 0.495 μM respectively (FIG. 3D). To further confirm the binding results, ITC assay was employed using MBP-tagged ENL protein (FIG. 3E). Both peptides, DOT1L 16-mer and 10-mer, bind to the ENL protein with similar binding affinity with $K_D$ values of 0.9 μM and 1.1 μM, respectively in 1:1 stoichiometry consistent with FP based results. To verify the specificity of this interaction, DOT1L 16-mer was also tested for its binding to the MBP tag only and did not show any binding (FIG. 4). The obtained binding results for DOT1L 16-mer and 10-mer peptides are consistent with the direct binding studies of the PPI (Table 2) and provide strong evidence that identified peptide motif in DOT1L is both required and sufficient for interaction with AF9 and ENL.

Since the identified DOT1L peptide shows sequence homology with the reported AF4 peptide, and the associations of AF9 and ENL with AF4 and DOT1L through their conserved C-terminal domain reportedly are mutually exclusive (see, e.g., Biswas D, et al., (2011) PNAS 108: 15751-15756; Yokoyama A, et al., (2010) Cancer cell 17: 198-212), competition experiments were carried out between DOT1L and AF4 for binding to MLL-fusion proteins. For this purpose AF4 recombinant protein (749-775 residues) were expressed and purified, and the AF4 14-mer peptide (761-774) synthesized (see, e.g., Srinivasan, R. S., et al., (2004) Leukemia 18, 1364-1372). As was expected, it was found that the recombinant AF4 protein and AF4 14 mer peptide efficiently competed away the binding of DOT1L 10-mer fluorescein-labeled peptide to the C-terminal domain of AF9 protein with similar IC$_{50}$ values of 0.56 and 0.28 μM (FIG. 3F). The SPR solution competitive binding assay confirmed these results and showed that the AF4 14 mer peptide is also able to inhibit the PPI between AF9-DOT1L and ENL-DOT1L, with similar potency as DOT1L 16-mer and 10-mer peptides, showing IC$_{50}$ of 0.20 μM against AF9 and 0.43 μM against ENL (FIG. 3C). These findings clearly demonstrate that DOT1L and AF4 bind with similar binding affinity and compete for the same AF9/ENL interaction site, the C-terminal hydrophobic domain.

Example 3

Figure 5:
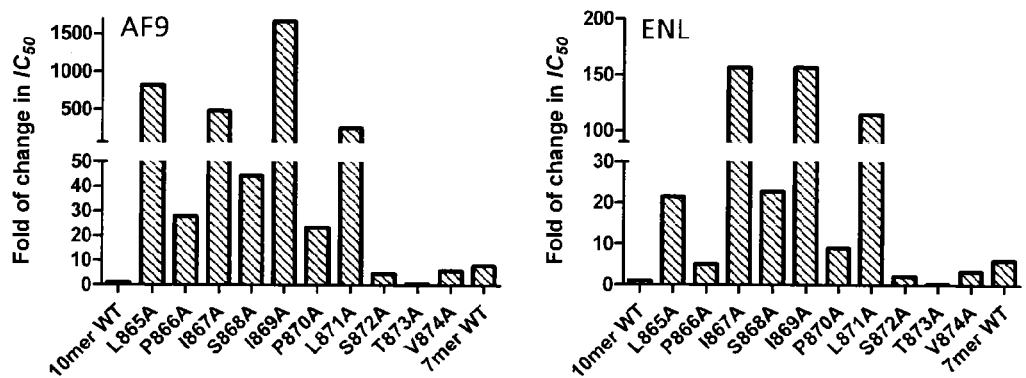
FIG. 5 pertains to characterizing the DOT1L 10-mer peptide and its interactions with MLL-fusion proteins. A. Binding affinities of alanine mutated DOT1L 10-mer peptides to AF9 and ENL in comparison to the wild type DOT1L 10-mer peptide. Peptide sequences and $IC_{50}$ values are provided (Table 3 and FIG. 6). B. Circular dichroism spectra of DOT1 L 16-mer and 10-mer peptides.
Figure 5:
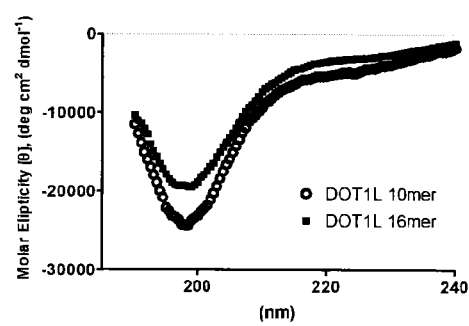
Figure 6:
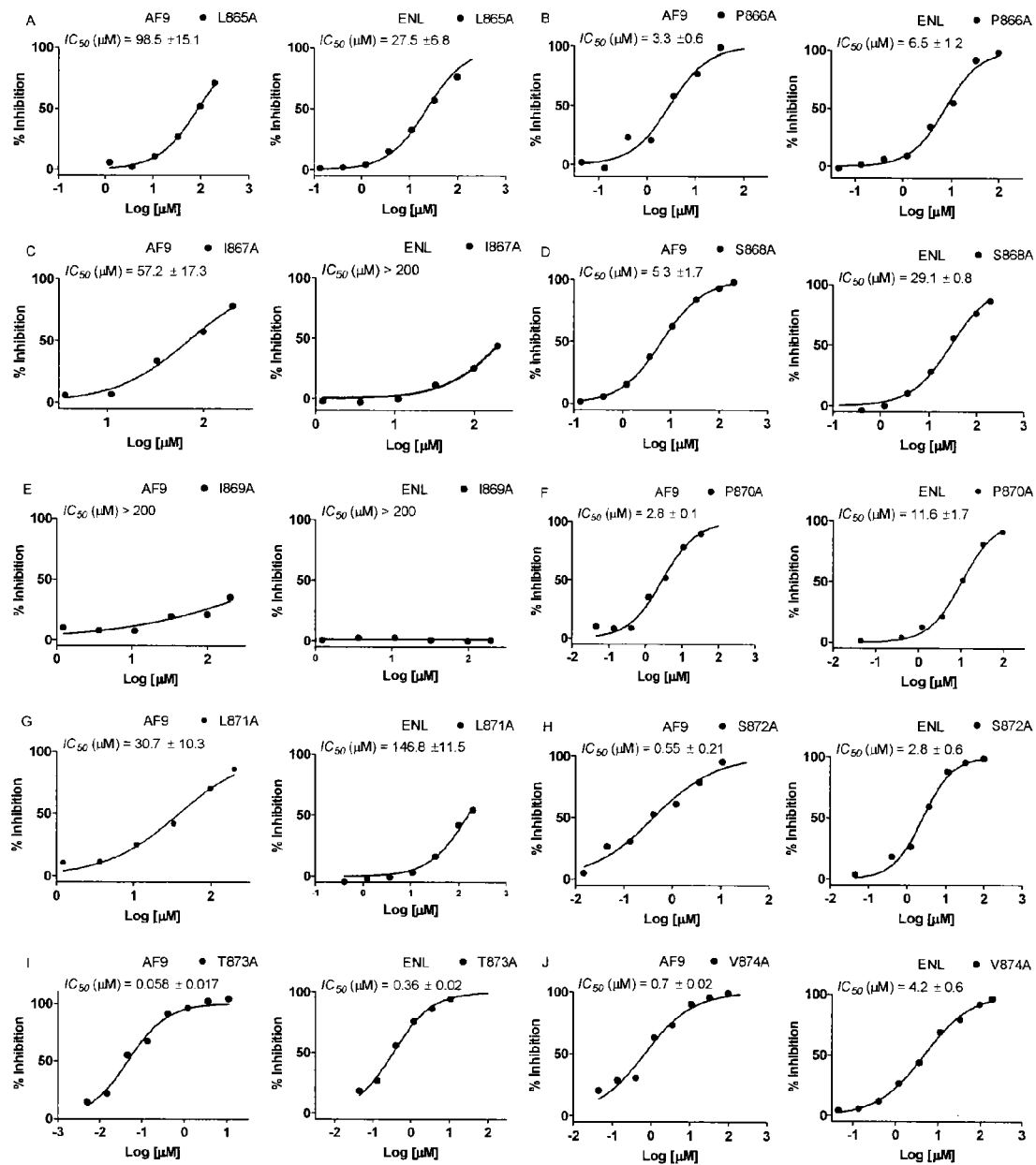
FIG. 6 shows SPR based competitive inhibition curves of DOT1 L 10mer alanine mutated peptides against AF9-DOT1 L or ENL -DOT1 L interactions for the following mutated DOT1 L peptides: L865A (FIG. 6A), P866A (FIG. 6B), 1867A (FIG. 6C), S868A (FIG. 6D), 1869A (FIG. 6E), P870A (FIG. 6F), L871A (FIG. 6G), S872A (FIG. 6H), T873A (FIG. 6I), and V874A (FIG. 6J).

This example describes Alanine-scanning mutagenesis studies of the interaction between DOT1L 10 mer peptide and MLL-fusion proteins. Alanine-scanning mutagenesis can yield important functional insight about PPI for which there is no structural information. Therefore, systematic alanine mutagenesis was performed to identify positions in DOT1L that make essential contacts to MLL-fusion proteins, AF9 and ENL. The DOT1L residues were mutated from Leu865 to Val874 to alanine, thus creating 10 different DOT1L mutants and determined their potency to inhibit the PPI in SPR-based competitive assay. Using wild type DOT1L-10-mer peptide as a standard, the binding affinities of each of these ten alanine mutated DOT1L-based peptides were compared (FIG. 5A, Table 3, and FIG. 6). The three conserved residues in DOT1L, L865, I869 and L871, as well as the similar residue, I867, failed to tolerate alanine substitution, with a significant decrease in binding affinity to both AF9 and ENL proteins. These results demonstrate the importance of the hydrophobic interactions which is consistent with notion of a conserved C-terminal hydrophobic domain in both AF9 and ENL. The un-conserved residues, P866, S868 and P870 had from 10 to 40 fold reductions in their ability to inhibit the PPI. Interestingly, mutation of the last three residues in the DOT1L-10-mer peptide, S872, T873 and V874 was well tolerated and showed only two to six-fold decrease in the binding affinity compared to the wild type peptide. Wild type 7-mer DOT1L peptide (865-871) was synthesized and tested its binding to AF9 and ENL. Consistent with the mutation data this peptide showed eight fold reduction in the binding to AF9 and fivefold reduction in binding affinity to ENL protein in comparison with the 10-mer peptide (FIGS. 3C and 5A). The binding affinity of DOT1L 7-mer peptide to ENL protein was confirmed in ITC assay showing $K_D$ of 3.4 µM, three fold lower in comparison with the 16-mer and 10-mer DOT1L peptides (FIG. 3E). Therefore, the alanine scanning mutagenesis studies indicate that the heptapeptide binding motif of DOT1L is essential for interactions with MLL-fusion proteins and is the minimum required fragment. In addition, the obtained results show a similar pattern in the binding of all tested peptides against AF9 and ENL proteins, suggesting that they share similar structural requirements for this interaction and a single amino acid mutation of the hydrophobic conserved residues is sufficient to disrupt the PPI. The role of the secondary structure of DOT1L peptides was investigated in order to further understand the interactions between DOT1L peptide and MLL-fusion proteins. For this purpose CD experiments were performed and DOT1L 16-mer and 10-mer peptides were tested. The obtained results showed that both peptides have unordered (random-coil) secondary structure (FIG. 5B). Overall, these findings provide a rationale towards future efforts in identifying chemical probes that can disrupt the interaction between DOT1L and the MLL-fusion proteins.

TABLE 3

Peptide sequence and $IC_{50}$ values of wild type and alanine mutated DOT1L peptides against AF9 and ENL proteins obtained by competitive SPR based assay using CM5 chip with immobilized DOT1L protein.

| Peptide | Sequence | $IC_{50}$ ± SD [µm] AF9 | ENL |
|---|---|---|---|
| DOT1L 10mer | Ac-LPISIPLSTV-NH$_2$ (a.a. 865-874) (SEQ ID NO: 1) | 0.49 ± 0.22 | 1.34 ± 0.34 |
| L865A | Ac-<u>A</u>PISIPLSTV-NH$_2$ (SEQ ID NO: 2) | 98.5 ± 15.1 | 27.5 ± 6.8 |
| P866A | Ac-L<u>A</u>ISIPLSTV-NH$_2$ (SEQ ID NO: 3) | 3.3 ± 0.6 | 6.5 ± 1.2 |
| I867A | Ac-LP<u>A</u>SIPLSTV-NH$_2$ (SEQ ID NO: 4) | 57.2 ± 17.3 | >200 |
| S868A | Ac-LPI<u>A</u>IPLSTV-NH$_2$ (SEQ ID NO: 5) | 5.3 ± 1.7 | 29.1 ± 0.8 |
| I869A | Ac-LPIS<u>A</u>PLSTV-NH$_2$ (SEQ ID NO: 6) | >200 | >200 |
| P870A | Ac-LPISI<u>A</u>LSTV-NH$_2$ (SEQ ID NO: 7) | 2.8 ± 0.1 | 11.6 ± 1.7 |
| L871A | Ac-LPISIP<u>A</u>STV-NH$_2$ (SEQ ID NO: 8) | 30.7 ± 10.3 | 146.8 ± 11.5 |
| S872A | Ac-LPISIPL<u>A</u>TV-NH$_2$ (SEQ ID NO: 9) | 0.55 ± 0.21 | 2.8 ± 0.6 |
| T873A | Ac-LPISIPLS<u>A</u>V-NH$_2$ (SEQ ID NO: 10) | 0.058 ± 0.017 | 0.36 ± 0.02 |
| V874A | Ac-LPISIPLST<u>A</u>-NH$_2$ (SEQ ID NO: 11) | 0.7 ± 0.02 | 4.2 ± 0.6 |
| DOT1L 7 mer | Ac-LPISIPL-NH$_2$ (SEQ ID NO: 12) | 3.9 ± 0.1 | 7.3 ± 0.3 |
| DOT1L 16 mer | Ac-LPISIPLSTVQPNKLP-NH$_2$ (a.a. 865-880) (SEQ ID NO: 13) | 0.32 ± 0.01 | 1.56 ± 0.09 |
| AF4 14 mer | Ac-LMVKITLDLLSRIP-NH$_2$ (a.a. 760-773) (SEQ ID NO: 14) | 0.20 ± 0.06 | 0.43 ± 0.15 |

Example 4

Figure 7:
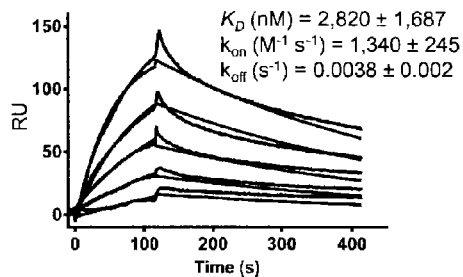
FIG. 7 pertains to analyzing the C-terminal domain in ENL protein and its binding to DOT1L. A. Alignment of ENL and AF9 C-terminal domain. The predicted α-helices are marked with Helix 1 and Helix 2 and conserved residues are presented in grey. B. Binding sensorgrams of immobilized Mocr-DOT1L (826-1095) with ENL H1(489-544) and ENL H2 (523-559), tested in concentration range from 1 to 16 µM and 5 to 35 µM, respectively. The $k_{on}$, $k_{off}$ and $K_d$ were calculated by simultaneous non-linear regression using 1:1 binding model and BIAevaluation 3.1 software. The experimental data are shown in black while the global fit analyses are shown in grey.
Figure 7:
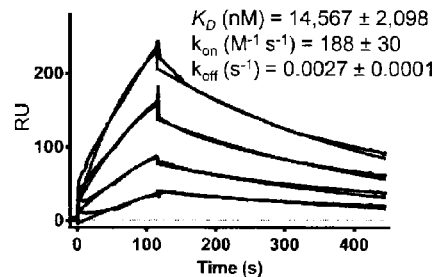
Figure 8:
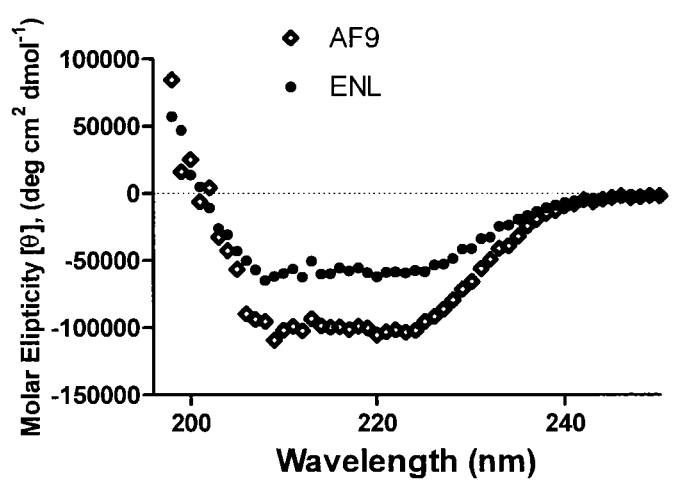
FIG. 8 shows circular dichroism spectra of C-terminal domain of AF9 (497-568) and ENL (489-559) proteins.

This example shows that the intact homology C-terminal hydrophobic domain of AF9 and ENL is required for the interaction with DOT1L. Secondary structure predictions of the C-terminal hydrophobic domain in AF9 and ENL indicate the presence of two highly conserved helical segments (FIG. 7A). Deleting either of these helical regions completely abrogated the transforming activity of MLL-AF9 and MLL-ENL fusion proteins (see, e.g., Slany R K, et al., Mol Cell Biol 18: 122-129). Using circular dichroism (CD) analysis of the AF9 and ENL recombinant proteins, it was determined that they were 94% and 61% helical, respectively, as was predicted (FIG. 8). To determine if the helical regions are important for the binding of these two MLL-fusion proteins to DOT1L, two recombinant fragments of ENL protein were prepared, ENL H1 (489-544) and ENL H2 (523-559), which correspond to predicted helices 1 and 2, respectively (see, e.g., Slany R K, et al., Mol Cell Biol 18: 122-129). It was determined that ENL H1 binds to DOT1L (826-1095) with $K_D$ of 2.8 µM and ENL H2 binds with $K_D$ of 14.6 µM (FIG. 7B), demonstrating ten-fold and thirty fold decreased binding affinity respectively in comparison with the intact ENL C-terminal domain (Table 1). These results clearly demonstrate that the entire C-terminal domain from ENL is required for optimal interaction with DOT1L, which is consistent with the reports that both helical segments are essential for the transformation potential of MLL-ENL fusion protein.

To further map and determined the residues in C-terminal domain of ENL that are essential for the interaction with DOT1L (so called "hot-spots"), an ENL mutant, L550E (FIG. 7A), was prepared which was reported to block the transforming capacity of MLL-ENL fusion protein (see, e.g., Yokoyama, A., et al., (2010) Cancer cell 17, 198-212). As was predicted the fluorescein-labeled DOT1L 10-mer peptide did not show binding to this mutant protein (FIG. 3D). The obtained result identified this conserved residue, L550 and L558 in ENL and AF9, respectively, as a hot-spot and demonstrated that is essential for the interaction with DOT1L.

Example 5

Figure 9:
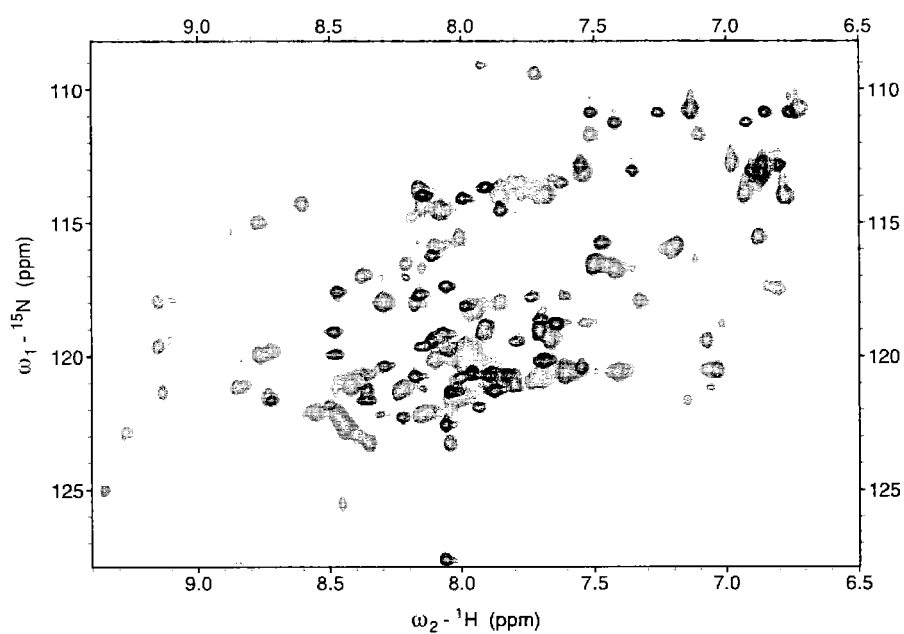
FIG. 9 shows binding of DOT1L to ENL C-terminal domain induces folding of ENL. A. Overlay of $^1H$-$^{15}N$ HSQC spectrum from $^{15}N$ ENL (489-559) (80 µM, black) and $^{15}N$ ENL (489-559) in complex with DOT1L (826-1095) protein in 1:1 molar ratio (grey) B. Overlay of $^1H$-$^{15}N$ HSQC spectrum from $^{15}N$ ENL (489-559) (80 µM, black) and $^{15}N$ ENL (489-559) in complex with DOT1L 16-mer peptide (darkest grey) or DOT1L 10-mer peptide (mid shape of grey between darkest and lightest) or DOT1L 7-mer peptide (lightest grey) in 1:1 molar ratio.
Figure 9:
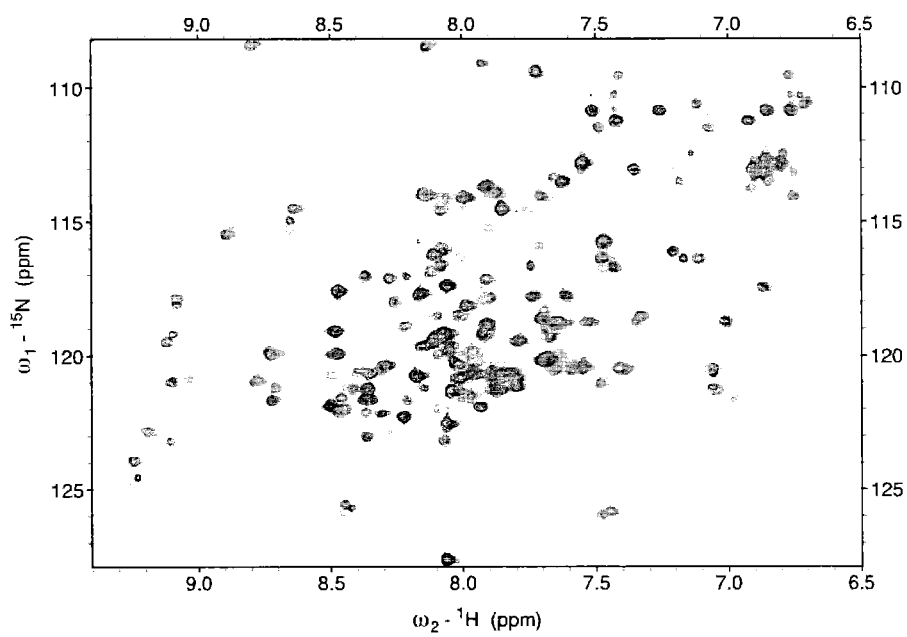

This example describes how binding of DOT1L to ENL C-terminus domain induces folding of ENL. To gain more information and understanding of the DOT1L-ENL PPI on the structural level, and to conclusively determine whether DOT1L peptides specifically interact with ENL, NMR spectroscopy was used. High-quality HSQC spectra of $^{15}$N-labeled ENL (489-559) protein was obtained. The $^{1}$H-$^{15}$N HSQC spectra of $^{15}$N-labeled ENL (489-559) protein alone showed poor signal dispersion, indicating that the protein, on its own is intrinsically disordered, i.e. unstructured (black spectrum in FIG. 9A). However, addition of the DOT1L protein (826-1095) (grey spectrum) in a 1:1 ratio resulted in folding and binding, and the spectrum of the ENL-DOT1L complex shows very extensive chemical shift dispersion consistent with a well folded and stable structure (FIG. 9A). Comparing the HSQC NMR spectra of DOT1L-ENL complex with the complexes with DOT1L 16-mer (darkest grey spectrum), 10-mer peptide (mid grey between darkest and lightest spectrum) and 7-mer peptide (lightest grey spectrum) (FIG. 9B), very similar chemical shifts can be observed and overall the HSQC spectrum of the ENL-DOT1L peptide complexes overlap with the spectrum of the complex with DOT1L protein. These results further confirm that all three peptides are able to completely recapitulate the chemical shifts of DOT1L protein, confirming that they bind in a similar way. Consistent with the binding results, NMR data further demonstrate that all tested DOT1L peptides interact directly with ENL and the heptapeptide binding motif of DOT1L is essential for these interactions and represents the minimum required motif.

Example 6

Figure 10:
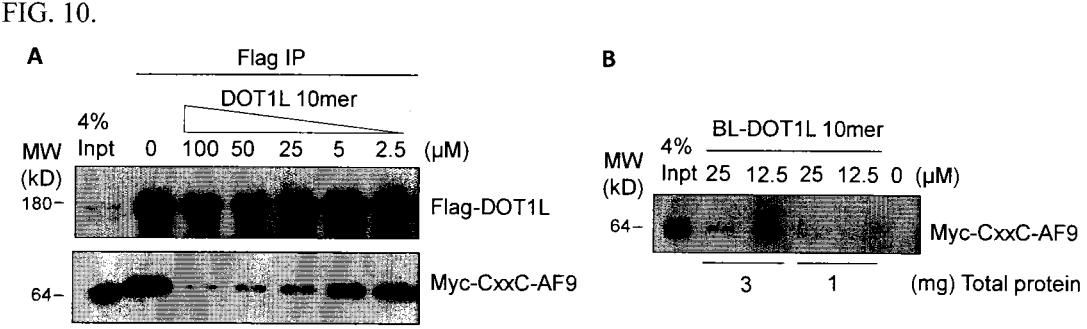
FIG. 10 shows DOT1L 10-mer peptide binds cellular MLL-AF9 fusion protein and disrupts its interaction with DOT1L. A. DOT1L 10-mer peptide disrupts the interaction between DOT1L and MLL-AF9 in cells. Flag-DOT1L and Myc-CxxC-AF9 were co-transfected in HEK 293 cells and co-IP was performed. B. Pull down assay using biotin-labeled DOT1L 10-mer peptide.
Figure 11:
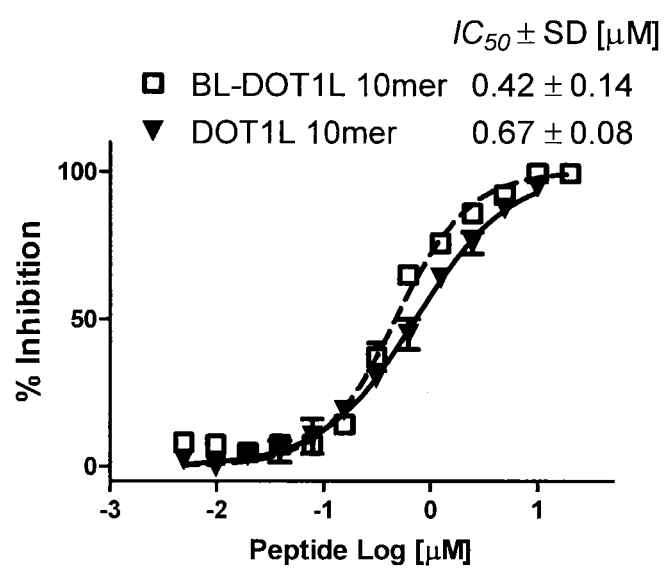
FIG. 11 shows competitive binding curves of biotin-labeled DOT1L 10 mer peptide and corresponding unlabeled 10 mer peptide obtained by fluorescence polarization based assay.

This example shows that DOT1L 10 mer peptide binds cellular MLL-AF9 fusion protein and disrupts the interaction between full length DOT1L and MLL-AF9 fusion protein. To assess whether DOT1L 10-mer peptide can bind and block the interaction between full length DOT1L and MLL-fusion proteins HEK 293 cells were transiently co-transfected ith Flag-tagged human DOT1L protein and Myc-tagged CxxC-AF9 protein. The whole cell lysate was pre-incubated with different concentrations of DOT1L 10-mer peptide and co-immunoprecipitation (co-IP) experiments were performed. The obtained results demonstrate that the DOT1L 10-mer peptide blocks the interaction of cellular DOT1L with CxxC-AF9 in a dose dependent manner (FIG. 10A). To further probe and confirm the cellular target for DOT1L 10-mer peptide, a biotinylated DOT1L 10-mer peptide was synthesized. To determine the binding affinity of this labeled peptide FP competitive based assay was used and tested together with corresponding unlabeled DOT1L 10 mer peptide. The obtained similar $IC_{50}$ values confirmed that biotin labeling did not affect its binding to AF9 protein (FIG. 11). Using this peptide as a tool, streptavidin-biotin pull-down experiments were performed in the HEK 293 cell lysates that showed that the biotinylated DOT1L 10-mer peptide recognizes and binds to the cellular CxxC-AF9 protein in a dose dependent manner (FIG. 10B). Together these experiments demonstrate that DOT1L 10-mer peptide binds to the cellular AF9 protein and blocks its interaction with DOT1L, consistent with the in vitro binding data using recombinant MLL-fusion proteins.

Example 7

Figure 12:
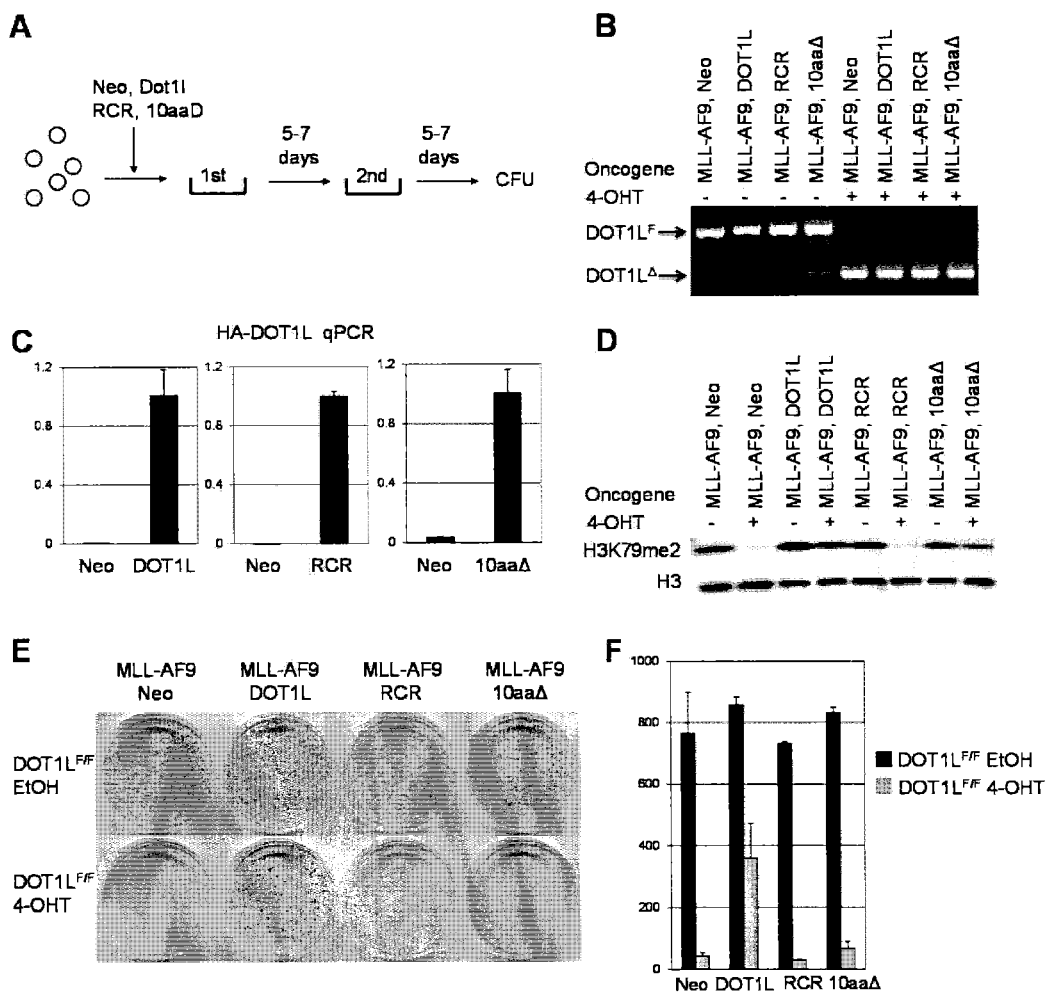
FIG. 12 shows that the AF9 binding site in DOT1L is essential for MLL-AF9 leukemic transformation. A. Schematic presentation of the colony formation unit (CFU) assay. B. Genotyping of transduced bone marrow cells. PCR reaction showed high excision efficiency of endogenous DOT1L with 4-OHT treatment of all cells. C. Quantitative PCR of exogenous DOT1L expression. All constructs showed expression compared with Neo vector alone. D. Western blot of H3K79me2 global level. Histone 3 blot was used as loading control. E. and F. Colony formation on methocult plates. Pictures of iodonitrotetrazolium chloride staining (E) and bar graph of colony counts (F) after second round.

This example describes that the identified 10 residues are essential for DOT1L recruitment and MLL-AF9 leukemic transformation. To assess further the functional importance of the recruitment of DOT1L by MLL-fusion proteins and determine whether identified 10 residues segment of DOT1L is required for MLL-AF9 transformation, colony forming unit (CFU) assays were performed. In these experiments MSCV-based vectors were used to transduce mouse bone marrow cells with leukemogenic MLL-AF9 fusion protein from floxed Dot1l mice generated as described previously (see, e.g., Jo S Y, et al., (2011) Blood 117: 4759-4768). HA-tagged wild-type mouse DOT1L, methytransferase inactive full-length mDOT1L (RCR) with GSG to RCR mutation in the S-adenosylmethionine binding domain and lack enzymatic activity (see, e.g., Min J, et al., (2003) Cell 112: 711-723; Okada Y, et al., (2005) Cell 121: 167-178), full-length mDOT1L 10aaΔ lacking ten amino acid AF9 interacting residues (863 to 872 which are conserved and correspond to the human DOT1L 865 to 874, FIG. 3B), or neomycin vector control were introduced into endogenous DOT1L lacking MLL-AF9 transformed cells (FIG. 12A). Endogenous Dot1l excision was confirmed by PCR and expression of exogenous DOT1L was confirmed by quantitative PCR of HA tag sequences (FIGS. 12B and 12C). As was expected, wild-type DOT1L and mDOT1L 10aaΔ with histone methyltransferase domain intact were able to restore H3K79 methylation while mDOT1L (RCR) failed to restore H3K79 methylation (FIG. 12D). Consistent with the reported findings, the colony forming potential of MLL-AF9-immortalized cells was completely abolished by introducing mDOT1L (RCR) construct after Dot1l deletion, while introduction of exogenous wild-type DOT1L was able to rescue the transformation capability and restore CFU formation (FIGS. 12E and 12F). Importantly, mDOT1L 10aaΔ construct, despite being able to restore H3K79 methylation level in a similar way as the wild-type DOT1L construct, failed to restore CFU formation (FIGS. 12E and 12F). These results strongly suggest that DOT1L interaction with MLL-AF9 and its recruitment are required for transformation by MLL-AF9, and full-length DOT1L lacking the AF9 interacting residues could not rescue CFU formation.

Figure 13:
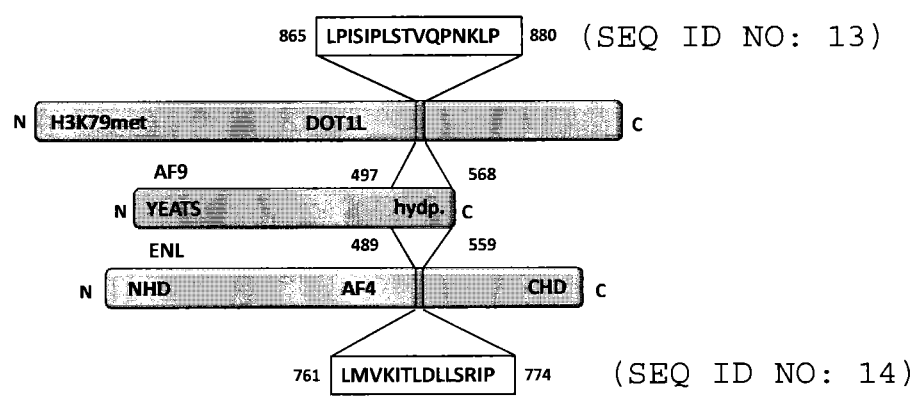
FIG. 13 shows a schematic of proposed model for targeting DOT1L and MLL-fusion protein-protein interactions. A. AF9 binding sites mapped in DOT1L and AF4 proteins (see, e.g., Srinivasan, R. S., et al., (2004) Leukemia 18, 1364-1372). B. Small-molecule inhibitor (SMI) that binds to C-terminal domain of AF9/ENL will disrupt the MLL-fusion protein complexes involved in mixed lineage leukemia, the DOT1L and AEP complex.
Figure 13:
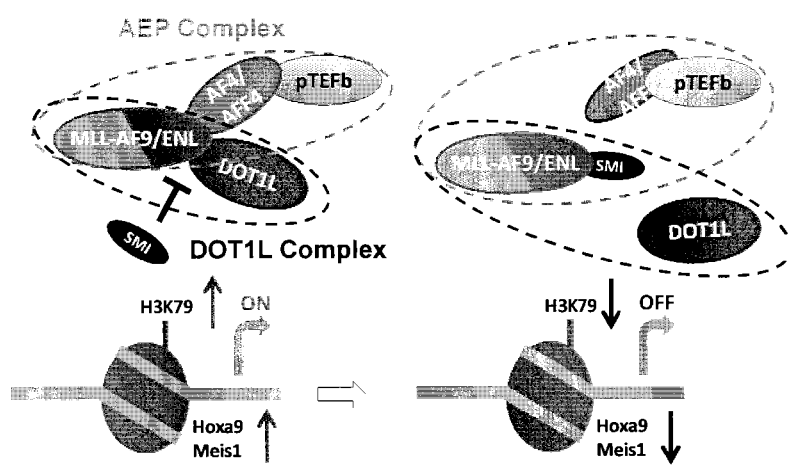

Furthermore, the binding studies clearly demonstrate that DOT1L and AF4 proteins, as well as the DOT1L 10-mer and AF4 14-mer peptide bind to the same C-terminal hydrophobic domain of AF9 and ENL (FIG. 13A), consistent with biochemical and functional analyses of protein complexes associated with MLL-fusion proteins, which showed that AF9 and ENL exist in two mutually exclusive complexes, AF9/ENL-DOT1L and AF9/ENL-AF4-pTEFb (see, e.g., Yokoyama, A., et al., (2010) Cancer cell 17, 198-212; Biswas, D., et al., (2011) PNAS 108, 15751-15756). The results indicate that small molecules that bind the conserved hydrophobic domain of AF9 and ENL will abolish the AF9 interactions with both AF4 and DOT1L, disrupting the higher order complex AEP and the complex with DOT1L, and thereby blocking the MLL fusion-mediated leukemogenesis (FIG. 13B).

Example 8

This example describes the materials and methods for Examples 1-7.

Plasmids and Cloning—All different DOT1L plasmids, tested in this study (Table 2), were constructed using full length hDOT1L as a template. The plasmids for AF9, ENL and AF4, were made using MLL-AF9, MLL-ENL and MLL-AF4 fusion proteins as templates. All these constructs for protein expression were cloned by ligation independent cloning (LIC) methods as described before (see, e.g. Del-Proposto, J., Majmudar, C. Y., Smith, J. L., and Brown, W. C. (2009) Protein Expr Purif 63, 40-49). Different DOT1L constructs (Table 1) and AF4 proteins (749-775) were cloned into pMocr-LIC vector. ENL (489-559) was cloned into pMSCG9-LIC vector and AF9 (497-568) was cloned into pGB 1-LIC vector. MSCV based HA tagged wild type mouse DOT1L, methyltransferase mutant DOT1L (RCR), and neomycin vector constructs are reported before (see, e.g., Jo, S. Y., et al., (2011) Blood 117, 4759-4768). MSCV-HA-mDOT1L 10aaΔ construct where 10 residues identified as AF9/ENL interaction site (863-872 aa) were deleted by using the QuickChange site-directed mutagenesis kit (Agilent Technologies). These residues in mouse are conserved and correspond to the identified human DOT1L interaction site, 865-874 aa (FIG. 3B). ENL L550E mutant was also created by site-directed mutagenesis (Quick-Change, Agilent Technologies). To construct the pCMV-Myc CxxC-AF9 μlasmid, a fragment of an MLL-AF9 fusion protein was cut from an MLL-AF9 fusion protein expression vector using MfeI and XhoI and inserted into the pCMV-Myc vector (Clontech) following digestion with EcoR1 and XhoI. A dual nuclear localization signal was inserted into the SfiI site downstream of the Myc tag. The sequence of MLL includes amino acids 1116 through 1422 and is followed by AF9 sequence including amino acids 479 through 568. The positive clones for all desired constructs were confirmed by DNA sequencing (University of Michigan DNA sequencing core).

Protein expression and purification—All recombinant proteins were expressed in *Escherichia coli* strain BL21 (DE3) (Invitrogen). The medium for bacterial growth was Luria Broth (for all binding studies) and M9 minimal medium supplemented with $^{15}NH_4Cl$ (Cambridge Isotope Laboratories) (for HSQC NMR studies). All the proteins were induced with 200 μM IPTG at 20° C. except GB1-AF9 (489-497) was induced at 16° C. The cells were harvested after 20 h and resuspended in cold lysis buffer (50 mM Tris HCl, pH 7.5, 150 mM NaCl, 0.01% β-mercatoethanol) and purified by affinity chromatography employing Ni-agarose (Qiagen). Mocr-DOT1L and -AF4 proteins were further purified by ion exchange chromatography in 25 mM Tris HCl pH 7.5, with NaCl gradient ranging from 25 mM to 1 M, and 3 mM DTT, while MBP-ENL (489-559), MBP-ENL (489-559) L550E, and GB1-AF9 (497-568) proteins were further purified with size exclusion chromatography in 50 mM Tris HCl, pH 7.5, 150 mM NaCl, 3 mM DTT. The MBP and Mocr-tags from ENL (489-559) and AF9 (497-568), respectively, were removed by proteolysis using tobacco etch virus (TEV) protease, followed by nickel-column and size exclusion chromatography using the same buffer as above to obtain purified cleaved proteins. All purified recombinant proteins were stored at −80° C. for further experiments.

Peptide synthesis—Peptides were synthesized using standard F-moc solid phase peptide synthesis techniques on an ABI 433A automated peptide synthesizer. NovaPEG Rink amide resin (EMD) was used to prepare all C-terminal amide-capped peptides. Standard side chain protecting groups were used for all amino acids. All the peptides were acetylated on the N-terminal. Peptides containing an N-terminal biotin group or fluorescein are coupled to lysine and two β-alanine residues as a spacer. All crude peptides were purified by semi-preparative reverse-phase high-performance liquid chromatography (RP-HPLC) and their sequence and purity were verified by electrospray ionization mass spectrometry (ESI-MS) and analytical RP-HPLC.

Surface Plasmon Resonance (SPR) binding studies—All SPR based experiments were performed on a BIAcore 2000 (BIAcore, GE Healthcare) instrument. Different tested DOT1L recombinant proteins were immobilized on a CM5 sensor chip by standard EDC/NHS coupling chemistry followed by ethanolamine deactivation of the surfaces. For immobilization of full length Flag-DOT1L protein, anti-Flag antibody (Sigma, Anti-FLAG M2) was immobilized on CM5 chip by the same amine coupling chemistry. HEK293 whole cells lysate with overexpressed Flag-DOT1L at 2.4 μg/l total protein concentration was injected over the Flag antibody surface, followed by injecting of AF9 and ENL in different concentrations. For determination of their binding affinity AF9 and ENL were tested in concentration from 0.01 to 3 μM in HBS-P buffer (10 mM HEPES pH 7.4, 150 mM NaCl, 0.005% v/v P20, GE Healthcare). The Fc1 surface was used as a control surface and was treated in the same manner as the active surfaces but in the absence of immobilized protein. Binding parameters, $k_{on}$, $k_{off}$ and $K_d$ were calculated by simultaneous non-linear regression using BIAEvaluation software.

Solution competitive SPR based assay was performed to determine the $IC_{50}$ values of DOT1L peptides. The tested DOT1L wild type and alanine mutated peptides were pre-incubated with AF9 or ENL proteins (500 nM) for at least 30 minutes and then the reaction mixture was injected over the surface of Mocr-DOT1L (826-1095) immobilized CM5 chip. Response units (RU) were measured at 15 seconds in the dissociation phase and the specific binding was calculated by subtracting the control surface (Fc1) signal from the surfaces with immobilized Mocr-DOT1L. $IC_{50}$ values were determined by non-linear least squares analysis using Graph Pad Prism 5.0 software.

Fluorescence polarization (FP) assay—FP experiments were performed in 96-well, black, round-bottom plates (Corning) using the plate reader (Biotek H1 hybrid). Fluorescein tagged DOT1L 10 mer peptide (Flu-DOT1L) was used as a fluorescent probe in the FP based binding assays. The $K_d$ values of GB1-AF9, MBP-ENL wild type and L550E mutated proteins, were determined using a fixed concentration of the tracer (10 nM Flu-DOT1L) and different concentrations of the tested proteins, in a final volume of 125 μl and assay buffer (100 mM $Na_2HPO_4$, pH 7.4, 150 mM NaCl, 0.01% Triton X-100 and 4% DMSO). The plate was mixed on a shaker and incubated at room temperature to reach equilibrium. The polarization values in milli-polarization units (mP) were measured at an excitation wavelength at 485 nm and an emission wavelength at 530 nm. Polarization data were analyzed using GraphPad Prism 5.0 by non-linear fitting with a one-site binding model.

AF4 (749-775) protein and several peptides (AF4 14 mer, un-labeled and biotin-labeled DOT1L 10 mer peptide) were tested for their ability to displace the Flu-DOT1L from GB1-AF9 protein. The dose-dependent binding experiments were carried out in 96-well plates with serial dilutions of tested protein or peptides, GB1-AF9 protein (500 nM) and Flu-DOT1L (10 nM) in the same assay buffer and final volume of 125 µL. The polarization values were measured after 3 h incubation. Negative controls containing GB1-AF9 protein and probe (equivalent to 0% inhibition), and positive controls containing only free Flu-DOT1L probe (equivalent to 100% inhibition), were included on each assay plate. $IC_{50}$ values were determined by nonlinear regression fitting of the competition curves (GraphPad Prism 5.0).

Isothermal titration calorimetry—ITC was carried out using a Nano-ITC Micro Calorimeter (TA Instruments) at 20° C. MBP-ENL (489-559) was dialysed extensively against 50 mM $Na_2HPO_4$, (pH 7.5) and 100 mM NaCl, and 80 µM was used for titration studies of DOT1L 16-mer and 10-mer peptides, and 110 µM for DOT1L 7-mer titration. Tested peptides dissolved in the same buffer at 400 µM (DOT1L 16-mer and 10-mer) or 500 µM (DOT1L 7-mer) were tested by injecting 2 µl aliquots into the protein sample, at time intervals of 30 seconds, to ensure that the titration peak returned to the baseline. The ITC data were analyzed by NanoAnalyze software package using a one site-binding model.

NMR spectroscopy—$^{15}$N-labeled ENL protein sample was prepared in a 50 mM $Na_2HPO_4$, pH 7.5, 50 mM NaCl in 7% $D_2O$. The binding of DOT1L protein and peptides has been characterized by recording $^1H,^{15}N$-HSQC spectra of uniformly $^{15}$N-labeled ENL in the absence and presence of tested protein and peptides in 1:1 molar ratio. The presence of tested peptides in solution was confirmed by $^1H$-1D NMR. All spectra were acquired at 30° C. on a Bruker 600 MHz NMR spectrometer equipped with a cryogenic probe, processed using Bruker TopSpin and rNMR (see, e.g., Lewis, I. A., Schommer, S. C., and Markley, J. L. (2009) Magn Reson Chem 47 Suppl 1, S123-126), and were analyzed with Sparky (see, e.g., Goddard, T. D., and Kneller, D. G. SPARKY 3. in University of California, San Francisco).

Circular dichroism—DOT1L peptides were dissolved in phosphate buffer (50 mM $Na_2HPO_4$, pH 7.4, 100 mM NaCl). ENL and AF9 protein were dialyzed against the above phosphate buffer overnight. CD measurements were performed at room temperature using a Jasco J-715 and a quartz flow cell with a 1 mm path length. The spectra were averaged over 10 scans and the baseline (buffer scan) was subtracted from each spectrum. The percentage of a helicity was calculated by K2D2 online tool.

Cell Culture, Transfections, and Immunoprecipitation—HEK293 cells were plated in 100 mm culture dishes and cultured in Dulbecco's modified Eagle's medium (DMEM) supplemented with 10% FBS and antibiotics. Co-transfection with FLAG-DOTL and Myc-CxxC-AF9 was performed using Lipofectamine 2000 (Invitrogen). Forty eight hours post-transfection, cells were collected and lysed using BC-300 lysis buffer: 20 mM Tris-HCl pH 8.0, 300 mM KCl, 1 mM EDTA, 10% glycerol, 0.1% NP-40 and protease inhibitor cocktail (Roche). The lysates was pre-cleared for 2 h in Mouse IgG Agarose (Sigma-Aldrich). The pre-cleared lysates were incubated with different concentrations of DOT1L 10 mer peptide at 4° C. overnight. The next day, the cell lysates were immunoprecipitated with Anti-FLAG M2 magnetic beads (Sigma-Aldrich) at 4° C. for 2 h. After incubation, the beads were washed extensively, boiled in SDS loading buffer and analyzed by western blotting using mouse monoclonal anti-FLAG M2 (Sigma-Aldrich) and goat monoclonal anti-Myc tag (Abcam) antibody.

Pull-down assay—HEK293 cells transfected with Myc-CxxC-AF9 were lysed in BC-300 lysis buffer in a same way as the immunoprecipitation experiment. The supernatant was pre-cleared for 2 h in streptavidin agarose beads (Thermal Scientific). The pre-cleared lysates were incubated with different concentrations of biotin-labeled DOT1L 10 mer peptide at 4° C. overnight. The next day, the cell lysate were incubated with streptavidin agarose at 4° C. for 2 h. After extensive washing the beads with the BC-300 lysis buffer without NP-40, the pull down samples were applied to SDS-PAGE electrophoresis and pull-down Myc-CxxC-AF9 protein was probed with goat monoclonal anti-Myc tag antibody (Abcam).

Retroviral Transductions and CFUAssay—Retroviral production and transduction of bone marrow progenitor cells were carried out as described (see, e.g., Jo, S. Y., et al., (2011) Blood 117, 4759-4768). Briefly, retroviruses were generated by transfecting MSCV-HA wild type mouse DOT1L, methyltransferase mutant mDOT1L (RCR), mDOT1L deletion (10aaΔ; deletion of the residues 863-872 aa) constructs, and neomycin vector control into Plat-E cell line with Fugene 6 (Roche). Fresh viral supernatants were used for transducing MLL-AF9 transformed cells described (see, e.g., Jo, S. Y., et al., (2011) Blood 117, 4759-4768). 150,000 cells were used for transduction per viral supernatant from 10 cm dish. Cells were then plated on Methocult media (Stem Cell Technologies, M3234) with 1% penicillin/streptomycin (Invitrogen), 10 ng/ml IL3 (R & D Systems), 5 nM 4-OHT (Sigma) or 100% ethanol, and 1 mg/ml G418 (Invitrogen). Colonies were scored 5-7 days after plating for two rounds. In the final round, colonies were stained with 0.1% p-iodonitrotetrazolium violet (Sigma) for visualization.

RNA extraction, cDNA generation, and Protein extraction—RNA was extracted from cells using TRIzol Reagent (Invitrogen) and converted to cDNA using SuperScript II (Invitrogen) according to manufacturer's instructions. Whole cell lysate samples were prepared by directly resus-pending cells in Tris-Glycine SDS sample buffer (Novex) and sonicating for 15 minutes (Bioruptor, Diagenode). Primers for quantitative PCR (qPCR) are provided:

```
Primers for and Quantitative PCR (qPCR):
5S rRNA:
                                      (SEQ ID NO: 23)
TCTACGGCCATACCACCCTGA
and (SEQ ID NO: 24)
GCCTACAGCACCCGGTATTCC;

HA-Dot1l:
                                      (SEQ ID NO: 25)
GCCACCATGTACCCCTACGACGTG
and (SEQ ID NO: 26)
GATTTCCTCGCAGACCCACCGGAT
```

Example 9

This example describes the development and optimization of a quantitative fluorescence polarization (FP)-based binding assay for screening compounds targeting the PPI between DOT1L and AF9 fusion protein. Based on the detailed biochemical characterization of the DOT1L/AF9 interactions (see, e.g., Shen C, Jo S Y, Liao C, Hess J L, Nikolovska-Coleska Z. (2013) J Biol Chem. 288 (42): 30585-96), an FP-based binding assay was established and optimized. For the development of this assay, the recombinant GB1-AF9 protein (residues 497-568), a minimal AF9 fragment necessary for the transformation ability of MLL-fusion protein, was expressed and purified.

Figure 15:
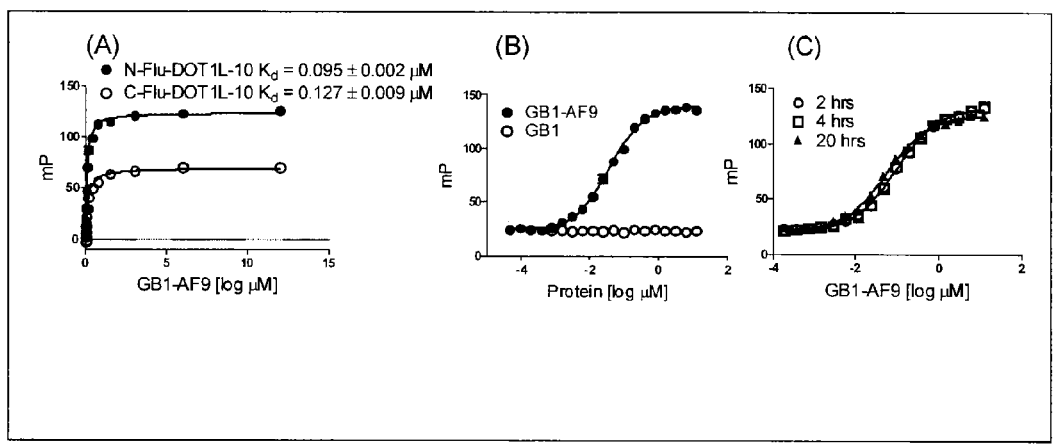
FIG. 15 shows flu labeled DOT1L-10 mer peptide binds to AF9. (A) Saturation experiment to determine the $K_d$ values of AF9 binding to N-terminal (N-Flu-DOT1L) and C-terminal (C-Flu-DOT1L) DOT1L. A fixed concentration of 5 nM was used for labeled DOT1L peptides, which was titrated by GB1-AF9 with concentrations between 1 nM and 12,000 nM. (B) FP assay was conducted as above using N-Flu-DOT1L-10 where in addition to GB1-AF9, GB1 was included as a control. (C) Time course measurements of the GB1-AF9 binding to the N-Flu-DOT1L.
Figure 16:
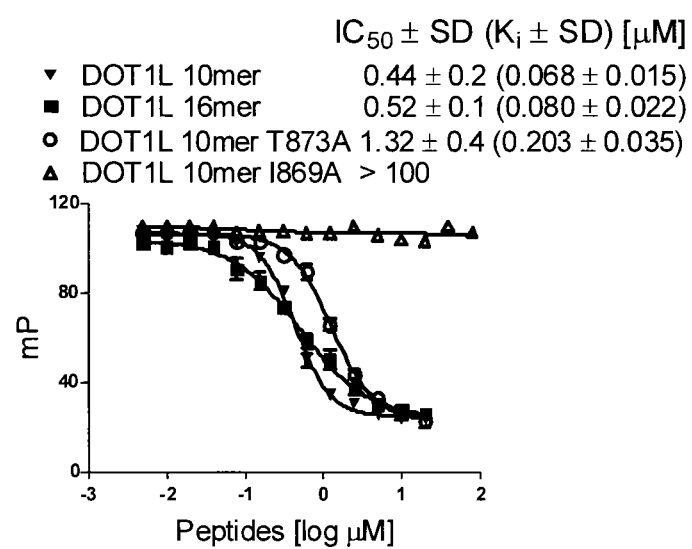
FIG. 16 shows a competitive FP binding experiment. Peptides were tested for their ability to displace the fluorescently labeled N-Flu-DOT1L from AF9 protein.

The binding studies with synthetic DOT1L peptides demonstrate that the DOT1L-10 mer peptide is sufficient to disrupt the PPI between DOT1L and AF9. Design and synthesis of two fluorescently labeled DOT1L-10 mer peptides, labeled either on the N-terminal (N-Flu-DOT 1L) or C-terminal (C-Flu-DOT1L) enabled selection of the tracer that will give us the best dynamic range and signal-to-noise ratio in the assay. Using the FP based method, the dissociation constant ($K_d$) of recombinant GB1-AF9 protein and the fluorescently-labeled DOT1L peptides was determined. Saturation experiments showed that N-Flu-DOT1L and C-Flu-DOT1L bind to AF9 with similar $K_d$ values, 0.095±0.002 µM and 0.127±0.009 µM, respectively (FIG. 15). These results are consistent and in good agreement with the previous results obtained from the SPR assay. However the dynamic range in the assays was significantly different: N-Flu-DOT1L gives much better dynamic range with ΔmP of 125, while C-Flu-DOT1L gives 50% lower dynamic range, ΔmP of 70 (FIG. 15A). Therefore, by using N-terminal labeled DOT1L-10 mer peptide a 50% increase in the assay window (signal-to-noise ratio) was achieved, providing sufficient signal for the development of a competitive FP based assay. The GB1 protein was also titrated against N-Flu-DOT1L peptide and at concentrations up to 12 µM, failed to show any binding to the tracer, demonstrating that the binding characteristics of the GB1 fusion AF9 protein are not affected by the GB1 tag (FIG. 15B). Furthermore to this end, various buffers, salt concentrations, and detergent conditions were explored. Using a buffer 100 mM $NaH_2PO_4$, pH 7.5, 150 mM NaCl, and 0.01% Triton X-100 as a detergent, we achieved the best dynamic range, signal stability up to 20 hours (FIG. 15C) and found that the assay can tolerate up to 4% DMSO. In the optimized competitive FP based assay, based upon the $K_d$ value, the concentration of AF9 is 500 nM and of N-Flu-DOT1L, 5 nM. To validate the assay, the binding affinity of the corresponding unlabeled DOT1L-10 mer peptide, DOT1L-16 mer and two mutated peptides with different binding affinities to AF9 were evaluated (FIG. 16). The competitive experiment showed that unlabeled DOT1L-10 mer peptide can displace the fluorescently labeled N-Flu-DOT1L from AF9 in a dose-dependent manner with a $K_i$ value of 0.068±0.015 µM, consistent with the $K_d$ value of N-Flu-DOT1L with AF9, determined in the saturation experiment. Consistent with the competitive SPR based assay, the DOT1L-16 mer and DOT1L-10 mer with alanine mutation, T873A, have very similar binding affinities to the DOT1L-10 mer, $K_i$ values of 80 nM and 203 nM, respectively. As was expected, the peptide in which one of the conserved residues is mutated to alanine, 1869A, showed no binding at concentrations up to 100 µM (FIG. 16). These validation experiments provide evidence that the FP competitive binding assay can quantitatively and accurately determine the binding affinities of small-molecule inhibitors with a wide range of binding affinities to the AF9 protein.

Example 10

Figure 17:
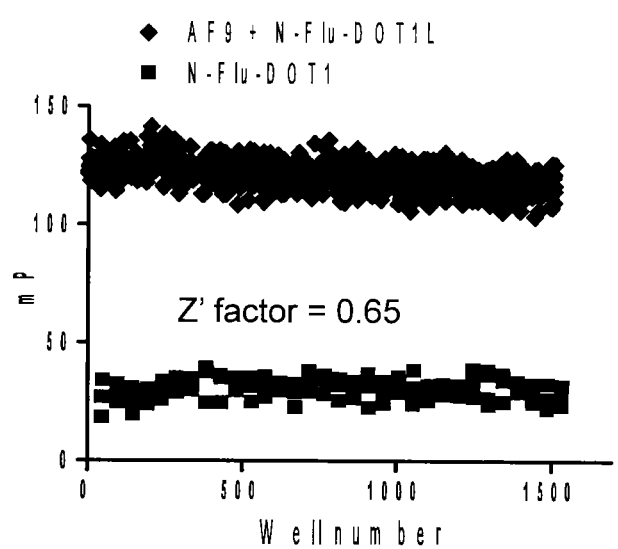
FIG. 17 shows a graph calculating the Z' factor of 1536-well format.

This example shows miniaturization of FP based assays to 1536-well format for HTS. The FP based assay was optimized in 384-well format, which has a Z' factor of 0.77 and remained >0.7 after overnight incubation. In order for the screen to be more cost effective, the FP assay was successfully miniaturized to 1536-well format using 4 µl total volume, significantly reducing reagent consumption, without compromising assay reliability. Z' factor value determined for the FP assay in 1536-well format was found to be 0.65 (FIG. 17), confirming the assay to be robust, reliable, and suitable for HTS purposes.

Example 11

Figure 18:
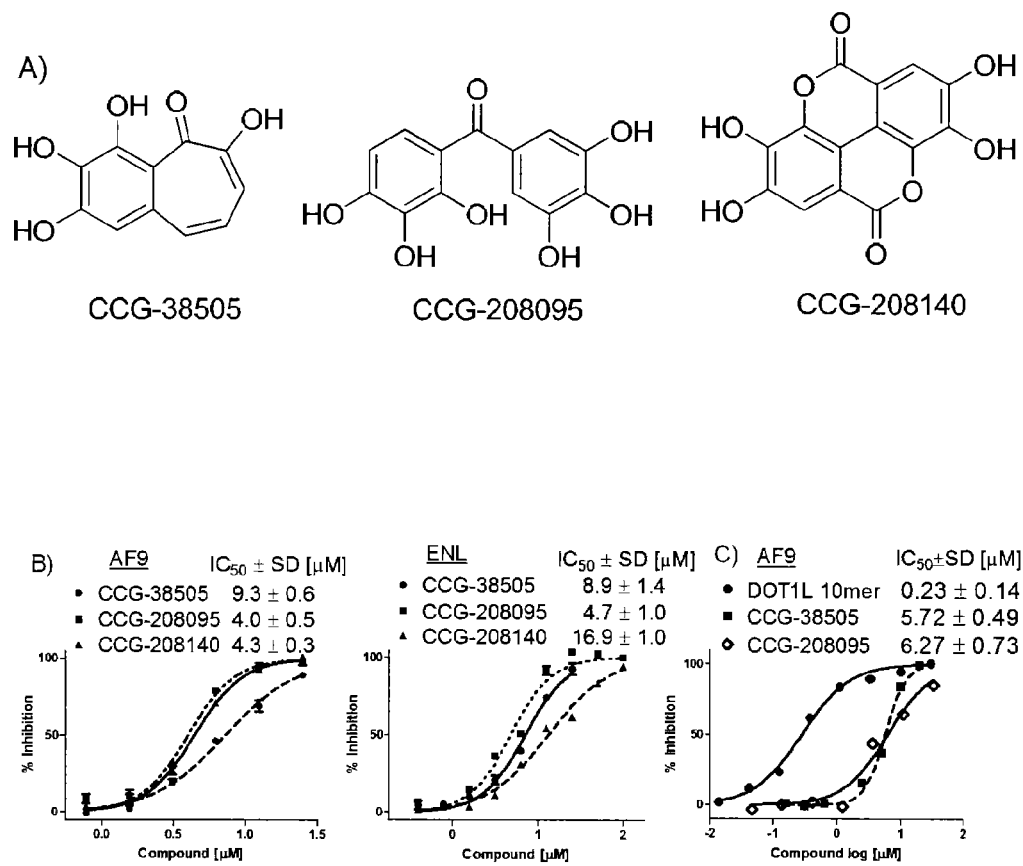
FIG. 18 shows A) Chemical structures of identified natural polyphenolic inhibitors of DOT1L/AF9 PPI. B) Competitive FP binding curves to AF9 and ENL.C) SPR competitive binding curves to AF9 (see Example 11).

The example describes the screening library of compounds. Screening efforts were continued in order to identify and validate good lead compounds targeting PPI between DOT1L and MLL-AF9 by employing the optimized FP-based assay. This screen was performed at the Center for Chemical Genomics at the University of Michigan using following libraries: BioFocus NCC (NIH clinical collection), focused collection (Autophagy, Wnt Pathway, Epigenetics, Protein Kinase, Protease, REDOX, Cannabinoid, Natural Products) and MS Spectrum 2000 (MicroSource bioactive compounds), in total 3,500 structurally diverse, small molecules. Initial screening of these compounds at a single concentration of 20 µM identified 24 of them as achieving 50% or greater inhibition of the binding of the N-Flu-DOT1L to AF9. The secondary, dose-response experiments confirmed 13 compounds. Based on their chemical structures and commercial availability 6 compounds were ordered and confirmed 3 compounds using new fresh stock solutions (FIG. 18A). All three identified compounds are polyphenolic natural products. Preliminary data demonstrated that the full length and different protein constructs of DOT1L protein, as well as peptides derived from DOT1L, show a similar binding pattern to C-terminal highly conserved domain in both proteins, AF9 and ENL. Therefore, it was expected that the identified compounds will also bind to ENL protein, thus disrupting the interaction between DOT1L and ENL. Indeed, as expected, the identified compounds were able to bind ENL protein with similar $IC_{50}$ values (FIG. 18B).

Several secondary assays have already been developed to support hit confirmation and the hit-to-probe optimization process. The established and optimized SPR-based competitive assay utilizing DOT1L protein (826-1095) immobilized on the CM5 sensor chip was used as a secondary counter screen assay to validate binding of compounds to AF9. CCG-38505 and CCG-208095 bind to AF9 and inhibit the AF9-DOT1L interaction with $IC_{50}$ values of 5.72 µM and 6.27 µM, respectively (FIG. 18C). Both assays gave similar $IC_{50}$ values. These data demonstrate the feasibility of development of small molecules targeting C-terminal hydrophobic domain in AF9, indicating it is a "druggable" target.

Example 12

The example describes the screening library of compounds.

Using the optimized competitive FP binding assay, a library of 101,000 structurally diverse small molecules was screened at the Center for Chemical Genomics, University of Michigan. Primary screening of these compounds at a single concentration of 20 µM identified 1,191 potential active compounds (1.2% hit rate) defined by >30% displacement of Flu-DOT1L/AF9 interaction (>3 standard deviations). The compounds identified in this way were advanced to increasingly stringent confirmatory in vitro binding assays, including: 1) repeat single-dose testing of 1,191 compounds in triplicates; 2) identify and filter compounds with auto fluorescence, quenchers and compounds with reactive functional groups; and then 3) dose-response competitive binding of the 164 confirmed compounds. 39 compounds competed with Flu-DOT1L 10 mer peptide for AF9 binding and demonstrated dose-dependent inhibition, giving a 0.04% overall hit rate. The analysis of their chemical structures using Tripos BenchWare DataMiner, showed that the majority of hits fell into the following five structural classes:

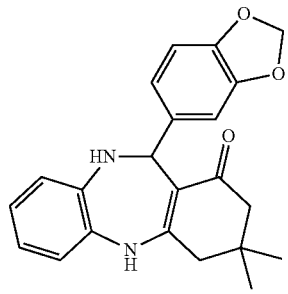

CCG-17597
Class I

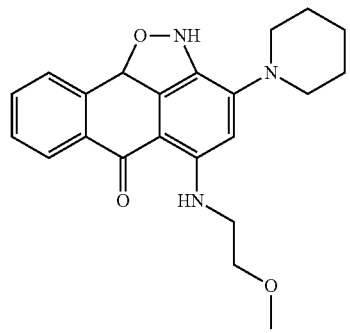

CCG-133982
Class II

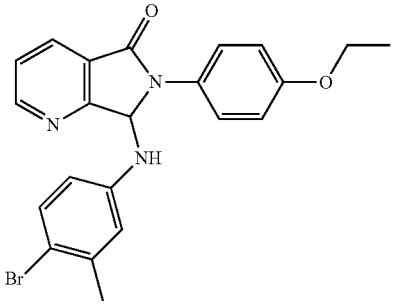

CCG-133361
Class III

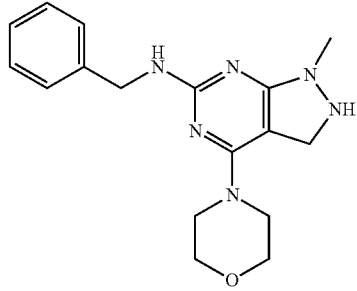

CCG-186912
Class IV

-continued

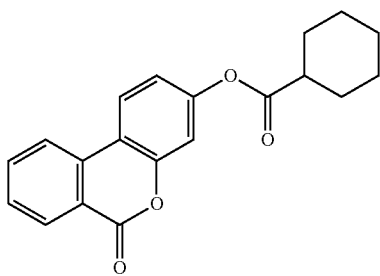

CCG-110788
Class V

An important step after performing HTS to identify small-molecule modulator of protein function is the follow-up of the hits and their characterization and validation into high-content lead series. Based on the potency, chemical structure and availability of these 39 compounds, the following 8 compounds were purchased and new stock solutions were prepared:

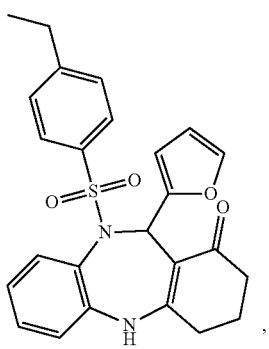

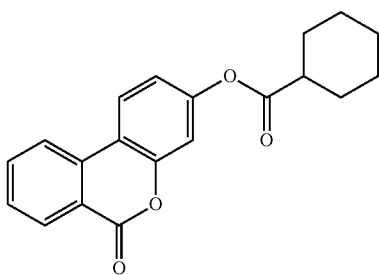

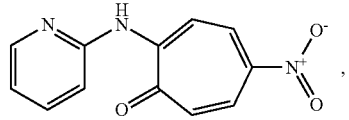

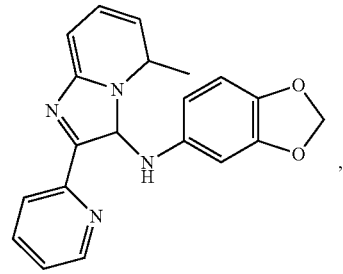

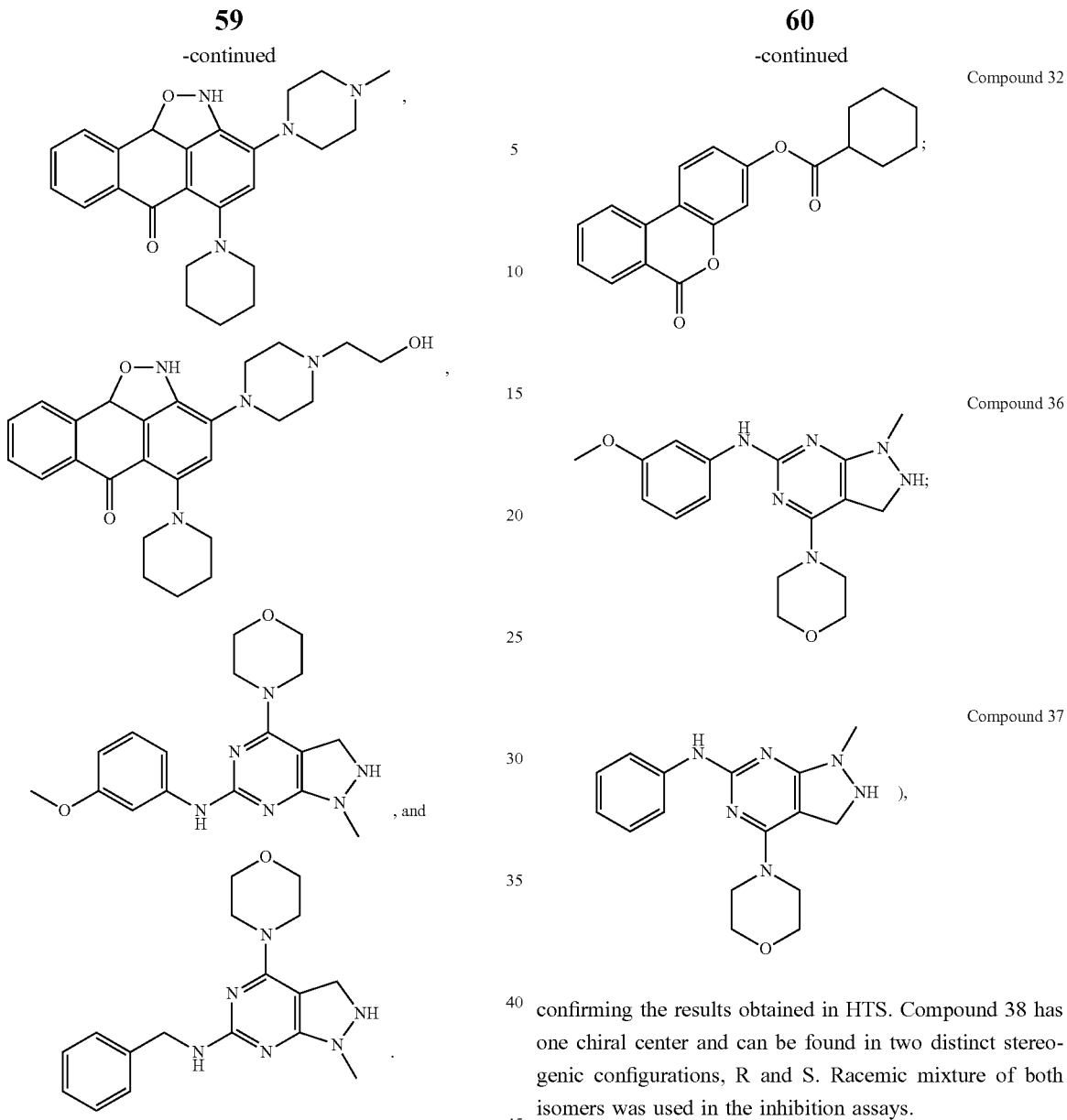

Their chemical structures were confirmed by NMR or LC-MS and re-tested using the FP-based binding assay. Three of these compounds, belonging to the chemical clusters I, IV and V, demonstrated reproducible dose-dependent inhibition of the AF9-DOT1L interaction with $IC_{50}$ in the 30-50 µM range (FIG. 19A;

Compound 38

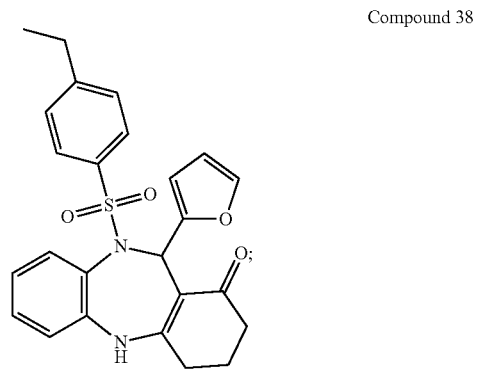

confirming the results obtained in HTS. Compound 38 has one chiral center and can be found in two distinct stereogenic configurations, R and S. Racemic mixture of both isomers was used in the inhibition assays.

Figure 19:
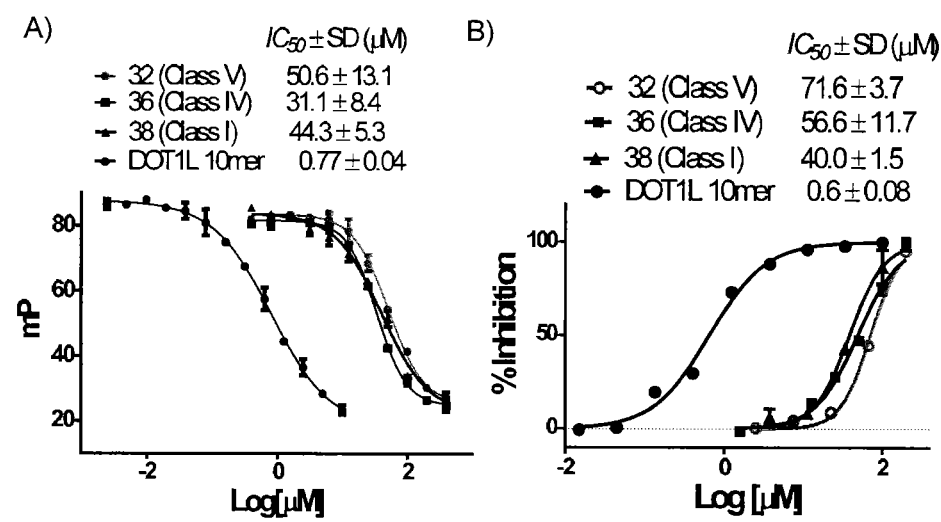
FIG. 19 presents a dose-response competitive binding curves of active compounds obtained with A) FP and B) SPR binding assay (see Example 12).

To further validate the binding of the confirmed compounds and identify potential promiscuous inhibitors, several secondary assays have been developed to support hit confirmation and the hit-to-probe optimization process. In order to determine that the compounds bind effectively to the target and disrupt protein-protein interaction, a SPR competitive binding assay was used. This assay uses a platform that differs from the FP-based assay where DOT1L recombinant protein (residues 865-1085) is immobilized on a CM5 chip, allowing for testing of the inhibitors for their ability to disrupt AF9-DOT1L protein-protein interactions. Compounds confirmed in FP showed similar potency in disrupting the PPI with $IC_{50}$ from 40 to 72 µM (FIG. 19B).

Figure 20:
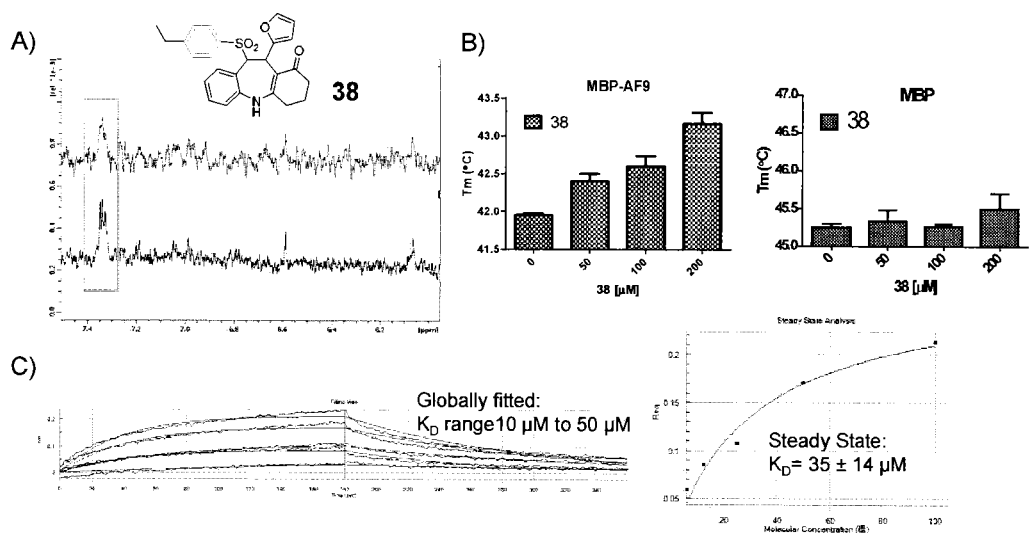
FIG. 20 demonstrates that A) 1D NMR (bottom spectrum) and 1D STD spectrum (top spectrum) of 38 (400 µM) with AF9 (5 µM); B) Thermofluor studies for testing direct binding to MBP-AF9 and MBP tag. C) Globally fitted concentration series of 38 (100, 50, 25, 12.5 and 6.25 µM) binding to immobilized AF9 using OctetRed System (see Example 12).

To provide further validation of the hit selection in addition to the biochemical assays Saturation Transfer Difference (STD), NMR spectroscopy was used. NMR spectroscopy has been successfully utilized to detect and characterize the direct binding of small-molecule compounds to large biomolecules. This technique is also allowing characterization of the binding interactions and maps the ligand-protein contacts in the bound state, delineating which chemical moieties of the ligand molecule are key for molecular recognition by the protein (group epitope mapping, FIG. 20A). A strong STD effects were observed for two compounds, 36 and 38, indicative of their direct binding to AF9. Peak assignment in the proton NMR spectrum of compound 38 (FIG. 20A) revealed that the signals in the STD NMR spectrum correspond to the aromatic protons from the phenyl ring demonstrating that the phenyl ring attached to the benzodiazepinone core structure in 38 is involved in the interaction with AF9 protein. The direct binding of 38 was also confirmed with ThermoFluor biophysical binding assay. ThermoFluor exploits a well-known biophysical phenomenon where small changes in the intrinsic melting temperature of proteins in the presence of ligands are related to the equilibrium-binding constant. Compounds that interact with the native form of the protein will shift the equilibrium to the left, increasing the $T_m$, the temperature at which half the protein is unfolded. In the presence of compound 38, the $T_m$ of MBP-AF9 protein increases in a dose-dependent manner, giving $\Delta T_m$ of 1.2 degree in 200 RM (FIG. 20B). At the same time, testing against the tag MBP only did not show any changes in thermal stability. These results further confirm that compound 38 binds directly to the AF9 protein.

Finally, an orthogonal measure of the disruption of the DOT1L/AF9 protein interaction was obtained using Octet-Red system with Bio-Layer Interferometry (BLI) technology. This technology is allowing label-free, real-time biomolecular analysis and determination of binding kinetics and affinity. Using this technology, the binding affinity ($K_D$) of compound 38 calculated with steady state analysis was determined to be 35 µM (FIG. 20C). Using global fitting of the binding data in several tested concentrations, the kinetic parameters were calculated. The observed $K_D$ values ranged from 10 µM to 50 µM, consistent with the $K_D$ from steady state calculations.

Example 13

This example describes the initial structure activity relationship (SAR) of the benzodiazepinone series of compounds.

Figure 21:
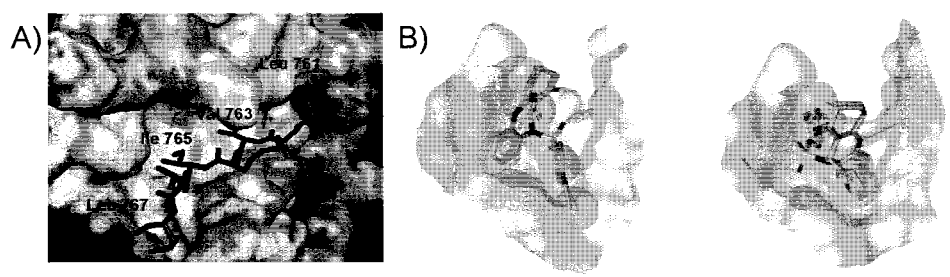
FIG. 21 presents A) NMR structure of AF9-AF4 complex. AF9 presented with molecular surface and AF4 7 mer peptide shown with labeled conserved residues. B) GOLD-determined binding modes of the (S) left and (R) right isomer of the compound 38. AF9 hydrophobic pocket schematically shown by its molecular surface (Whiter surface indicates hydrophobic residues; darker denotes hydrophilic molecular surface).

Recently, the NMR structure of the fusion AF9-AF4 protein was reported (see, e.g., Leach, et al., Structure 21, 176-183 (2013)). Using this structure and applying GOLD molecular docking, the predicted binding model of lead compound 38 was obtained (FIG. 21). The binding site was defined as a 16 Å around the center of the hydrophobic cavity encompassed by residues Leu761, Val763, Ile765 and Leu767 of the AF4 peptide (FIG. 21A). Both stereoisomers of the 38 compound were generated and docked into the AF9 hydrophobic binding site (FIG. 21B). In both predicted binding modes, the benzodiazepinone core of compound 38 was placed perpendicularly into the AF9 hydrophobic binding pocket occupying the same space as AF4 Ile765 amino acid in the experimental NMR structure of AF9-AF4 complex. Such experiments demonstrated that AF4 and DOT1L compete for the same AF9 hydrophobic binding site and the alignment showed that they share the conserved residues (see, e.g., Shen, et al., J Biol Chem. 2013, 288 (42), 30585-96)). Alanine scanning mutagenesis studies demonstrate that the DOT1L Ile869 conserved residue (corresponding to AF4 Ile765) is essential for DOT1L binding to AF9 (see, e.g., Shen, et al., J Biol Chem. 2013, 288 (42), 30585-96)). This position of the benzodiazepinone core is also enabling a favorable placement of the compound's ethylphenyl attached through the sulfonamide linker ($R_1$) and furane ($R_2$) moieties deep inside the hydrophobic pocket of the AF9 protein. Based on the isomer R or S orientation, two different placements of these two moieties were observed (FIG. 21B). Subsequently, LigandScout software (see, e.g., Wolber, G. & Langer, T. (2005) Journal of chemical information and modeling 45, 160-169) was used to derive the structure-based pharmacophore features using GOLD-proposed docked conformations to highlight crucial features potentially responsible for the 38-AF9 molecular recognition and interaction. As seen in FIG. 21, both isomers interact predominantly through hydrophobic interactions with several AF9 amino acids residues including Leu1523, Phe1543, Met1515 and Leu1514. For the R isomer, a hydrogen bond between the substituted nitrogen on the core scaffold and AF9 Phe1543 residue was observed (arrow).

After confirmation of the initial binding results and after obtaining a predicted binding model, the hit-to-probe process was initiated by an analog-by-catalog approach. A limited number of available analogs were identified and purchased to obtain initial SAR around the benzodiazepinone series (Table 4). Replacement of the $R_1$ substituent, ethyl phenyl, with propyl phenyl or methyl phenyl in 42 and 41 respectively, showed that they had a similar favorable interaction with AF9 and did not affect binding. Similar to $R_1$, replacement of the $R_2$ substituent furan group with thiophen was well tolerated and the corresponding compound 48 showed similar $IC_{50}$ value in disrupting DOT1L-AF9 PPI as lead compound 38. However, deletion of the bulky substituted phenyl hydrophobic group in $R_1$ position is detrimental for binding to AF9, thus compound 51 did not show binding up to 200 µM, consistent with the STD NMR results and predicted binding model of 38 in complex with AF9 showing that this substituent is involved in hydrophobic interactions. Docking studies of these analogs showed that the same structural characteristics of molecular recognition were observed throughout the compound class.

TABLE 4

IC$_{50}$ values of several commercially available analogs obtained in SPR competitive based assay.

[Core structure: dibenzodiazepinone scaffold with R$_1$SO$_2$- on N, R$_2$ substituent, and R$_3$/R$_4$ on the saturated ring]

| Comp. No | R1 | R2 | R3 | R4 | AF9 IC$_{50}$ ± SD (μM) | ENL IC$_{50}$ ± SD (μM) |
|---|---|---|---|---|---|---|
| 38 | 4-ethylphenyl | 2-furyl | H | H | 40 ± 1.5 | 30.7 ± 7.7 |
| 42 | 4-propylphenyl | 2-furyl | H | H | 47.1 ± 2.3 | 58.1 ± 12.0 |
| 41 | 4-methylphenyl | 2-furyl | CH$_3$ | CH$_3$ | 46.4 ± 12.4 | 33.2 ± 8.7 |
| 48 | 4-ethylphenyl | 2-thienyl | H | H | 24.8 ± 1.3 | 19.7 ± 4.0 |
| 52 | 2,5-dimethylphenyl | 3-thienyl | H | H | 43.1 ± 0.8 | 25.1 ± 2.5 |
| 51 | CH$_3$ | 2-thienyl | CH$_3$ | CH$_3$ | >200 | >200 |

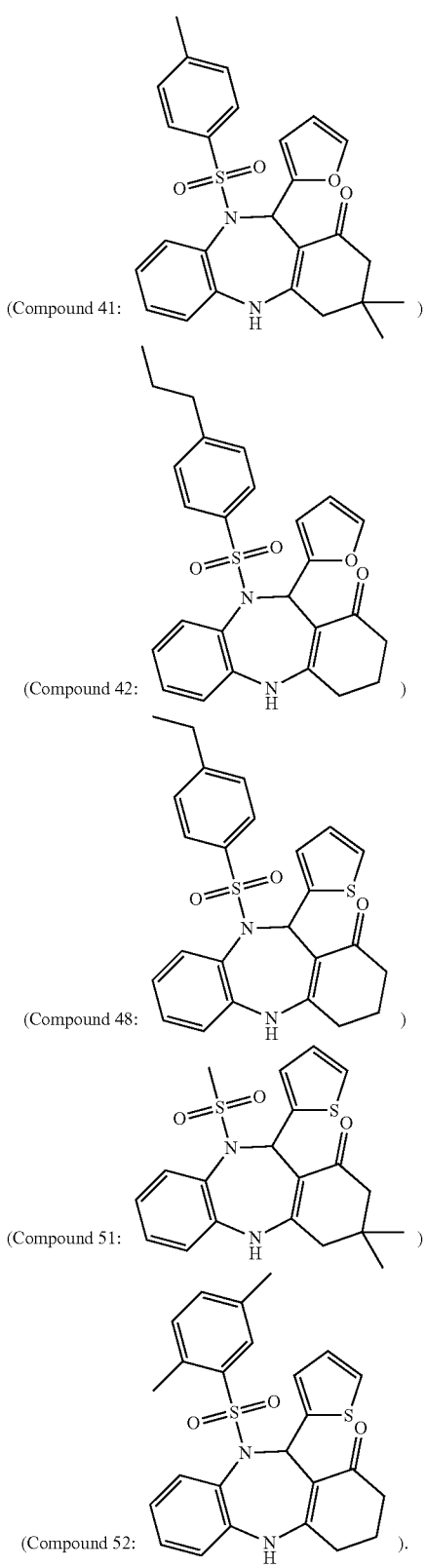

(Compound 41:)
(Compound 42:)
(Compound 48:)
(Compound 51:)
(Compound 52:).

This class of compounds was also tested for their binding against ENL protein, which is highly homologous with AF9. As expected based on previous studies with DOT1L 10 mer peptide (see, e.g., Shen, et al., J Biol Chem. 2013, 288 (42), 30585-96)), the compounds showed a similar pattern in their binding affinities to ENL and to AF9 (Table 4).

Figure 22:
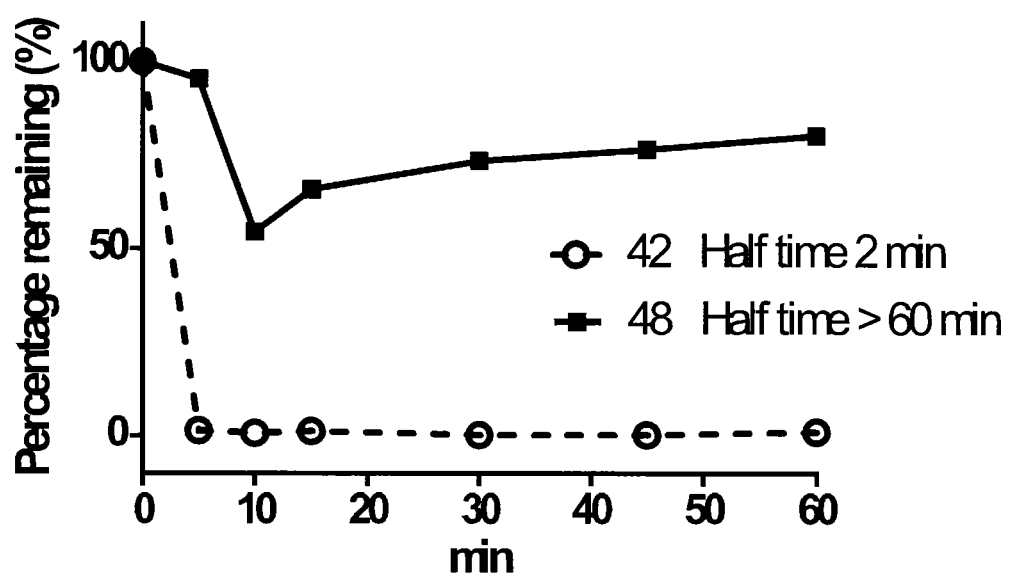
FIG. 22 demonstrates metabolic stability in mouse liver microsome with NADPH.

For optimization of this class of inhibitors besides testing their binding affinity, the physico-chemical properties and microsomal stability will be tested in order to obtain improvement at multiple levels, as necessary for fully optimized compounds. To obtain initial information about the stability of this chemical class of compounds, compounds 42 and 48 have been tested in microsomal stability using mouse liver microsome. Interestingly the half time for these two compounds differs significantly: 2 min and >60 min respectively (FIG. 22). If their structure is analyzed, the major difference between these two compounds is the $R_2$ substituent, furan vs. thiophen. Based on the chemistry of these two moieties, thiophen is more stable in comparison with furan, since the "electron pairs" on sulfur are significantly delocalized in the pi electron system, which makes thiophen more aromatic than furan. These results are essential for future chemical modifications to design and synthesize new analogs with improved binding affinity, proper physico-chemical properties and stability.

Example 14

Figure 23:
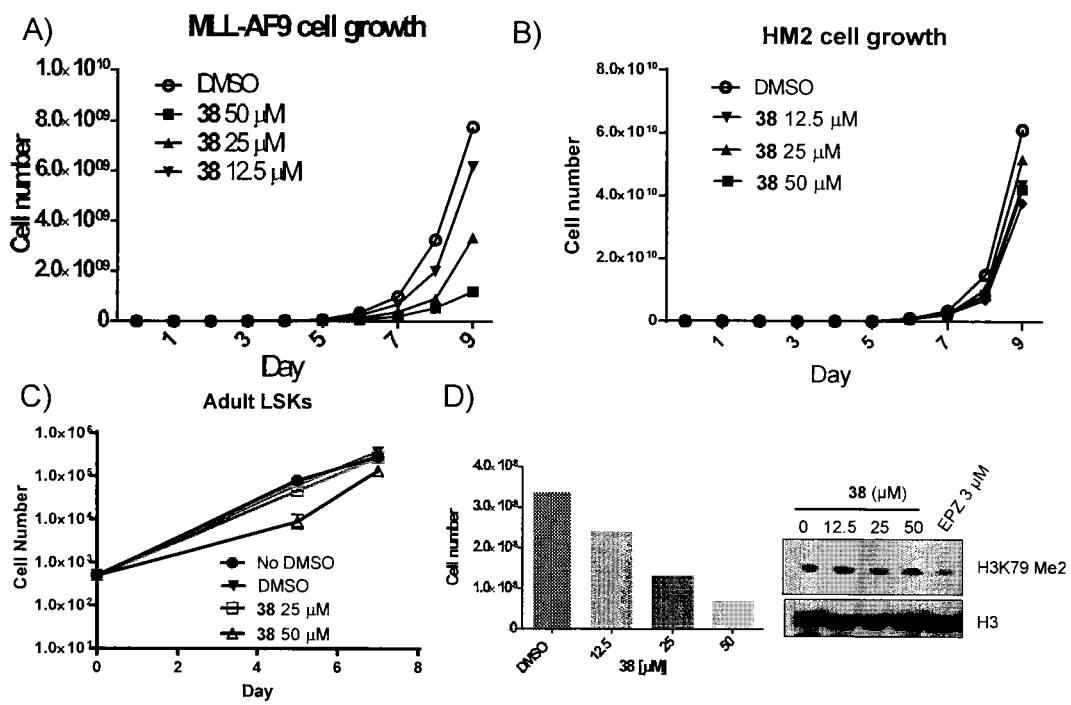
FIG. 23 presents cell growth curves of A) MLL-AF9 and B) Hoxa9/Meis1 transformed mouse cells and C) adult LSKs after treatment with 38. D) H3K79 methylation after 6 days treatment with 38 and EPZ004777 DOT1L inhibitor (see, e.g., Daigle, et al., Cancer Cell 20, 53-65 (2011)).

This example involves the assessment of cellular effects of compound 38. To start investigating the specificity and selectivity of compound 38, MLL-AF9 (highly dependent on DOT1L) transformed mouse cell lines were used (see, e.g., Jo, et al., Blood 117, 4759-4768 (2011)) and HM2 cells stably expressing Hoxa9 and Meis 1, which do not depend on DOT1L. Compound 38 inhibited growth of MLL-AF9 cells in a dose-dependent manner (FIG. 23A), with cell growth inhibition starting after 4 days of treatment. At day 9, 50 μM led to around 90% inhibition while 25 μM induced 50% inhibition. Importantly the cell growth of HM2 cells was not affected, suggesting that growth inhibition is selective to DOT1L-dependent cells (FIG. 23B). The hypothesis predicts that compounds that can block the DOT1L recruitment, but not its catalytic activity, will not affect normal hematopoiesis, as well as the global level of H3K79 methylation. To test this hypothesis, the toxicity of compound 38 was tested on purified LSK (lin-sca-1+ckit+) progenitors from adult wild type mice (FIG. 23C). With up to seven days in culture leading to a ca. 3-log expansion, none of the tested concentrations (50 μM and 25 μM, which have significant inhibition on the MLL-AF9 transformed cells growth) showed growth inhibition of adult LSKs, suggesting that compound 38 is not toxic to normal hematopoiesis, consistent with the prediction. Furthermore, after 6 days treatment of MLL-AF9 transformed cells with 38, the global H3K79 level was not affected in all three tested concentrations although 25 and 50 μM significantly inhibit the cell growth. On the other hand EPZ004777 (a DOT1L SAM competitive inhibitor) showed decreased global level of H3K79 methylation, as expected (FIG. 23D).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A composition comprising a small molecule with the structure

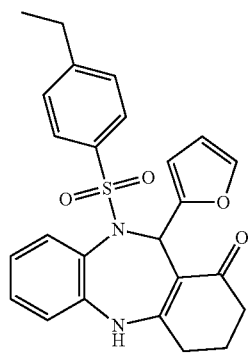 [SMILES: CCc1ccc(S(=O)(=O)N2c3ccccc3NC3=C(C(=O)CCC3)C2c2ccco2)cc1]

and one or more therapeutic agents known to treat cancer.

2. The composition of claim 1, wherein said cancer is leukemia.

3. The composition of claim 2, wherein said leukemia is mixed lineage leukemia (MLL)-fusion protein associated leukemia.

* * * * *

```
                            SEQUENCE LISTING

<160> NUMBER OF SEQ ID NOS: 26

<210> SEQ ID NO 1
<211> LENGTH: 10
<212> TYPE: PRT
<213> ORGANISM: Homo sapiens

<400> SEQUENCE: 1

Leu Pro Ile Ser Ile Pro Leu Ser Thr Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Ala Pro Ile Ser Ile Pro Leu Ser Thr Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Leu Ala Ile Ser Ile Pro Leu Ser Thr Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Leu Pro Ala Ser Ile Pro Leu Ser Thr Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Leu Pro Ile Ala Ile Pro Leu Ser Thr Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 6

Leu Pro Ile Ser Ala Pro Leu Ser Thr Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Leu Pro Ile Ser Ile Ala Leu Ser Thr Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Leu Pro Ile Ser Ile Pro Ala Ser Thr Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Leu Pro Ile Ser Ile Pro Leu Ala Thr Val
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Leu Pro Ile Ser Ile Pro Leu Ser Ala Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Leu Pro Ile Ser Ile Pro Leu Ser Thr Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic
```

<400> SEQUENCE: 12

Leu Pro Ile Ser Ile Pro Leu
1               5

<210> SEQ ID NO 13
<211> LENGTH: 16
<212> TYPE: PRT
<213> ORGANISM: Homo sapiens

<400> SEQUENCE: 13

Leu Pro Ile Ser Ile Pro Leu Ser Thr Val Gln Pro Asn Lys Leu Pro
1               5                   10                  15

<210> SEQ ID NO 14
<211> LENGTH: 14
<212> TYPE: PRT
<213> ORGANISM: Homo sapiens

<400> SEQUENCE: 14

Leu Met Val Lys Ile Thr Leu Asp Leu Leu Ser Arg Ile Pro
1               5                   10

<210> SEQ ID NO 15
<211> LENGTH: 16
<212> TYPE: PRT
<213> ORGANISM: Mus musculus

<400> SEQUENCE: 15

Leu Pro Val Ser Ile Pro Leu Ser Thr Val Gln Pro Asn Lys Leu Pro
1               5                   10                  15

<210> SEQ ID NO 16
<211> LENGTH: 16
<212> TYPE: PRT
<213> ORGANISM: Rattus norvegicus

<400> SEQUENCE: 16

Leu Pro Val Ser Ile Pro Leu Ser Thr Val Gln Pro Asn Lys Leu Pro
1               5                   10                  15

<210> SEQ ID NO 17
<211> LENGTH: 16
<212> TYPE: PRT
<213> ORGANISM: Equus caballus

<400> SEQUENCE: 17

Leu Pro Val Ser Ile Pro Leu Ser Thr Val Gln Pro Ser Lys Leu Pro
1               5                   10                  15

<210> SEQ ID NO 18
<211> LENGTH: 16
<212> TYPE: PRT
<213> ORGANISM: Gallus gallus

<400> SEQUENCE: 18

Leu Pro Ile Ser Ile Pro Leu Ser Thr Val Gln Pro Asn Lys Leu Pro
1               5                   10                  15

<210> SEQ ID NO 19
<211> LENGTH: 16
<212> TYPE: PRT
<213> ORGANISM: Danio rerio

```
<400> SEQUENCE: 19

Leu Pro Ile Ser Ile Pro Leu Ser Thr Val Gln Pro Asn Lys Leu Pro
1               5                   10                  15

<210> SEQ ID NO 20
<211> LENGTH: 16
<212> TYPE: PRT
<213> ORGANISM: Xenopus laevis

<400> SEQUENCE: 20

Leu Pro Ile Ser Ile Pro Leu Ser Thr Val Gln Pro Asn Lys Leu Pro
1               5                   10                  15

<210> SEQ ID NO 21
<211> LENGTH: 72
<212> TYPE: PRT
<213> ORGANISM: Artificial Sequence
<220> FEATURE:
<223> OTHER INFORMATION: Synthetic

<400> SEQUENCE: 21

Gly Glu Cys Asp Lys Ala Tyr Leu Asp Glu Leu Val Glu Leu His Arg
1               5                   10                  15

Arg Leu Met Thr Leu Arg Glu Arg His Ile Leu Gln Gln Ile Val Asn
            20                  25                  30

Leu Ile Glu Glu Thr Gly His Phe His Ile Thr Asn Thr Thr Phe Asp
        35                  40                  45

Phe Asp Leu Cys Ser Leu Asp Lys Thr Thr Val Arg Lys Leu Gln Ser
    50                  55                  60

Tyr Leu Glu Thr Ser Gly Thr Ser
65                  70

<210> SEQ ID NO 22
<211> LENGTH: 71
<212> TYPE: PRT
<213> ORGANISM: Artificial Sequence
<220> FEATURE:
<223> OTHER INFORMATION: Synthetic

<400> SEQUENCE: 22

Gly Thr Tyr Asp Lys Ala Tyr Thr Asp Glu Leu Val Glu Leu His Arg
1               5                   10                  15

Arg Leu Met Ala Leu Arg Glu Arg Asn Val Leu Gln Gln Ile Val Asn
            20                  25                  30

Leu Ile Glu Glu Thr Gly His Phe Asn Val Thr Asn Thr Thr Phe Asp
        35                  40                  45

Phe Asp Leu Phe Ser Leu Asp Glu Thr Thr Val Arg Lys Leu Gln Ser
    50                  55                  60

Cys Leu Glu Ala Val Ala Thr
65                  70

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
tctacggcca taccaccctg a                                        21
```

```
<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gcctacagca cccggtattc c                                             21

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
gccaccatgt acccctacga cgtg                                          24

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
gatttcctcg cagacccacc ggat                                          24
```